US012686853B2

(12) United States Patent
Emerson et al.

(10) Patent No.: US 12,686,853 B2
(45) Date of Patent: Jul. 21, 2026

(54) METHODS AND COMPOSITIONS FOR TREATMENT OF MUSCLE DISEASE WITH iPSC-INDUCED HUMAN SKELETAL MUSCLE STEM CELLS

(71) Applicant: UNIVERSITY OF MASSACHUSETTS, Boston, MA (US)

(72) Inventors: Charles P. Emerson, Lyndon, VT (US); Dongsheng Guo, Shrewsbury, MA (US); Katelyn M. Daman, Stow, MA (US); Jing Yan, Shrewsbury, MA (US); Jennifer Chee-Jen Chen, Kingston (CA); Meng-jiao Shi, Shrewsbury, MA (US); Oliver D. King, Somerville, MA (US); Lawrence J. Hayward, Sterling, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 567 days.

(21) Appl. No.: 18/033,756

(22) PCT Filed: Oct. 25, 2021

(86) PCT No.: PCT/US2021/056404
§ 371 (c)(1),
(2) Date: Apr. 25, 2023

(87) PCT Pub. No.: WO2022/093665
PCT Pub. Date: May 5, 2022

(65) Prior Publication Data
US 2024/0018479 A1 Jan. 18, 2024

Related U.S. Application Data

(60) Provisional application No. 63/192,729, filed on May 25, 2021, provisional application No. 63/105,660, filed on Oct. 26, 2020.

(51) Int. Cl.
*C12N 5/077* (2010.01)

(52) U.S. Cl.
CPC ........ *C12N 5/0658* (2013.01); *C12N 2500/02* (2013.01); *C12N 2501/10* (2013.01); *C12N 2506/45* (2013.01)

(58) Field of Classification Search
CPC .............. C12N 5/0658; C12N 2500/02; C12N 2501/10; C12N 2506/45; A61K 35/30; A61K 35/545; A61P 21/00
See application file for complete search history.

(56) References Cited

U.S. PATENT DOCUMENTS

| | | | |
|---|---|---|---|
| 4,683,195 A | 7/1987 | Mullis et al. | 435/6.11 |
| 4,683,202 A | 7/1987 | Mullis | 435/91.2 |
| 9,862,929 B2 | 1/2018 | Sakurai et al. | |
| 2012/0276070 A1 | 11/2012 | Musick | 424/93.7 |
| 2018/0346879 A1 | 12/2018 | Schmidt et al. | |

FOREIGN PATENT DOCUMENTS

| | | |
|---|---|---|
| WO | WO/2009/142717 | 11/2009 |
| WO | WO/2010/057614 | 5/2010 |
| WO | WO/2015/119642 | 8/2015 |
| WO | WO/2018/128779 | 7/2018 |

OTHER PUBLICATIONS

Castro, A.A., León, M., del Buey Furió, V., Erceg, S. and Lukovic, D., 2018. Generation of a human iPSC line by mRNA reprogramming. Stem cell research, 28, pp. 157-160. (Year: 2018).*

Shoji, E., Woltjen, K. and Sakurai, H., 2015. Directed myogenic differentiation of human induced pluripotent stem cells. In Patient-Specific Induced Pluripotent Stem Cell Models: Generation and Characterization (pp. 89-99). New York, NY: Springer New York. (Year: 2015).*

Al Tanoury, Z. et al. (2021) "Prednisolone rescues Duchenne muscular dystrophy phenotypes in human pluripotent stem cell-derived skeletal muscle in vitro," *Proceedings of the National Academy of Sciences* 118(28), e2022960118.

Alexander, M. S. et al. (2016) "CD82 Is a Marker for Prospective Isolation of Human Muscle Satellite Cells and Is Linked to Muscular Dystrophies," *Cell Stem Cell* 19(6), 800-807.

Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.

Ardhanareeswaran, K. et al. (2017) "Human induced pluripotent stem cells for modelling neurodevelopmental disorders," *Nature Reviews Neurology* 13(5), 265-278.

(Continued)

*Primary Examiner* — Jeremy C Flinders
*Assistant Examiner* — Masudur Rahman
(74) *Attorney, Agent, or Firm* — Medlen & Carroll, LLP

(57) ABSTRACT

Human skeletal muscle stem cells were generated from facioscapulohumeral muscular dystrophy (FSHD) and healthy control iPSC using a transgene-free skeletal muscle differentiation protocol and production of stable iMyoblasts. Analyses revealed that FSHD and healthy control iMyoblasts are embryonic-like myogenic cells that undergo myotube differentiation ex vivo by growth factor depletion and are efficiently transplantable into the tibialis anterior (TA) muscles of NSG mice, where human muscle under-goes embryonic-to-adult myosin isoform switching. The DUX4 FSHD disease gene maintains its hypomethylated disease state inFSHD iPSC and iMyoblast, and its expression is upregulated during myotube differentiation and in muscle xenografts. Consequently, these iMyoblasts accurately exhibit the molecular pathology of human muscular dystrophies and are useful for the development of drug, gene editing and stem cell therapeutics.

13 Claims, 27 Drawing Sheets
Specification includes a Sequence Listing.

(56) References Cited

OTHER PUBLICATIONS

Barberi, T. et al. (2007) "Derivation of engraftable skeletal myoblasts from human embryonic stem cells," *Nature Medicine* 13(5), 642-648.

Baroffio, A. et al. (1996) "Identification of self-renewing myoblasts in the progeny of single human muscle satellite cells," *Differentiation* 60(1), 47-57.

Benezra, R. et al. (1990) "The protein Id: A negative regulator of helix-loop-helix DNA binding proteins," *Cell* 61(1), 49-59.

Berkes, C. A. et al. (2005) "MyoD and the transcriptional control of myogenesis," *Seminars in Cell & Developmental Biology* 16(4), 585-595.

Borchin, B. et al. (2013) "Derivation and FACS-Mediated Purification of PAX3+/PAX7+ Skeletal Muscle Precursors from Human Pluripotent Stem Cells," *Stem Cell Reports* 1(6), 620-631.

Bosnakovski, D. et al. (2008) "An isogenetic myoblast expression screen identifies DUX4-mediated FSHD-associated molecular pathologies," *The EMBO Journal* 27(20), 2766-2779.

Brunk, B. P. et al. (1996) "Regulated Demethylation of themyoD-Distal Enhancer during Skeletal Myogenesis," *Developmental Biology* 177(2), 490-503.

Buckingham, M. et al. (2007) "The Role of Pax Genes in the Development of Tissues and Organs: Pax3 and Pax7 Regulate Muscle Progenitor Cell Functions," *Annual Review of Cell and Developmental Biology* 23(1), 645-673.

Burridge, P. W. et al. (2014) "Chemically defined generation of human cardiomyocytes," *Nature Methods* 11(8), 855-860.

Butler, A. et al. (2018) "Integrating single-cell transcriptomic data across different conditions, technologies, and species," *Nature Biotechnology* 36(5), 411-420.

Caron, L. et al. (2016) "A Human Pluripotent Stem Cell Model of Facioscapulohumeral Muscular Dystrophy-Affected Skeletal Muscles," *Stem Cells Translational Medicine* 5(9), 1145-1161.

Chal, J. et al. (2016) "Generation of human muscle fibers and satellite-like cells from human pluripotent stem cells in vitro," *Nature Protocols* 11(10), 1833-1850.

Chal, J. et al. (2018) "Recapitulating early development of mouse musculoskeletal precursors of the paraxial mesoderm in vitro," *Development* 145(6).

Chal, J. et al. (2015) "Differentiation of pluripotent stem cells to muscle fiber to model Duchenne muscular dystrophy," *Nature Biotechnology* 33(9), 962-969.

Chal, J. et al. (2017) "Making muscle: skeletal myogenesis in vivo and in vitro," *Development* 144(12), 2104-2122.

Chang, C.-N. et al. (2018) "Location, Location, Location: Signals in Muscle Specification," *Journal of Developmental Biology* 6(2), 11.

Charlton, C. A. et al. (1997) "Fusion Competence of Myoblasts Rendered Genetically Null for N-Cadherin in Culture," *Journal of Cell Biology* 138(2), 331-336.

Chen, J. C. J. et al. (2016) "Morpholino-mediated Knockdown of DUX4 Toward Facioscapulohumeral Muscular Dystrophy Therapeutics," *Molecular Therapy* 24(8), 1405-1411.

Choi, In Y. et al. (2016) "Concordant but Varied Phenotypes among Duchenne Muscular Dystrophy Patient-Specific Myoblasts Derived using a Human iPSC-Based Model," *Cell Reports* 15(10), 2301-2312.

Contreras, O. et al. (2016) "Connective tissue cells expressing fibro/adipogenic progenitor markers increase under chronic damage: relevance in fibroblast-myofibroblast differentiation and skeletal muscle fibrosis," *Cell and Tissue Research* 364(3), 647-660.

Csapo, R. et al. (2020) "Skeletal Muscle Extracellular Matrix—What Do We Know About Its Composition, Regulation, and Physiological Roles? A Narrative Review," *Frontiers in Physiology 11*.

Dandapat, A. et al. (2014) "Dominant Lethal Pathologies in Male Mice Engineered to Contain an X-Linked DUX4 Transgene," *Cell Reports* 8(5), 1484-1496.

Darabi, R. et al. (2012) "Human ES- and iPS-Derived Myogenic Progenitors Restore Dystrophin and Improve Contractility upon Transplantation in Dystrophic Mice," *Cell Stem Cell* 10(5), 610-619.

De Greef, J. C. et al. (2009) "Common epigenetic changes of D4Z4 in contraction-dependent and contraction-independent FSHD," *Human Mutation* 30(10), 1449-1459.

De Iaco, A. et al. (2017) "DUX-family transcription factors regulate zygotic genome activation in placental mammals," *Nature Genetics* 49(6), 941-945.

Dieffenbach, C. W. et al. (1995) *PCR Primer, A Laboratory Manual*, Cold Spring Harbor Laboratory Press, Plainview, N.Y.

Dion, C. et al. (2019) "SMCHD1 is involved in de novo methylation of the DUX4-encoding D4Z4 macrosatellite," *Nucleic Acids Research* 47(6), 2822-2839.

Fabre, O. et al. (2020) "GREM1 is epigenetically reprogrammed in muscle cells after exercise training and controls myogenesis and metabolism," *bioRxiv*, 2020.2002.2020.956300.

Flamini, V. et al. (2018) "The Satellite Cell Niche Regulates the Balance between Myoblast Differentiation and Self-Renewal via p53," *Stem Cell Reports* 10(3), 970-983.

Gabriëls, J. et al. (1999) "Nucleotide sequence of the partially deleted D4Z4 locus in a patient with FSHD identifies a putative gene within each 3.3 kb element," *Gene* 236(1), 25-32.

Gao, H. et al. (2017) "Ubiquitin C-Terminal Hydrolase L1 regulates myoblast proliferation and differentiation," *Biochemical and Biophysical Research Communications* 492(1), 96-102.

Geng, Linda N. et al. (2012) "DUX4 Activates Germline Genes, Retroelements, and Immune Mediators: Implications for Facioscapulohumeral Dystrophy," *Developmental Cell* 22(1), 38-51.

Georgomanoli, M. et al. (2019) "Modeling blood diseases with human induced pluripotent stem cells," *Disease Models & Mechanisms* 12(6).

Gillies, A. R. et al. (2011) "Structure and function of the skeletal muscle extracellular matrix," *Muscle & Nerve* 44(3), 318-331.

Gunhanlar, N. et al. (2018) "A simplified protocol for differentiation of electrophysiologically mature neuronal networks from human induced pluripotent stem cells," *Molecular Psychiatry* 23(5), 1336-1344.

Hafemeister, C. et al. (2019) "Normalization and variance stabilization of single-cell RNA-seq data using regularized negative binomial regression," *bioRxiv*, 576827.

Hashimoto, A. et al. (2016) "Generation of Induced Pluripotent Stem Cells From Patients With Duchenne Muscular Dystrophy and Their Induction to Cardiomyocytes," *International Heart Journal* 57(1), 112-117.

Heckmann, B. L. et al. (2013) "The G0/G1 switch gene 2 (G0S2): Regulating metabolism and beyond," *Biochimica et Biophysica Acta (BBA)—Molecular and Cell Biology of Lipids* 1831(2), 276-281.

Hendrickson, P. G. et al. (2017) "Conserved roles of mouse DUX and human DUX4 in activating cleavage-stage genes and MERVL/HERVL retrotransposons," *Nature Genetics* 49(6), 925-934.

Heslop, J. A. et al. (2019) "The Use of Human Pluripotent Stem Cells for Modeling Liver Development and Disease," *Hepatology* 69(3), 1306-1316.

Hicks, M. R. et al. (2018) "ERBB3 and NGFR mark a distinct skeletal muscle progenitor cell in human development and hPSCs," *Nature Cell Biology* 20(1), 46-57.

Homma, S. et al. (2012) "A unique library of myogenic cells from facioscapulohumeral muscular dystrophy subjects and unaffected relatives: family, disease and cell function," *European Journal of Human Genetics* 20(4), 404-410.

Hosoyama, T. et al. (2014) "Derivation of Myogenic Progenitors Directly From Human Pluripotent Stem Cells Using a Sphere-Based Culture," *Stem Cells Translational Medicine* 3(5), 564-574.

Hurlbert, S. H. (1984) "Pseudoreplication and the Design of Ecological Field Experiments," *Ecological Monographs* 54(2), 187-211.

Iyer, S. et al. (2019) "Precise therapeutic gene correction by a simple nuclease-induced double-stranded break," *Nature* 568(7753), 561-565.

(56)            References Cited

OTHER PUBLICATIONS

Jiwlawat, N. et al. (2018) "Current Progress and Challenges for Skeletal Muscle Differentiation from Human Pluripotent Stem Cells Using Transgene-Free Approaches," *Stem Cells International* 2018, 6241681.

Joe, A. W. B. et al. (2010) "Muscle injury activates resident fibro/adipogenic progenitors that facilitate myogenesis," *Nature Cell Biology* 12(2), 153-163.

Jones, T. I. et al. (2012) "Facioscapulohumeral muscular dystrophy family studies of DUX4 expression: evidence for disease modifiers and a quantitative model of pathogenesis," *Human Molecular Genetics* 21(20), 4419-4430.

Jones, T. I. et al. (2015) "Individual epigenetic status of the pathogenic D4Z4 macrosatellite correlates with disease in facioscapulohumeral muscular dystrophy," *Clinical Epigenetics* 7(1), 37.

Jones, T. I. et al. (2014) "Identifying diagnostic DNA methylation profiles for facioscapulohumeral muscular dystrophy in blood and saliva using bisulfite sequencing," *Clinical Epigenetics* 6(1), 23.

Kammoun, M. et al. (2014) "A simplified immunohistochemical classification of skeletal muscle fibres in mouse," *European Journal of Histochemistry* 58(2), 2254.

Kang, H. M. et al. (2018) "Multiplexed droplet single-cell RNA-sequencing using natural genetic variation," *Nature Biotechnology* 36(1), 89-94.

Kava, M. et al. (2013) "Eye and Brain Abnormalities in Congenital Muscular Dystrophies Caused by Fukutin-Related Protein Gene (FKRP) Mutations," *Pediatric Neurology* 49(5), 374-378.

Lagha, M. et al. (2009) "Pax3:Foxc2 Reciprocal Repression in the Somite Modulates Muscular versus Vascular Cell Fate Choice in Multipotent Progenitors," *Developmental Cell* 17(6), 892-899.

Lapan, A. D. et al. (2012) "Human fetal skeletal muscle contains a myogenic side population that expresses the melanoma cell-adhesion molecule," *Human Molecular Genetics* 21(16), 3668-3680.

Laumonier, T. et al. (2017) "Human myogenic reserve cells are quiescent stem cells that contribute to muscle regeneration after intramuscular transplantation in immunodeficient mice," *Scientific Reports* 7(1), 3462.

Lee, A. S. J. et al. (2013) "Initiation of primary myogenesis in amniote limb muscles," *Developmental Dynamics* 242(9), 1043-1055.

Lee, H.-J. et al. (2017) "Dysregulation of nuclear receptor COUP-TFII impairs skeletal muscle development," *Scientific Reports* 7(1), 3136.

Lemmers, R. J. L. F. et al. (2012) "Digenic inheritance of an SMCHD1 mutation and an FSHD-permissive D4Z4 allele causes facioscapulohumeral muscular dystrophy type 2," *Nature Genetics* 44(12), 1370-1374.

Lemmers, R. J. L. F. et al. (2010) "A Unifying Genetic Model for Facioscapulohumeral Muscular Dystrophy," *Science* 329(5999), 1650-1653.

Li, H. et al. (1994) "Inhibition of desmin expression blocks myoblast fusion and interferes with the myogenic regulators MyoD and myogenin," *Journal of Cell Biology* 124(5), 827-841.

Li, Z. et al. (2012) "An HMGA2-IGF2BP2 Axis Regulates Myoblast Proliferation and Myogenesis," *Developmental Cell* 23(6), 1176-1188.

Lim, J.-W. et al. (2015) "DICER/AGO-dependent epigenetic silencing of D4Z4 repeats enhanced by exogenous siRNA suggests mechanisms and therapies for FSHD," *Human Molecular Genetics* 24(17), 4817-4828.

Lu, L. et al. (2013) "Genome-wide survey by ChIP-seq reveals YY1 regulation of lincRNAs in skeletal myogenesis," *The EMBO Journal* 32(19), 2575-2588.

Lun, A. T. L. et al. (2016) "It's DE-licious: A Recipe for Differential Expression Analyses of RNA-seq Experiments Using Quasi-Likelihood Methods in edgeR," in *Statistical Genomics: Methods and Protocols* (Mathé, E., et al., Eds.), pp. 391-416, Springer New York, New York, NY.

Maffioletti, S. M. et al. (2015) "Efficient derivation and inducible differentiation of expandable skeletal myogenic cells from human ES and patient-specific iPS cells," *Nature Protocols* 10(7), 941-958.

Maffioletti, S. M. et al. (2018) "Three-Dimensional Human iPSC-Derived Artificial Skeletal Muscles Model Muscular Dystrophies and Enable Multilineage Tissue Engineering," *Cell Reports* 23(3), 899-908.

Magli, A. et al. (2017) "PAX7 Targets, CD54, Integrin $\alpha9\beta1$, and SDC2, Allow Isolation of Human ESC/iPSC-Derived Myogenic Progenitors," *Cell Reports* 19(13), 2867-2877.

Mcinnes, L. et al. (2018) "Umap: Uniform manifold approximation and projection for dimension reduction," *arXiv*, 180203426.

Mercatelli, N. et al. (2017) "MiR-23-TrxR1 as a novel molecular axis in skeletal muscle differentiation," *Scientific Reports* 7(1), 7219.

Mitsuhashi, H. et al. (2012) "Expression of DUX4 in zebrafish development recapitulates facioscapulohumeral muscular dystrophy," *Human Molecular Genetics* 22(3), 568-577.

Oikkonen, L. et al. (2017) "Making the most of RNA-seq: Preprocessing sequencing data with Opossum for reliable SNP variant detection," *Wellcome Open Res* 2, 6.

Olson, L. E. et al. (2009) "Increased PDGFRα Activation Disrupts Connective Tissue Development and Drives Systemic Fibrosis," *Developmental Cell* 16(2), 303-313.

Pagliuca, Felicia W. et al. (2014) "Generation of Functional Human Pancreatic β Cells In Vitro," *Cell* 159(2), 428-439.

Pakula, A. et al. (2019) "Purification of Myogenic Progenitors from Human Muscle Using Fluorescence-Activated Cell Sorting (FACS)," *Methods in Molecular Biology* 1889, 1-15.

Pandey, S. N. et al. (2015) "Culture Conditions Affect Expression of DUX4 in FSHD Myoblasts," *Molecules* 20(5), 8304-8315.

Rao, L. et al. (2018) "Engineering human pluripotent stem cells into a functional skeletal muscle tissue," *Nature Communications* 9(1), 126.

Rayagiri, S. S. et al. (2018) "Basal lamina remodeling at the skeletal muscle stem cell niche mediates stem cell self-renewal," *Nature Communications* 9(1), 1075.

Replogle, J. M. et al. (2020) "Combinatorial single-cell CRISPR screens by direct guide RNA capture and targeted sequencing," *Nature Biotechnology* 38(8), 954-961.

Rickard, A. M. et al. (2015) "Endogenous DUX4 expression in FSHD myotubes is sufficient to cause cell death and disrupts RNA splicing and cell migration pathways," *Human Molecular Genetics* 24(20), 5901-5914.

Ridgeway, A. G. et al. (2001) "Pax3 Is Essential for Skeletal Myogenesis and the Expression of Six1 and Eya2*," *Journal of Biological Chemistry* 276(22), 19033-19039.

Rimmer, A. et al. (2014) "Integrating mapping-, assembly- and haplotype-based approaches for calling variants in clinical sequencing applications," *Nature Genetics* 46(8), 912-918.

Robinson, M. D. et al. (2009) "edgeR: a Bioconductor package for differential expression analysis of digital gene expression data," *Bioinformatics* 26(1), 139-140.

Rohde, C. et al. (2008) "Bisulfite sequencing Data Presentation and Compilation (BDPC) web server—a useful tool for DNA methylation analysis," *Nucleic Acids Research* 36(5), e34-e34.

Rohde, C. et al. (2010) "BISMA—Fast and accurate bisulfite sequencing data analysis of individual clones from unique and repetitive sequences," *BMC Bioinformatics* 11(1), 230.

Rohde, C. et al. (2009) "New clustering module in BDPC bisulfite sequencing data presentation and compilation web application for DNA methylation analyses," *BioTechniques* 47(3), 781-783.

Rojas, L. A. et al. (2020) "p38α Regulates Expression of DUX4 in a Model of Facioscapulohumeral Muscular Dystrophy," *Journal of Pharmacology and Experimental Therapeutics* 374(3), 489-498.

Rouger, K. et al. (2011) "Systemic Delivery of Allogenic Muscle Stem Cells Induces Long-Term Muscle Repair and Clinical Efficacy in Duchenne Muscular Dystrophy Dogs," *American Journal of Pathology* 179(5), 2501-2518.

Scaramozza, A. et al. (2019) "Lineage Tracing Reveals a Subset of Reserve Muscle Stem Cells Capable of Clonal Expansion under Stress," *Cell Stem Cell* 24(6), 944-957.e945.

(56)          References Cited

OTHER PUBLICATIONS

Schiaffino, S. et al. (2011) "Fiber Types in Mammalian Skeletal Muscles," *Physiological Reviews* 91(4), 1447-1531.

Schiaffino, S. et al. (2015) "Developmental myosins: expression patterns and functional significance," *Skeletal Muscle* 5(1), 22.

Selvaraj, S. et al. (2019) "Screening identifies small molecules that enhance the maturation of human pluripotent stem cell-derived myotubes," *eLife 8*, e47970.

Shelton, M. et al. (2014) "Derivation and Expansion of PAX7-Positive Muscle Progenitors from Human and Mouse Embryonic Stem Cells," *Stem Cell Reports* 3(3), 516-529.

Snider, L. et al. (2010) "Facioscapulohumeral Dystrophy: Incomplete Suppression of a Retrotransposed Gene," *PLOS Genetics* 6(10), e1001181.

Song, Z. et al. (2009) "Efficient generation of hepatocyte-like cells from human induced pluripotent stem cells," *Cell Research* 19(11), 1233-1242.

Springer, M. L. et al. (1997) "High-efficiency retroviral infection of primary myoblasts," *Somatic Cell and Molecular Genetics* 23(3), 203-209.

Stuart, T. et al. (2019) "Comprehensive Integration of Single-Cell Data," *Cell* 177(7), 1888-1902.e1821.

Swartz, E. W. et al. (2016) "A Novel Protocol for Directed Differentiation of C9orf72-Associated Human Induced Pluripotent Stem Cells Into Contractile Skeletal Myotubes," *Stem Cells Translational Medicine* 5(11), 1461-1472.

Takahashi, K. et al. (2007) "Induction of Pluripotent Stem Cells from Adult Human Fibroblasts by Defined Factors," *Cell* 131(5), 861-872.

Tawil, R. et al. (2006) "Facioscapulohumeral muscular dystrophy," *Muscle & Nerve* 34(1), 1-15.

Thorsteinsdottir, S. et al. (2011) "The extracellular matrix dimension of skeletal muscle development," *Developmental Biology* 354(2), 191-207.

Tung, P.-Y. et al. (2017) "Batch effects and the effective design of single-cell gene expression studies," *Scientific Reports* 7(1), 39921.

Uezumi, A. et al. (2016) "Cell-Surface Protein Profiling Identifies Distinctive Markers of Progenitor Cells in Human Skeletal Muscle," *Stem Cell Reports* 7(2), 263-278.

Van Den Boogaard, Marlinde L. et al. (2016) "Mutations in DNMT3B Modify Epigenetic Repression of the D4Z4 Repeat and the Penetrance of Facioscapulohumeral Dystrophy," *American Journal of Human Genetics* 98(5), 1020-1029.

Van Mil, A. et al. (2018) "Modelling inherited cardiac disease using human induced pluripotent stem cell-derived cardiomyocytes: progress, pitfalls, and potential," *Cardiovascular Research* 114(14), 1828-1842.

Van Overveld, P. G. M. et al. (2003) "Hypomethylation of D4Z4 in 4q-linked and non-4q-linked facioscapulohumeral muscular dystrophy," *Nature Genetics* 35(4), 315-317.

Velling, T. et al. (1999) "cDNA Cloning and Chromosomal Localization of Human $\alpha 11$ Integrin: A Collagen-Binding, I Domain-Containing, $\beta 1$-Associated Integrin $\alpha$-Chain Present in Muscle Tissues*," *Journal of Biological Chemistry* 274(36), 25735-25742.

Von Maltzahn, J. et al. (2012) "Wnt signaling in myogenesis," *Trends in Cell Biology* 22(11), 602-609.

Wallace, L. M. et al. (2011) "DUX4, a candidate gene for facioscapulohumeral muscular dystrophy, causes p53-dependent myopathy in vivo," *Annals of Neurology* 69(3), 540-552.

Wang, L. C. et al. (2001) "Fibre type regionalisation in lower hindlimb muscles of rabbit, rat and mouse: a comparative study," *Journal of Anatomy* 199(6), 631-643.

Weintraub, H. et al. (1989) "Activation of muscle-specific genes in pigment, nerve, fat, liver, and fibroblast cell lines by forced expression of MyOD," *Proceedings of the National Academy of Sciences* 86(14), 5434-5438.

Xi, H. et al. (2017) "In Vivo Human Somitogenesis Guides Somite Development from hPSCs," *Cell Reports* 18(6), 1573-1585.

Xi, H. et al. (2020) "A Human Skeletal Muscle Atlas Identifies the Trajectories of Stem and Progenitor Cells across Development and from Human Pluripotent Stem Cells," *Cell Stem Cell* 27(1), 158-176.e110.

Xu, C. et al. (2013) "A Zebrafish Embryo Culture System Defines Factors that Promote Vertebrate Myogenesis across Species," *Cell* 155(4), 909-921.

Yang, Q. et al. (2016) "PAX3+ skeletal muscle satellite cells retain long-term self-renewal and proliferation," *Muscle & Nerve* 54(5), 943-951.

Yao, Z. et al. (2014) "DUX4-induced gene expression is the major molecular signature in FSHD skeletal muscle," *Human Molecular Genetics* 23(20), 5342-5352.

Yilmaz, A. et al. (2016) "MuSK is a BMP co-receptor that shapes BMP responses and calcium signaling in muscle cells," *Science Signaling* 9(444), ra87-ra87.

Yoshida, N. et al. (1998) "Cell heterogeneity upon myogenic differentiation: down-regulation of MyoD and Myf-5 generates 'reserve cells'," *Journal of Cell Science* 111(6), 769-779.

Young, M. D. et al. (2010) "Gene ontology analysis for RNA-seq: accounting for selection bias," *Genome Biology* 11(2), R14.

Zhang, J. M. et al. (2019) "Valid Post-clustering Differential Analysis for Single-Cell RNA-Seq," *Cell Systems* 9(4), 383-392.e386.

PCT International Search Report of International Application No. PCT/US2021/056404 dated Feb. 4, 2022.

* cited by examiner

SEQUENCE LISTING

<160> NUMBER OF SEQ ID NOS: 31

<210> SEQ ID NO 1
<211> LENGTH: 37
<212> TYPE: DNA
<213> ORGANISM: Artificial Sequence

```
<220> FEATURE:
<223> OTHER INFORMATION: Synthetic

<400> SEQUENCE: 1
agttgggggt atttatgggt ttttttataa atttttg                              37

<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
ccccaaacct caaaactcaa ttaaaaaaac c                                    31

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
gttttgttgg aggagtttta gga                                            23

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
aacattcaac caaaatttca craaa                                          25

<210> SEQ ID NO 5
<211> LENGTH: 29
<212> TYPE: DNA
<213> ORGANISM: Artificial Sequence
<220> FEATURE:
<223> OTHER INFORMATION: Synthetic

<400> SEQUENCE: 5
aacaaaaata tacttttaac crccaaaaa                                      29

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
aacctcctcc ttttccaagc                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
gcagtacctg tttagccacg a                                              21
```

-continued

```
<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
atgccattcg gtaacaccca c                                            21

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
gcttcttgta gagttcaagg gtc                                          23

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
aatgcaagtg ctattccaga gg                                           22

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
acagacagct tgtgttcttg tt                                           22

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
ggggaaaact acctgcctgt c                                            21

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
aggcgctcga tgtactggat                                              20

<210> SEQ ID NO 14
<211> LENGTH: 18
<212> TYPE: DNA
<213> ORGANISM: Artificial Sequence
<220> FEATURE:
<223> OTHER INFORMATION: Synthetic
```

<400> SEQUENCE: 14
gcggaactgc tacgaagg                                               18

<210> SEQ ID NO 15
<211> LENGTH: 18
<212> TYPE: DNA
<213> ORGANISM: Artificial Sequence
<220> FEATURE:
<223> OTHER INFORMATION: Synthetic

<400> SEQUENCE: 15
agggctctcg gtggagat                                               18

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
caccttcaca gcagaacagc                                             20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
cagcttgctt cctccatctt                                             20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gggaagaaag aggaggagga                                             20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ttcagtggga ggtcaggttc                                             20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
ccacctccaa ctgctctgat                                             20

<210> SEQ ID NO 21

```
<211> LENGTH: 20
<212> TYPE: DNA
<213> ORGANISM: Artificial Sequence
<220> FEATURE:
<223> OTHER INFORMATION: Synthetic

<400> SEQUENCE: 21
tgatccggtc cactatgttg                                       20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
gcgttcacct cttttccaag                                       20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gccatgtgga tttctcgttt                                       20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
acccatcact ggactggtgt                                       20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
cacatcctca aagagcctga                                       20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
tggaaatcaa gtggcaaaaa                                       20

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
```

-continued

```
ctgcatgtgg acgtggac                                                      18

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
tggctacaat ggggaaactg                                                    20

<210> SEQ ID NO 29
<211> LENGTH: 19
<212> TYPE: DNA
<213> ORGANISM: Artificial Sequence
<220> FEATURE:
<223> OTHER INFORMATION: Synthetic

<400> SEQUENCE: 29
ctgctgcctc ttccatttg                                                     19

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
ggcccggtga gagactccac a                                                  21

<210> SEQ ID NO 31
<211> LENGTH: 30
<212> TYPE: DNA
<213> ORGANISM: Artificial Sequence
<220> FEATURE:
<223> OTHER INFORMATION: Synthetic

<400> SEQUENCE: 31
ccaggagatg taactctaat ccaggtttgc                                         30
```

METHODS AND COMPOSITIONS FOR TREATMENT OF MUSCLE DISEASE WITH iPSC-INDUCED HUMAN SKELETAL MUSCLE STEM CELLS

STATEMENT REGARDING FEDERALLY SPONSORED RESEARCH OR DEVELOPMENT

This invention was made with government support under Grant Nos. HD060848 and HD007796 awarded by the National Institutes of Health. The government has certain rights in the invention.

FIELD OF THE INVENTION

The present invention is related to the field of stem cell therapeutics. In particular, a method to generate large numbers of human muscle stem cell lines from normal and patient derived iPSCs. Such a method provides human stem cells useful for ex vivo muscle differentiation and in vivo muscle engraftment therapeutics. Further, the methods provide for the efficient isolation and expansion of human skeletal muscle stem cells from iPSCs for muscle disease modeling, gene editing, and stem cell and autologous stem cell and allogenic stem cell transplantation therapies.

BACKGROUND

Present technologies for reprogramming of human patient cells into induced pluripotent stem cells (iPSCs) and for inducing iPSCs to differentiate into specific differentiated cell types are related to the study of mechanisms of human tissue differentiation, the molecular pathology of human diseases, and development of novel drug, gene editing, and stem cell therapeutics. Takahashi et al., (2007). Protocols have been reported for differentiating human iPSCs into neurons, cardiomyocytes, pancreatic 3 cells, hepatocytes and skeletal muscle, among other tissues. Gunhanlar et al., (2018); Burridge et al., (2014); Pagliuca et al., (2014); Song et al., (2009); and Jiwlawat et al., (2018). Much of the past research on iPSC cell-type induction has focused on optimizing production of differentiated cells that provide a platform for investigations of disease pathologies. Ardhanareeswaran et al., (2017); Georgomanoli and Papapetrou, (2019); Hashimoto et al., (2016); Heslop and Duncan, (2019); and van Mil et al., (2018). Notably, however, technologies for production of lineage-specific stem cells for studies of differentiation and genetic and epigenetic disease mechanisms and for implementation of drug, gene correction and autologous transplantation therapies using patient cells are not well developed.

What is needed in the art are reliable and efficient protocols to produce human skeletal muscle stem cells from iPSCs reprogrammed from adult cells.

SUMMARY OF THE INVENTION

The present invention is related to the field of stem cell therapeutics. In particular, a method to generate large numbers of human muscle stem cell lines from normal and patient derived iPSCs. Such a method provides human stem cells useful for ex vivo muscle differentiation and in vivo muscle engraftment therapeutics. Further, the methods provide for the efficient isolation and expansion of human skeletal muscle stem cells from iPSCs for muscle disease modeling, gene editing, and stem cell and autologous stem cell and allogenic stem cell transplantation therapies.

In one embodiment, the present invention contemplates a method, comprising: a) providing induced pluripotent stem cells; b) stimulating said induced pluripotent stem cells in a media comprising progenitor factors under five percent (5%) oxygen to create induced primary tissue stem cells; c) culturing said induced primary tissue stem cells under twenty percent (20%) oxygen to create a first plurality of undifferentiated tissue stem cells; d) differentiating said first plurality undifferentiated tissue stem cells in a transgene-free growth factor media under twenty percent (20%) oxygen to create induced secondary tissue stem cells, wherein said induced secondary tissue stem cells retain a genetic identity identical to that of said induced pluripotent stem cells. In one embodiment, the method further comprises expanding said iMyoblast to create a somatic tissue and a second plurality of undifferentiated stem cells. In one embodiment, the somatic tissue further differentiates into a differentiated somatic tissue. In one embodiment, the iPSCs are derived from a healthy subject. In one embodiment, the iPSCs are derived from a subject diagnosed with FSHD1. In one embodiment, the iPSCs are derived from a subject diagnosed with FKRP dystroglycanopathy. In one embodiment, the iPSCs are derived from a subject diagnosed with LGMD R7 (formerly LGMD 2G). In one embodiment, the method further comprises propagating the second plurality of undifferentiated stem cells in the presence of the somatic tissue. In one embodiment, the genetic identity of the propagated second plurality of undifferentiated stem cells is stable. In one embodiment, the method further comprises inducing the expanded second plurality of undifferentiated stem cells into induced tertiary stem cells with a growth medium.

In one embodiment, the present invention contemplates a method, comprising: a) providing induced pluripotent stem cells; b) stimulating said induced pluripotent stem cells in a media comprising progenitor factors under five percent (5%) oxygen to create induced primary myoblast stem cells; c) culturing said induced primary myoblast stem cells under twenty percent (20%) oxygen to create a first plurality of undifferentiated myogenic stem cells; d) propagating said undifferentiated myogenic stem cells in a transgene-free growth factor media under twenty percent (20%) oxygen to create induced secondary myocytes, wherein said induced secondary myocytes retain a genetic identity identical to that of said induced pluripotent stem cells. In one embodiment, the method further comprises expanding said induced secondary myocytes to create a myotube tissue and a second plurality of undifferentiated stem cells. In one embodiment, the myotube tissue further differentiates into a striated muscle tissue. In one embodiment, the iPSCs are derived from a healthy subject. In one embodiment, the iPSCs are derived from a subject diagnosed with FSHD1. In one embodiment, the iPSC is derived from a subject diagnosed with FKRP dystroglycanopathy. In one embodiment, the iPSCs are derived from a subject diagnosed with LGMD R7. In one embodiment, the method further comprises propagating the second plurality of undifferentiated stem cells in the presence of the myotube tissue. In one embodiment, the second plurality of undifferentiated stem cells retain an autonomous expression of PAX3 and MYOD1 muscle master regulatory genes. In one embodiment, the muscle master regulatory genes are upregulated. In one embodiment, the second plurality of undifferentiated stem cells retain a commitment to myotube differentiation. In one embodiment, the genetic identity of the expanded second plurality of undifferentiated stem cells is stable. In one embodiment, the method further comprises inducing the expanded second plurality of undifferentiated stem cells into induced tertiary myoblasts with a growth medium.

In one embodiment, the present invention contemplates a method, comprising: a) providing; i) a patient exhibiting at least one symptom of a muscular disorder; and ii) a composition comprising iMyoblasts derived from undifferentiated stem cells, said undifferentiated stem cells generated from induced pluripotent stem cells, wherein the iMyoblasts retain a genetic identity identical to that of said induced pluripotent stem cells; b) administering said composition to said patient under conditions such that said at least one symptom of said muscular disorder is reduced. In one embodiment, said administering further comprises transplantation of said iMyoblasts into said patient. In one embodiment, the transplanted iMyoblasts undergo embryonic to adult myosin isoform switching. In one embodiment, the iMyoblasts comprise regulatory plasticity and obtain adult myogenesis and muscle maturation. In one embodiment, said transplanted iMyoblasts differentiate into a striated muscle tissue. In one embodiment, said reprogrammed induced pluripotent stem cells are patient-derived reprogrammed induced pluripotent stem cells. In one embodiment, the muscular disorder is FSHD1. In one embodiment, the muscular disorder is FKRP dystroglycanopathy. In one embodiment, the muscular disorder is LGMD R7. In one embodiment, the patient further comprises a hypomethylated DUX4 gene. In one embodiment, the patient further comprises a decondensed DUX4 gene. In one embodiment, the muscle disorder is a muscle injury. In one embodiment, the transplanted iMyoblasts repair the muscle injury.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" or "approximately" as used herein, in the context of any of any assay measurements refers to +/−5% of a given measurement.

The term "substitute for" as used herein, refers to the switching the administration of a first compound or drug to a subject for a second compound or drug to the subject.

The term "reserve cells" as used herein refers to a subpopulation of quiescent, undifferentiated cells (e.g., stem cells) resident in cultures of differentiated tissue that can be reactivated to proliferate in response to growth factor rich media. For example, differentiated muscle tissue contains reserve cells comprising a subpopulation of undifferentiated muscle stem cells.

The term "progenitor factors" as used herein refers to at least one compound that stimulates an induced pluripotent stem cell into an undifferentiated tissue stem cell.

The term "growth factors" as used herein refers to at least one compound that stimulates an undifferentiated tissue stem cell into an induced secondary tissue stem cell.

The term "transgene-free" or "gene-free" as used herein refers to a cell culture media without nucleic acids or polynucleotides that are capable of transfecting a cell for expression of exogenous proteins within the transfected cell.

The term "genetic identity" as used herein refers to a genome of a cell or stem cell that determines a tissue-specific differentiation. For example, a stem cell having a muscle cell genetic identity will differentiate into a somatic muscle cell (e.g., a striated somatic muscle cell). An "identical" genetic identity between two or more cells refers to an equivalent phenotypic endpoint of differentiation even though some differences may exist in genotype. A "stable" genetic identity refers to the maintenance of identical genetic identity over a prorogation period (e.g., ~30 cell population doubling division cycles).

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc.) to a binding partner under conditions such that the binding partner becomes unresponsive to its natural ligands. Inhibitory compounds may include, but are not limited to, small organic molecules, antibodies, and proteins/peptides.

The term "attached" as used herein, refers to any inter-action between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleo-tides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, trans-dermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "derived from" as used herein, refers to the source of a sample, a compound or a sequence. In one respect, a sample, a compound or a sequence may be derived from an organism or particular species. In another respect, a sample, a compound or sequence may be derived from a larger complex or sequence.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethyl-ene glycol, and the like), suitable mixtures thereof, and vegetable oils, coatings, isotonic and absorption delaying agents, liposome, commercially available cleansers, and the like. Supplementary bioactive ingredients also can be incor-porated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that all trace impurities have been removed.

As used herein, the term "substantially purified" refers to molecules, either nucleic or amino acid sequences, that are removed from their natural environment, isolated or sepa-rated, and are at least 60% free, preferably 75% free, and more preferably 90% free from other components with which they are naturally associated. An "isolated polynucle-otide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The term "portion" when used in reference to a nucleotide sequence refers to fragments of that nucleotide sequence. The fragments may range in size from 5 nucleotide residues to the entire nucleotide sequence minus one nucleic acid residue. When used in reference to an amino acid sequence refers to fragments of that amino acid sequence. The frag-ment may range in size from 2 amino acid residues to the entire amino acid sequence minus one amino acid residue.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unla-beled A) in a reaction containing labeled "A" and the antibody will reduce the amount of labeled A bound to the antibody.

The term "sample" or "biopsy" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

Low stringency conditions comprise conditions equiva-lent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1%

SDS, 5×Denhardt's reagent {50×Denhardt's contains per 500 ml: 5 g Ficoll (Type 400, Pharmacia), 5 g BSA (Fraction V; Sigma)} and 100 g/ml denatured salmon sperm DNA followed by washing in a solution comprising 5×SSPE, 0.1% SDS at 42° C. when a probe of about 500 nucleotides in length. is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., $C_0 t$ or $R_0 t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. As indicated by standard references, a simple estimate of the $T_m$ value may be calculated by the equation: $T_m = 81.5 + 0.41$ (% G+C), when a nucleic acid is in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction. Dieffenbach C. W. and G. S. Dveksler (1995) In: *PCR Primer, a Laboratory Manual*, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucle-otide. The primer must be sufficiently long to prime the synthesis of extension products in the presence of the inducing agent. The exact lengths of the primers will depend on many factors, including temperature, source of primer and the use of the method.

DNA molecules are said to have "5' ends" and "3' ends" because mononucleotides are reacted to make oligonucle-otides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucle-otide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer ele-ments can exert their effect even when located 3' of the promoter element and the coding region. Transcription ter-mination and polyadenylation signals are located 3' or downstream of the coding region.

As used herein, the term "gene" means the deoxyribo-nucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into hetero-geneous nuclear RNA (hnRNA); introns may contain regu-latory elements such as enhancers. Introns are removed or "spliced out" from the nuclear or primary transcript; introns therefore are absent in the messenger RNA (mRNA) tran-script. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcrip-tion, posttranscriptional cleavage and polyadenylation.

BRIEF DESCRIPTION OF THE FIGURES

Key to Nomenclature iMyoblasts (iMB) is interchangeable with induced Sec-ondary Myoblasts (iSM). (iMB are myoblasts derived by reserve cell selection from S3 differentiated muscle. cultures)

iMyotubes (iMT) are differentiated myotubes generated by culture of proliferating iMB in growth factor defi-cient differentiation medium.

bMyoblasts (bMB) is interchangeable with pMyo. (bMB are adult biopsy derived Myoblasts).

bMyotubes (bMT) are differentiated myotubes generated by culture of proliferating bMB in growth factor defi-cient differentiation medium.

bMesenchymal cells (bMes) is interchangeable with pMes. (bMes are CD56 negative non-myogenic cells selected by FAC sorting of cultures of adult muscle biopsies.

tMyoblasts (tMB) are tertiary myoblast lines generated by reserve cell selection of iMT cultures.

iMyocytes are S3 stage cultures produced by iPSC induc-tion using Myocea commercially available reagents, originally described by Caron et al, 2016.

Figure 1:
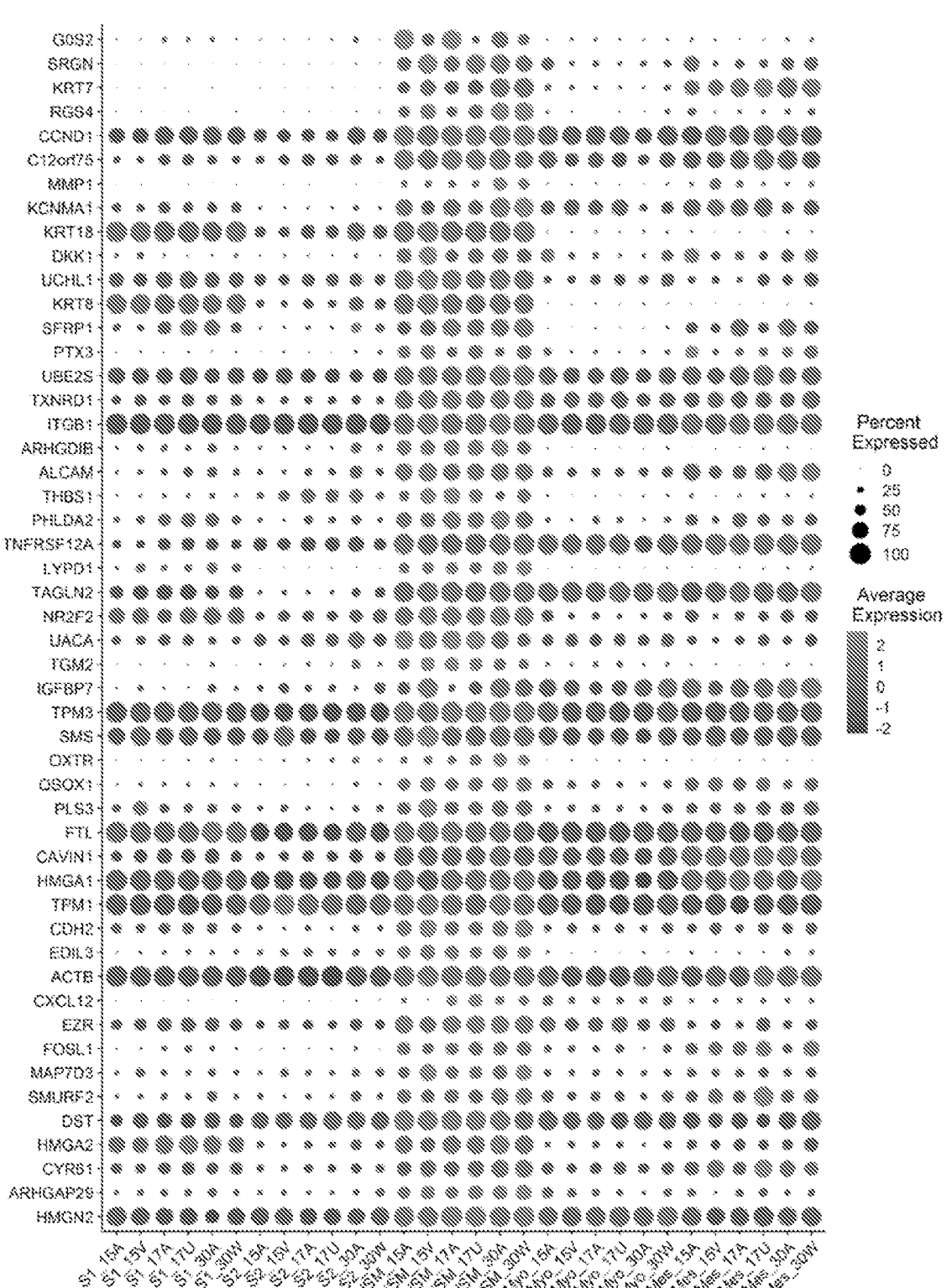
Figure 1:
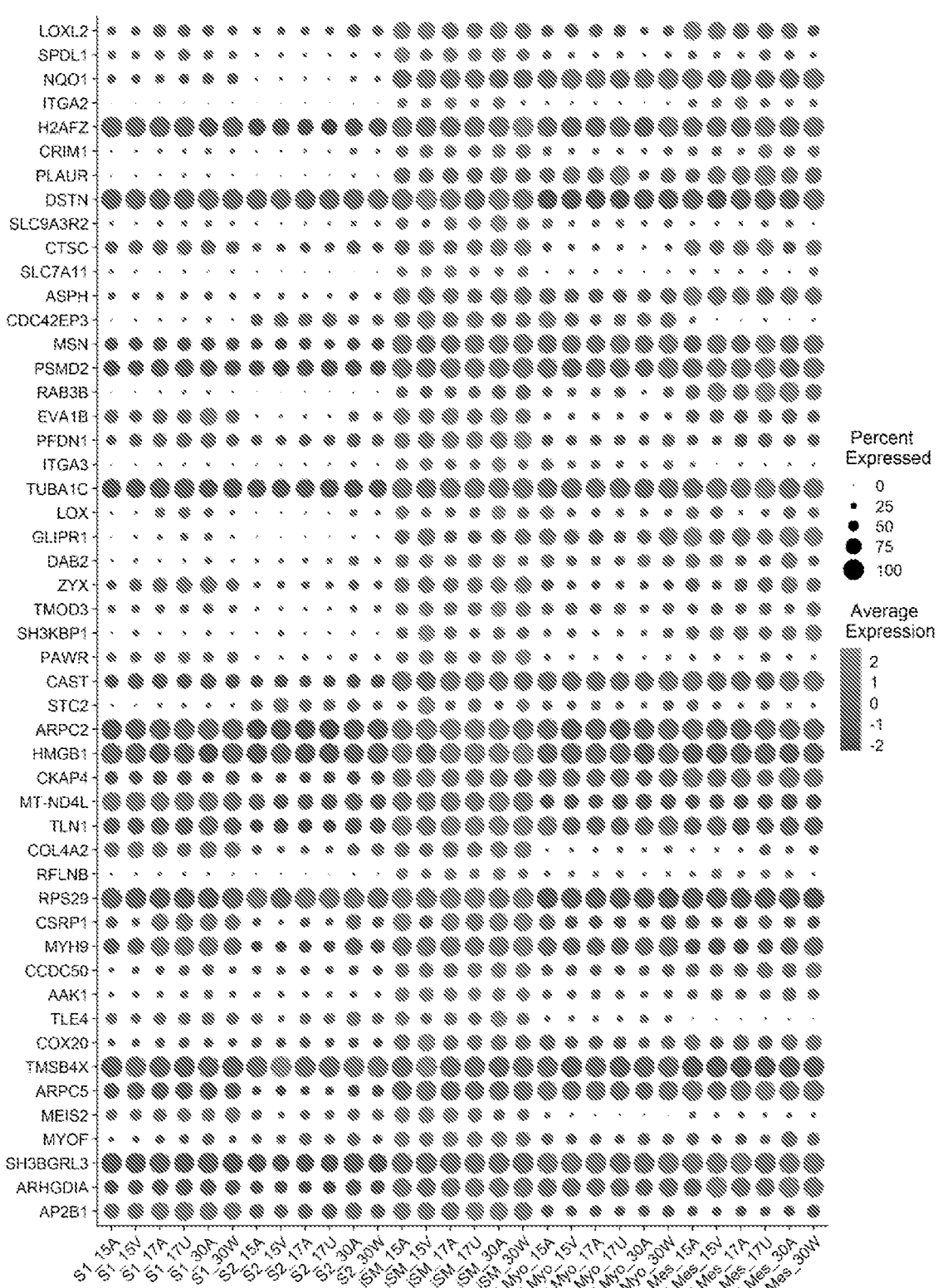
Figure 1:
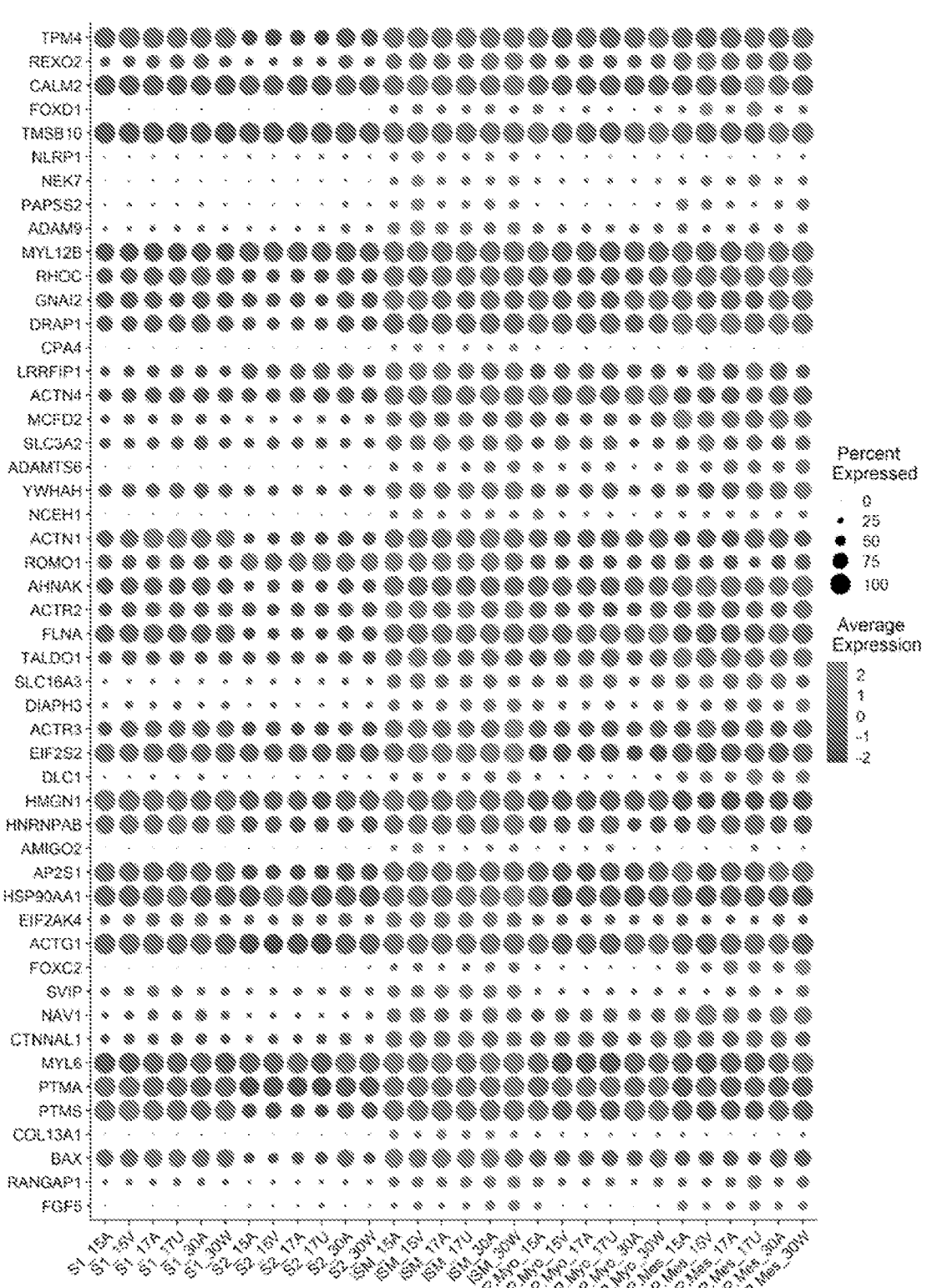
Figure 1:
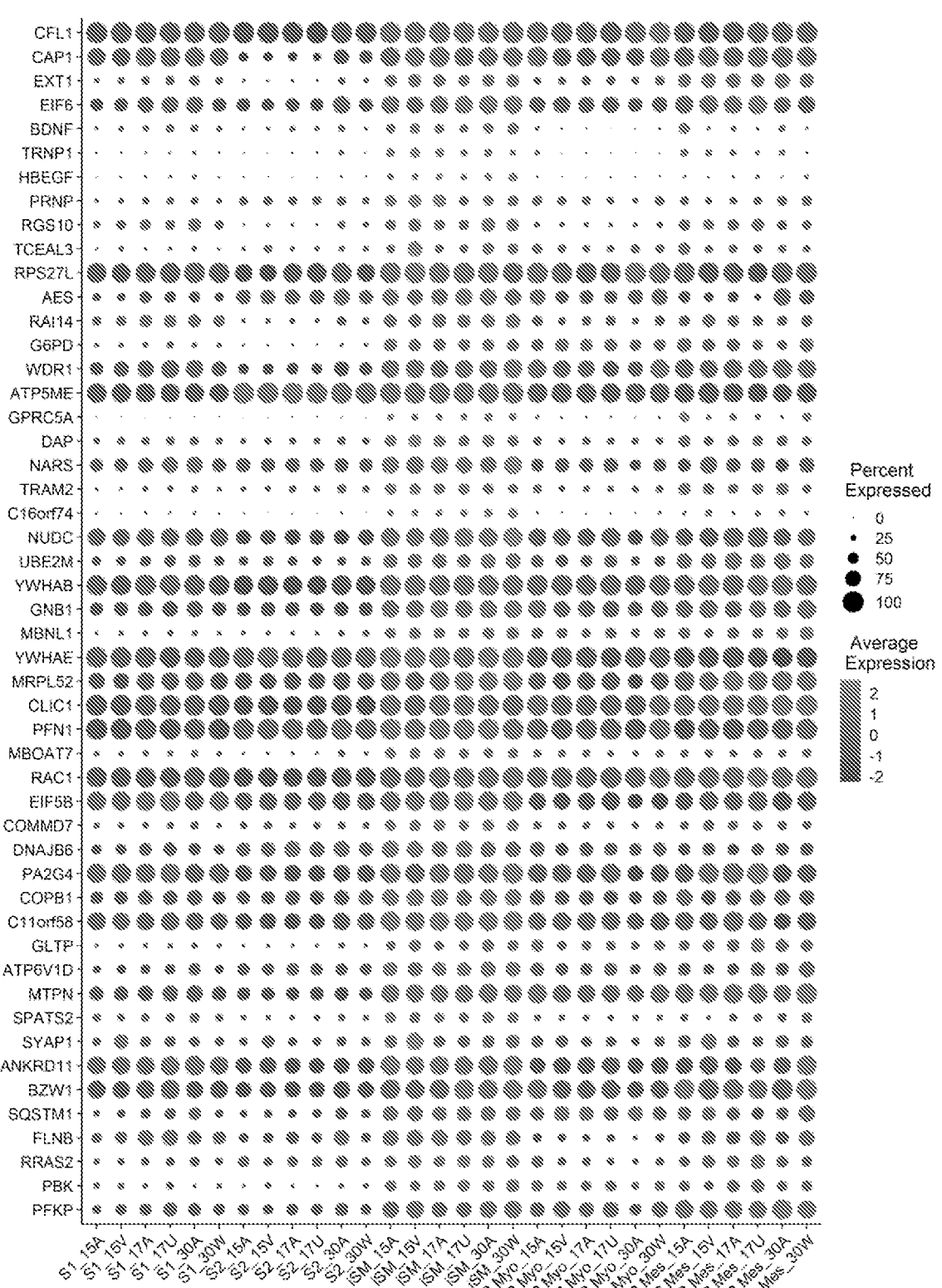

FIG. 1 present exemplary data showing that scRNASeq analysis revealed over two hundred (200) genes were dif-ferentially expressed in iMyoblasts. scRNASeq was per-formed with control and FSHD S1, S2, iMyoblasts and primary cells from muscle biopsies. The expression level of each differentially expressed gene in all cell lines is repre-sented by the color of the dot with red=high expression and blue=low expression compared to iMyoblasts. The size of each dot corresponds to the percentage of cells in each cell line that express the indicated differentially expressed gene. The larger dot corresponds to more cells in that cell line expressing the indicated gene.

Figure 2:
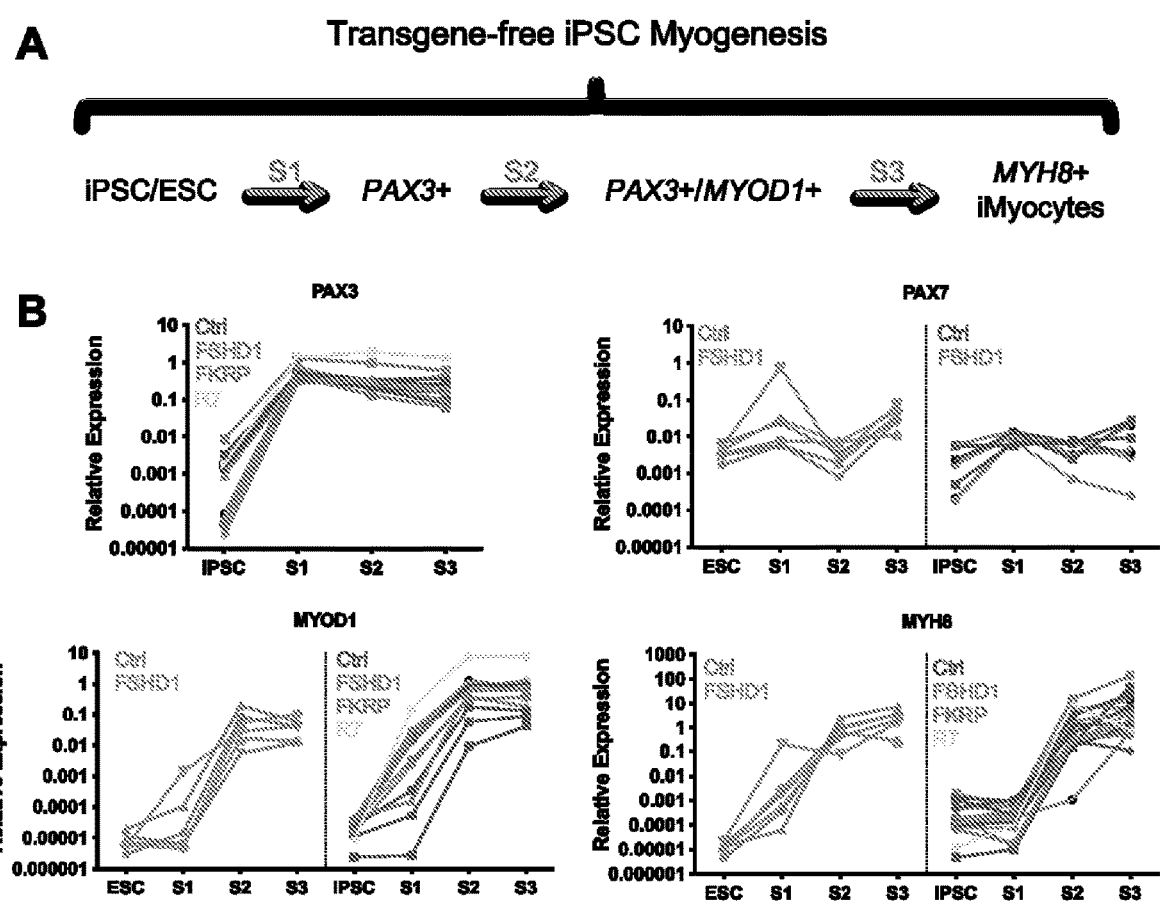

FIG. 2 presents exemplary data showing transgene-free myogenic induction of FSHD1 and healthy control iPSCs and ESCs. For ESC lines: Genea 002=filled, tip up triangle, Genea 015=filled, tip down triangle, Genea 019=filled, hexagon, Genea 049=open, tip up triangle, Genea 050=open, tip down triangle, Genea 096=open, hexagon. qPCR data are normalized to RPL13A RNA and relative expression is shown normalized to RPL13A for each sample. For B symbols: 17 cohort (17AM, 17UM)=circle, 15 cohort (15AM, 15VM)=square, 30 cohort=diamond. iPSCs reprogrammed from primary myoblasts have colored filled symbols. iPSCs reprogrammed from primary fibro-blasts have black filled symbols (15AF, 15VF and 17AF).

FIG. 2A: Schematic showing the three-stage transgene-free myogenic induction using commercially available reagents provided by Myocea Inc. Caron et al., (2016).

FIG. 2B: qPCR assays quantifying the expression of muscle master regulators (PAX3, PAX7) and muscle RNAs (MYOD1, MYH8) during a three-stage myogenic induction of FSHD ESCs (pink) and healthy control ESCs (teal), FSHD iPSCs (red) and healthy control iPSCs (blue), LGMDR7 (light green) and WWS (dark green).

Figure 3:
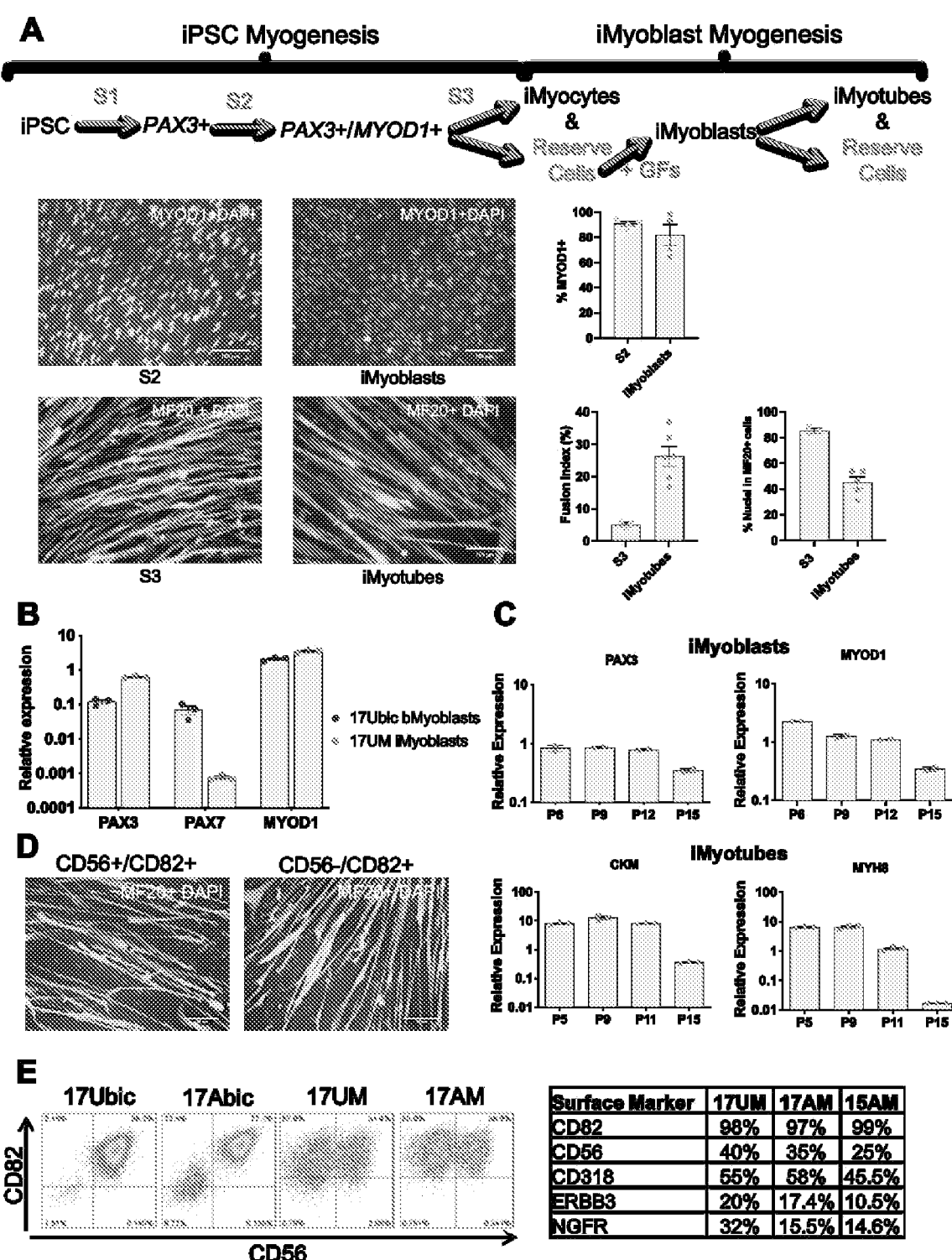

FIG. 3 presents exemplary data showing a characteriza-tion of iMyoblast muscle stem cells isolated by reserve cell selection.

FIG. 3A: Schematic of a three-stage iPSC induction and growth factor (GF) stimulation of differentiated S3 iMyo-cytes to isolate reserve cells under five percent (5%) oxygen to generate proliferative-iMyoblasts, and their differentia-tion induced by serum-free medium under twenty percent (20%) oxygen to generate iMyotubes and reserve cells. Images show S2 cells and iMyoblasts immunostained with MYOD1 antibody, and S3 cells and iMyotubes immunos-tained with MF20 myosin antibody. Nuclei are stained with DAPI. Scale bars=100 μm. Quantification of % MYOD1+S2 and iMyoblasts, fusion index and % nuclei in MF20+ cells are shown for S3 and iMyotubes are shown on the right.

FIG. 3B: qPCR assays comparing expression of muscle master regulatory gene (PAX3, PAX7, MYOD1 and MYF5) RNAs in biopsy myoblasts (17Ubic) and iMyoblasts (17UM). qPCR data are normalized to RPL13A RNA and relative expression is shown normalized to RPL13A.

FIG. 3C: qPCR assays using proliferating (top), or 7-day differentiated (bottom) healthy control 17UM iMyoblasts at increasing passage (P) numbers. qPCR data are normalized to RPL13A RNA and relative expression is shown normalized to RPL13A.

FIG. 3D: CD56$^+$/CD82$^+$ or CD56$^-$/CD82$^+$ from healthy control (17UM) iMyoblasts isolated by FACS were differentiated for 7 days and immunostained for MF20 myosin antibody. Scale bars=100 μm.

FIG. 3E: Flow cytometry using CD56 and CD82 cell surface markers expressed by biopsy myoblasts (17Ubic, 17Abic) and iMyoblast (17UM, 17AM) cell lines (left panel). Table summarizes iMyoblasts surface marker expression as assayed by flow cytometry (right panel).

Figure 4:
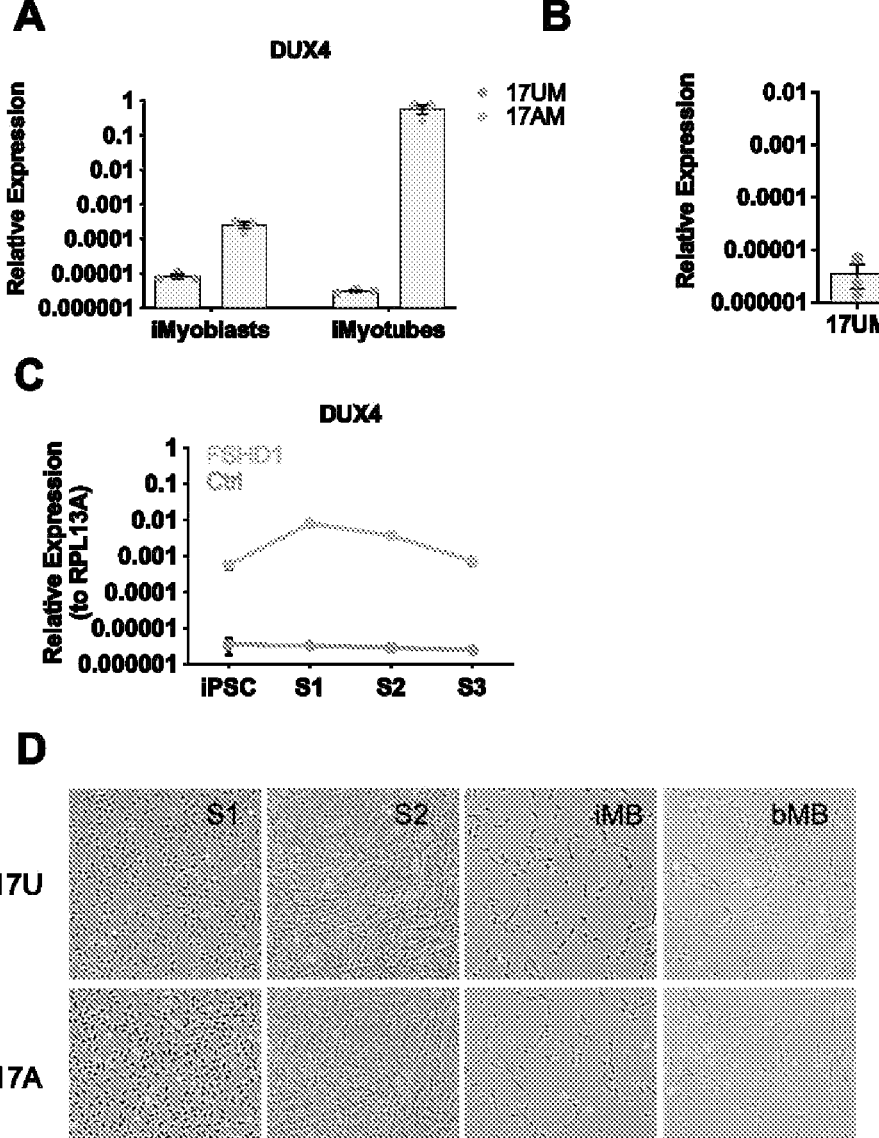

FIG. 4 presents exemplary data showing qPCR assays of DUX4 RNA in FSHD and control cell lines and cell morphology.

FIG. 4A: qPCR assays of DUX4 RNA expressed by healthy control (17UM) and FSHD (17AM) in proliferating iMyoblasts and in iMyotubes after seven days in serum-free Opti-MEM differentiation medium.

FIG. 4B: qPCR assays of DUX4 RNA expressed by healthy control (17UM and 15VM) and FSHD (17AM, 15AM) iPSC lines.

FIG. 4C: qPCR assays of DUX4 RNA expressed by healthy control (17UM) and FSHD (17AM) during the three stages of iPSC transgene free induction.

FIG. 4D: Phase images of S1, S2, iMyoblasts and adult biopsy myoblasts from family cohort 17. Scale bar=100 μm.

Figure 5:
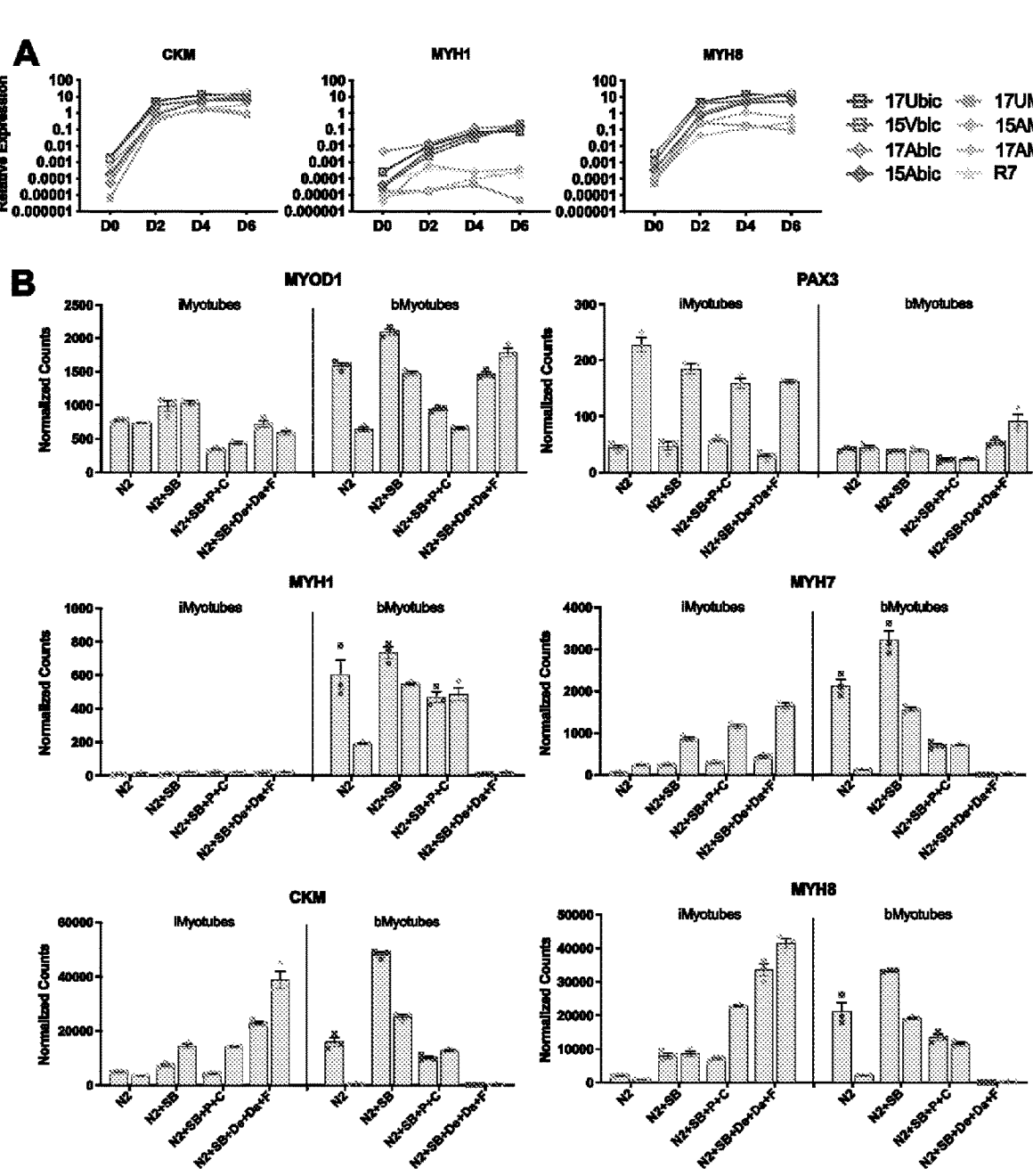

FIG. 5 presents exemplary data showing the kinetics of upregulation for muscle differentiation genes during myotube differentiation of FSHD and healthy control iMyoblasts and FSHD primary myoblasts and data showing the response of iMT and bMT to different differentiation media.

FIG. 5A: qPCR assays of Muscle differentiation RNAs. qPCR data are normalized to RPL13A RNA and relative expression is shown normalized to RPL13A.

FIG. 5B: NanoString digital RNA assays compared the expression of muscle differentiation RNA expression in FSHD1 and Ctrl iMyotubes and bMyotubes of cohort 17 in response to N2 serum-free culture medium and N2 medium supplemented with TGFβ inhibitor SB431542 (N2+SB), N2 medium supplemented with (SB), corticosteroid Prednisolone (P), and a GSK3 inhibitor/Wnt signaling activator, CHIR99021 (C) (N2+SB+P+C), and N2 medium supplemented with (SB), the corticosteroid Dexamethasone (De), α gamma-Secretase/Notch signaling inhibitor DAPT (Da), and an adenyl cyclase activator Forskolin (F) (N2+SB+De+Da+F). NanoString digital counts were normalized to RPL13A and shown on a linear scale. Each dot corresponds to an individual culture. Data are presented as mean±SEM for each condition.

Figure 6:
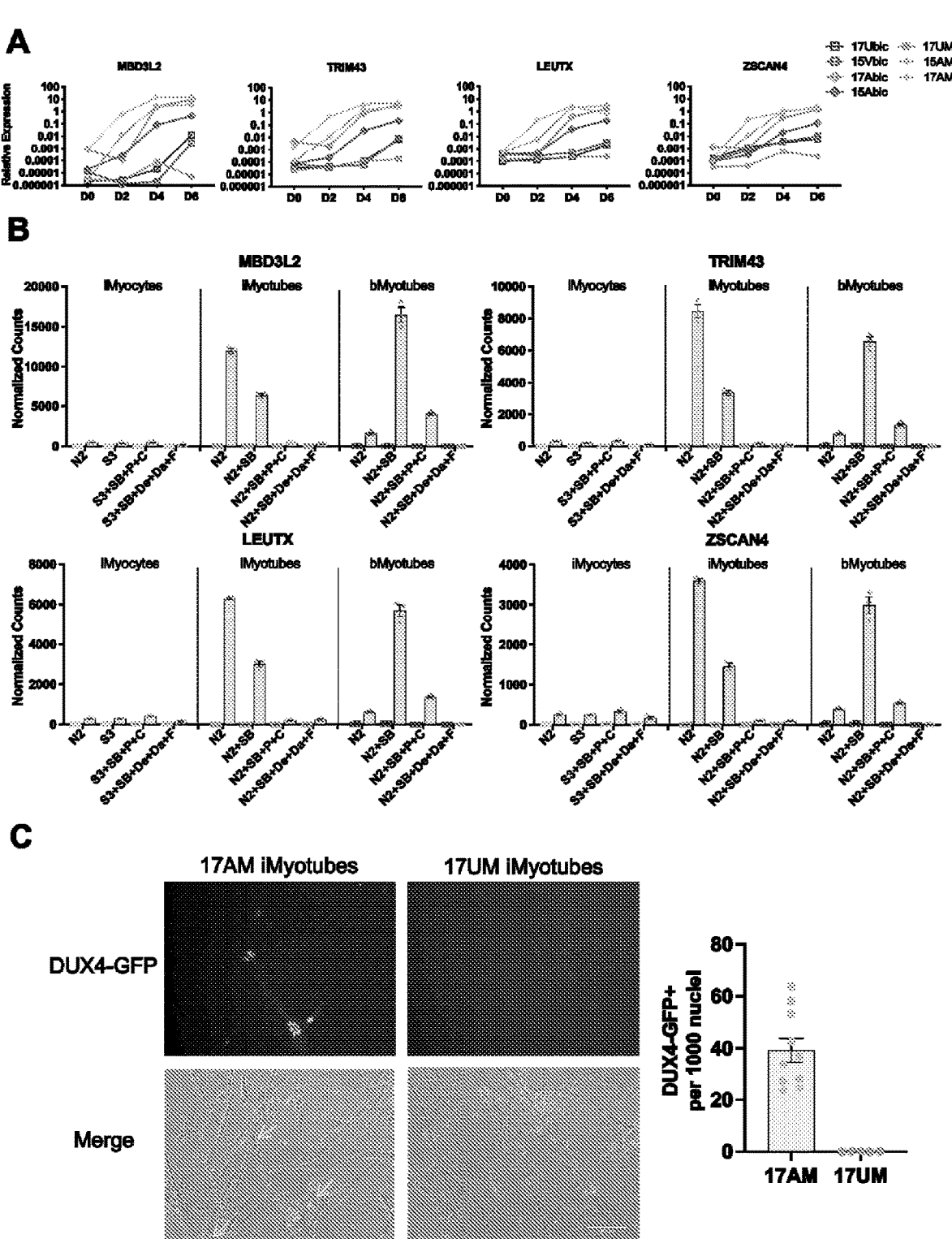

FIG. 6 presents exemplary data showing the kinetics of upregulation for DUX4 target genes during myotube differentiation of FSHD and healthy control iMyoblasts and FSHD primary myoblasts.

FIG. 6A: qPCR assays of DUX4 target gene RNA (MBD3L2, TRIM43, LEUTX, ZSCAN4) and muscle differentiation RNA (CKM, MYH1, MYH8) in cultures of primary myoblasts and iMyoblasts from family cohorts 17 in response to N2 serum free differentiation medium. qPCR data are normalized to RPL13A RNA and relative expression is shown normalized to RPL13A.

FIG. 6B: NanoString digital RNA assays compared the expression of DUX4 target gene RNA expression in FSHD1 and Ctrl S3 myocytes, iMyotubes and bMyotubes of cohort 17 in response to N2 serum-free culture medium and N2 medium supplemented with TGFβ inhibitor SB431542 (N2+SB), N2 medium supplemented with (SB), corticosteroid Prednisolone (P), and a GSK3 inhibitor/Wnt signaling activator, CHIR99021 (C) (N2+SB+P+C), and N2 medium supplemented with (SB), the corticosteroid Dexamethasone (De), α gamma-Secretase/Notch signaling inhibitor DAPT (Da), and an adenyl cyclase activator Forskolin (F) (N2+SB+De+Da+F). NanoString digital counts were normalized to RPL13A and shown on a linear scale. Each dot corresponds to an individual culture. Data are presented as mean±SEM for each condition.

FIG. 6C: DUX4-GFP reporter expression in FSHD iMyotubes (17AM) and healthy control iMyotubes (17UM) after Day 7 in differentiation medium. Scale bar=100 μm. Quantification of DUX4$^+$ nuclei per 1000 nuclei for each condition is shown on the right.

Figure 7:
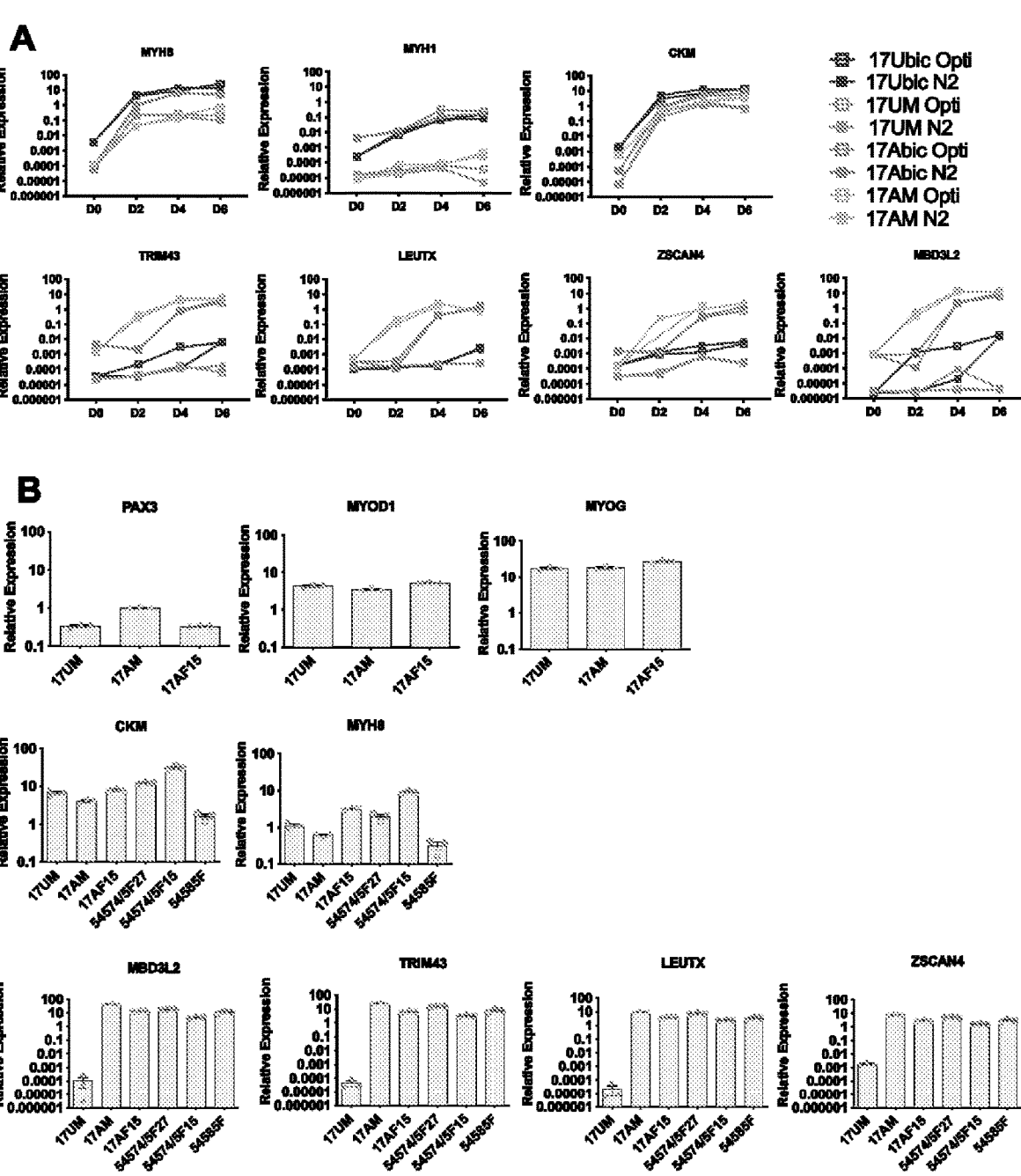

FIG. 7 presents exemplary data of muscle and DUX4 target gene expression in iMyoblast and bMyoblasts.

FIG. 7A: Normalized qPCR assays of the expression of muscle and DUX4 target genes during the myotube differentiation of FSHD1 and Ctrl bMyoblasts and iMyoblasts at Days 0, 2, 4 and 6, comparing Opti-MEM and N2 serum free differentiation media. The N2 results are also shown in FIGS. 5A and 6A.

FIG. 7B: qPCR assays comparing muscle protein and DUX4 target gene RNAs from differentiated FSHD and Ctrl iMyotubes generated from iPSCs derived by reprogramming CD56+ muscle biopsy bMyoblasts (17UM, 17AM), CD56− muscle biopsy fibroblasts (17AF15), and skin fibroblasts (54574/5F, 54585F). qPCR data are normalized to RPL13A RNA and relative expression is shown normalized to RPL13A.

Figure 8:
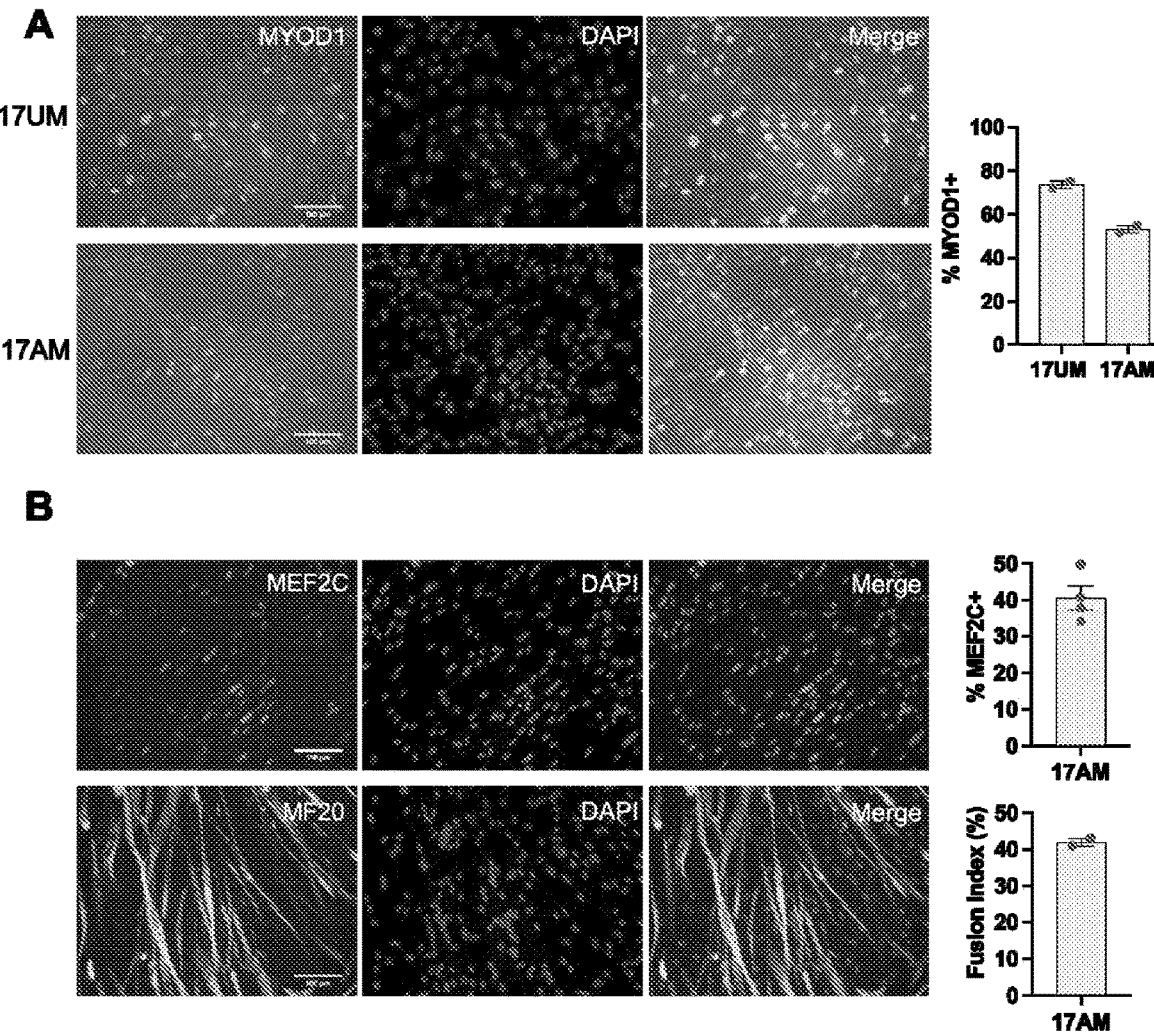

FIG. 8 presents exemplary data showing isolation of induced tertiary myoblasts from differentiated iMyotubes cultures. Scale bars=100 μm.

FIG. 8A: Healthy control (17UM) and FSHD (17AM) iTM cell lines isolated from iMyotubes cultures using reserve cell selection and maintained for three passages in myoblast growth medium followed by Immunostaining with MYOD1 antibody. Quantification of % MYOD1+ cells is shown on the right.

FIG. 8B: FSHD (17AM) iTM myotube cultures after 4 days in N2 serum-free differentiation medium and immunostained with MEF2C (muscle transcription factor) and MF20 antibodies. Quantification of % MEF2C+ cells and fusion index is shown on the right.

Figure 9:
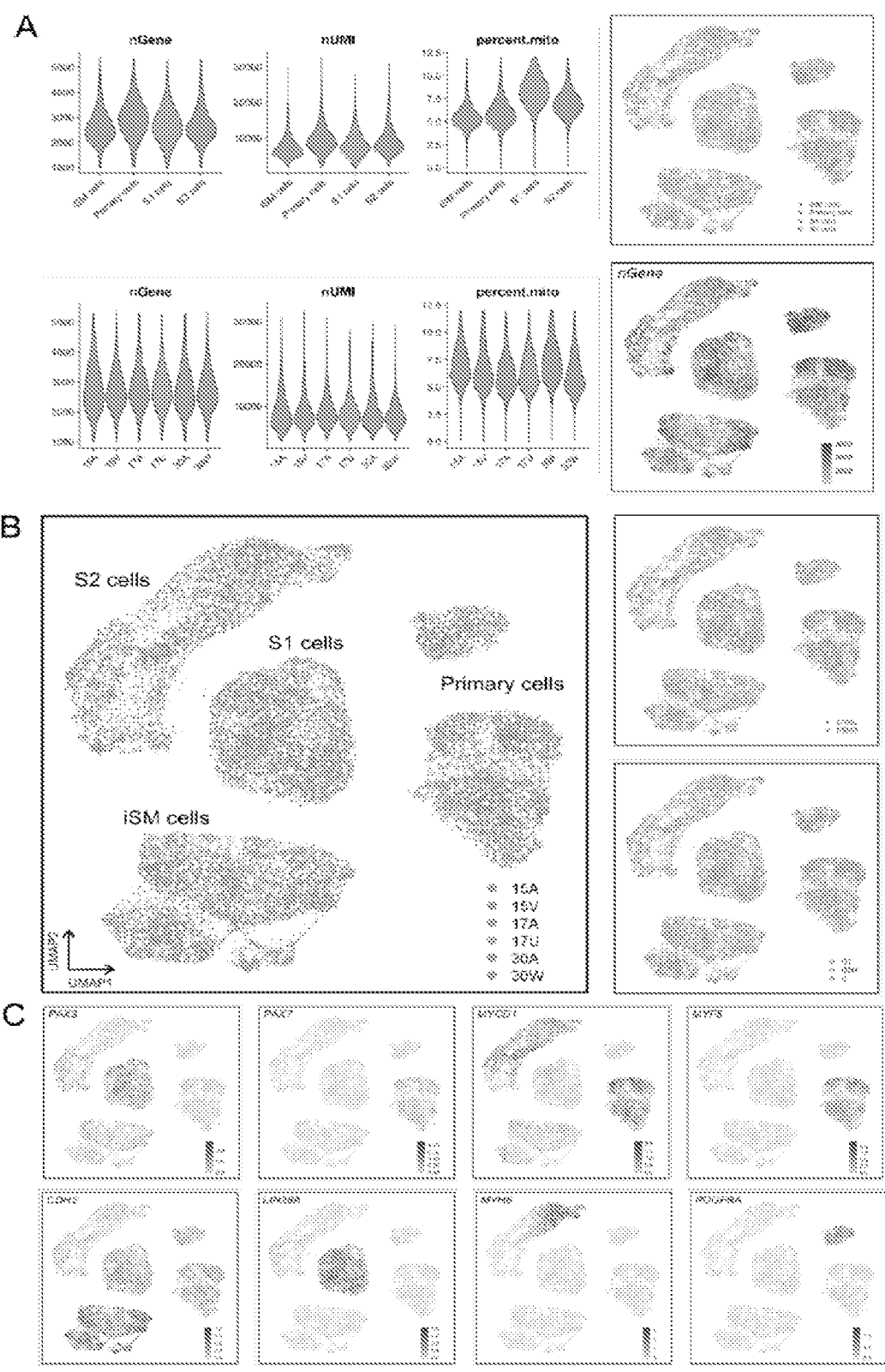

FIG. 9 presents exemplary data showing that single cell RNAseq shows that iMyoblasts are unique myogenic cells.

FIG. 9A: The median number of genes detected per cell (nGene), the median nUMI and the proportion of total reads from mitochondrial genes (generally <6%, a higher fraction suggests cell damage) are shown.

FIG. 9B: iPSC-derived S1 cells, induced primary myoblasts S2, iMyoblasts and the primary cells from biceps muscle biopsies segregate into distinct clusters upon analysis. Cell cycle gene signatures were used to estimate cell cycle state.

FIG. 9C: Differential expression of representative marker genes, including PAX3, PAX7, MYOD1, MYF5, CDH2, LIN28A, MYH8 and PDGFR, among S1, S2, iMyoblasts and muscle biopsy-derived cells.

Figure 10:
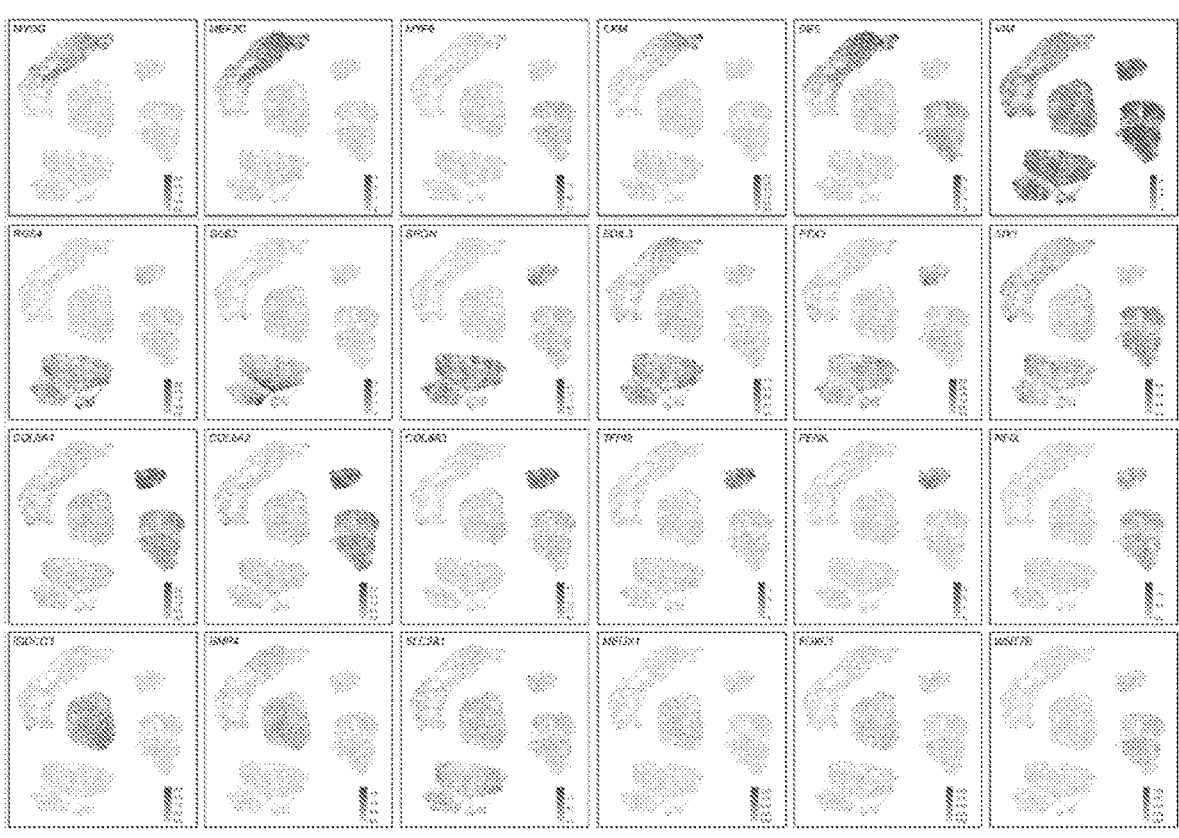

FIG. 10 presents exemplary data showing a UMAP analysis of gene expression in FSHD and healthy control S1 and S2 cells, and proliferating iMyoblasts and biopsy muscle cells.

Figure 11:
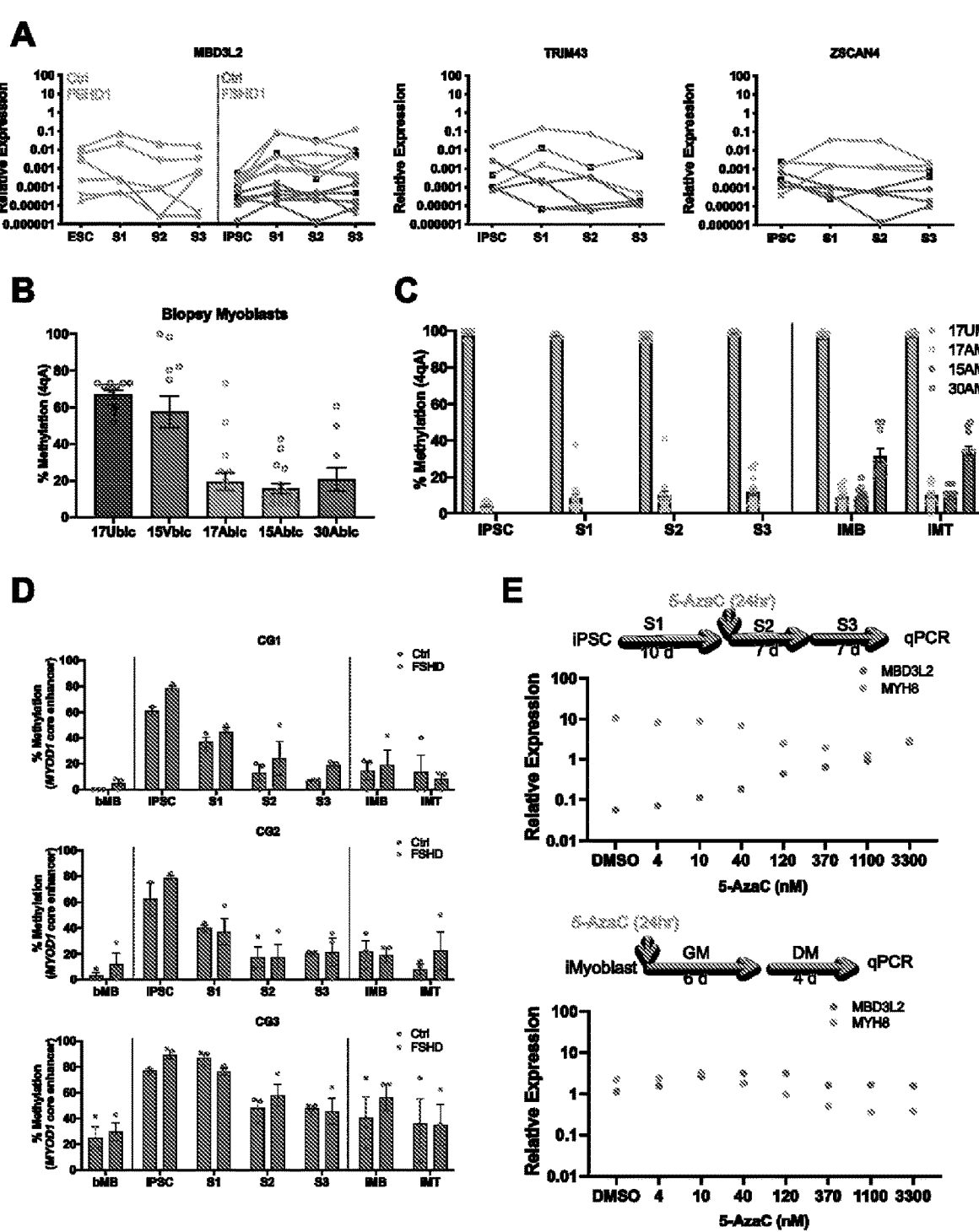

FIG. 11 presents exemplary data showing epigenetic regulation of DUX4 and MYOD1 CpG methylation during iPSC reprogramming and differentiation. Data for all experiments are presented as mean±SEM.

FIG. 11A: qPCR assays quantifying the expression of DUX4 target genes (MBD3L2, TRIM43, ZSCAN4) during a three-stage myogenic induction of FSHD ESCs (pink) and healthy control ESCs (teal), FSHD iPSCs (red) and healthy control iPSCs (blue). qPCR data are normalized to RPL13A RNA and relative expression is shown normalized to RPL13A for each sample.

FIG. 11B: Bisulfite sequencing of the DUX4 4qA DNA from primary myoblasts of healthy control subjects (17Ubic, 15Vbic) and FSHD subjects (15Abic, 17Abic, 30Abic), shown as the percent of 4qA CpG sites methylated. Each dot corresponds to the % CpG methylation of an individual sequenced DNA clone.

FIG. 11C: Bisulfite sequencing of DUX4 4qA alleles of iPSCs reprogrammed from parental primary myoblasts of a healthy control subject (17UM) and FSHD subjects (17AM, 15AM, 30AM), showing percentages of CpG methylation of DUX4 4qA alleles in iPSC cell lines, in iPSC induced cells at the S1, S2 and S3 stages of primary myogenic induction, and in iMyoblast cell lines derived from these iPSC lines during proliferation and differentiation.

FIG. 11D: Bisulfite sequencing of MYOD1 Core Enhancer, showing the percent methylation of the three MYOD1 core enhancer CpG sites (CG1, CG2, CG3) from parental biopsy myoblasts (15Abic, 17Abic, 30Abic, 15Vbic, 17Ubic, 30Wbic), reprogrammed iPSCs, iPSC cells at S1, S2 and S3 stages of myogenic induction and iMyoblast cell lines (15AM, 17AM, 30AM, 15VM, 17UM, 30WM) derived from these iPSC lines during proliferation and differentiation. Each dot corresponds to the average methylation of 10 DNA clones for each cell stage.

FIG. 11E: qPCR assays of the expression of DUX4 target gene (MBD3L2) RNA and a muscle gene (MYH8) RNA of S2 cells (top panel) and iMyoblasts (bottom panel) following 24 hr treatment with increasing doses of 5-AzaC. 5-AzaC-treated S2 cultures were cultured for 6 days of S2 growth medium (GM) and 7 days in S3 differentiation medium (DM). 5-AzaC-treated iMyoblasts were cultured for 6 days in myoblast growth medium (GM) and 4 days in Opti-MEM differentiation medium. qPCR data were normalized to RPL13A and relative expression is shown normalized to RPL13A for each sample.

Figure 12:
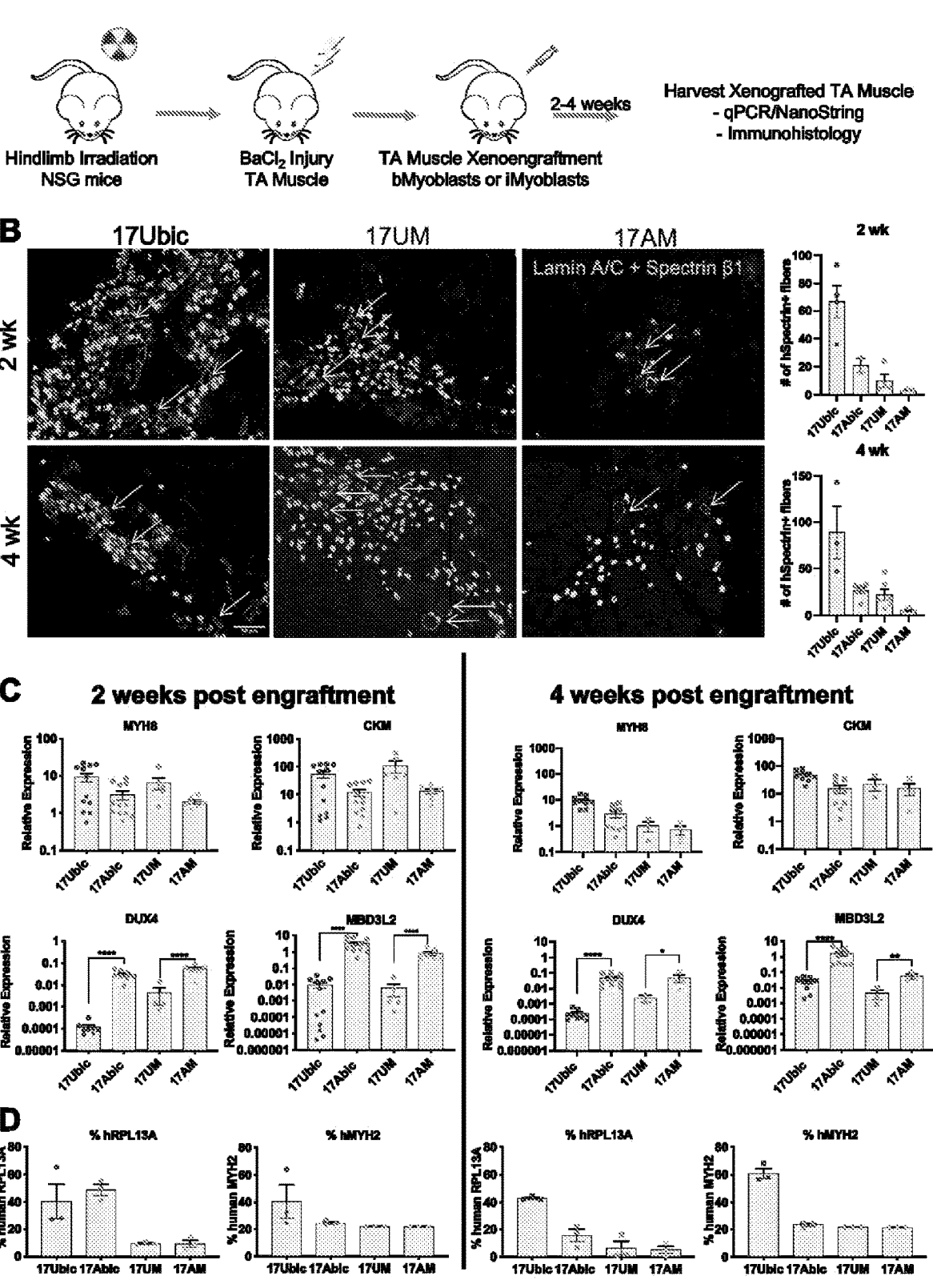

FIG. 12 presents exemplary data showing TA muscle xenografts of FSHD1 and healthy control iMyoblasts and biopsy myoblasts.

FIG. 12A: Representative schematic of iMyoblast and primary myoblast muscle xenograft protocol. TA muscles of NSG mice were xenoengrafted with 1×10⁶ cells of FSHD and healthy control primary myoblasts (17Ubic and 17Abic) and FSHD and healthy control iMyoblasts (17UM and 17AM). Xenografted TA muscles were isolated after 2 and 4 weeks for RNA isolation and qPCR RNA expression analysis using human-specific primers or for cryosectioning for immunofluorescence assays using human-specific antibodies.

FIG. 12B: Representative cryosections from humanized TA xenograft muscles were immunostained with human-specific lamin A/C to identify human nuclei and human-specific spectrin-β1, to identify human muscle fibers in 2- and 4-week-old xenografts. White arrows highlight human spectrin+fibers. Scale bar=50 μm. Quantification of spectrin+fibers for each engraftment condition is shown on the right.

FIG. 12C: qPCR assays of the expression of DUX4, DUX4 biomarker MBD3L2 and muscle genes (MYH8 and CKM) RNAs. qPCR assays were normalized to RPL13A and relative expression is shown normalized to RPL13A for each sample. Each dot corresponds to an RNA from one xenografted mouse TA, and data are presented as mean±SEM for each xenoengraftment condition. *=P<0.05, =P<0.01, **=P<0.0001 by Student's t-test.

FIG. 12D: NanoString digital RNA assays quantifying the percent human RPL13A and MYH2 in 2 (left) and 4 (right) week xenografts.

Figure 13:
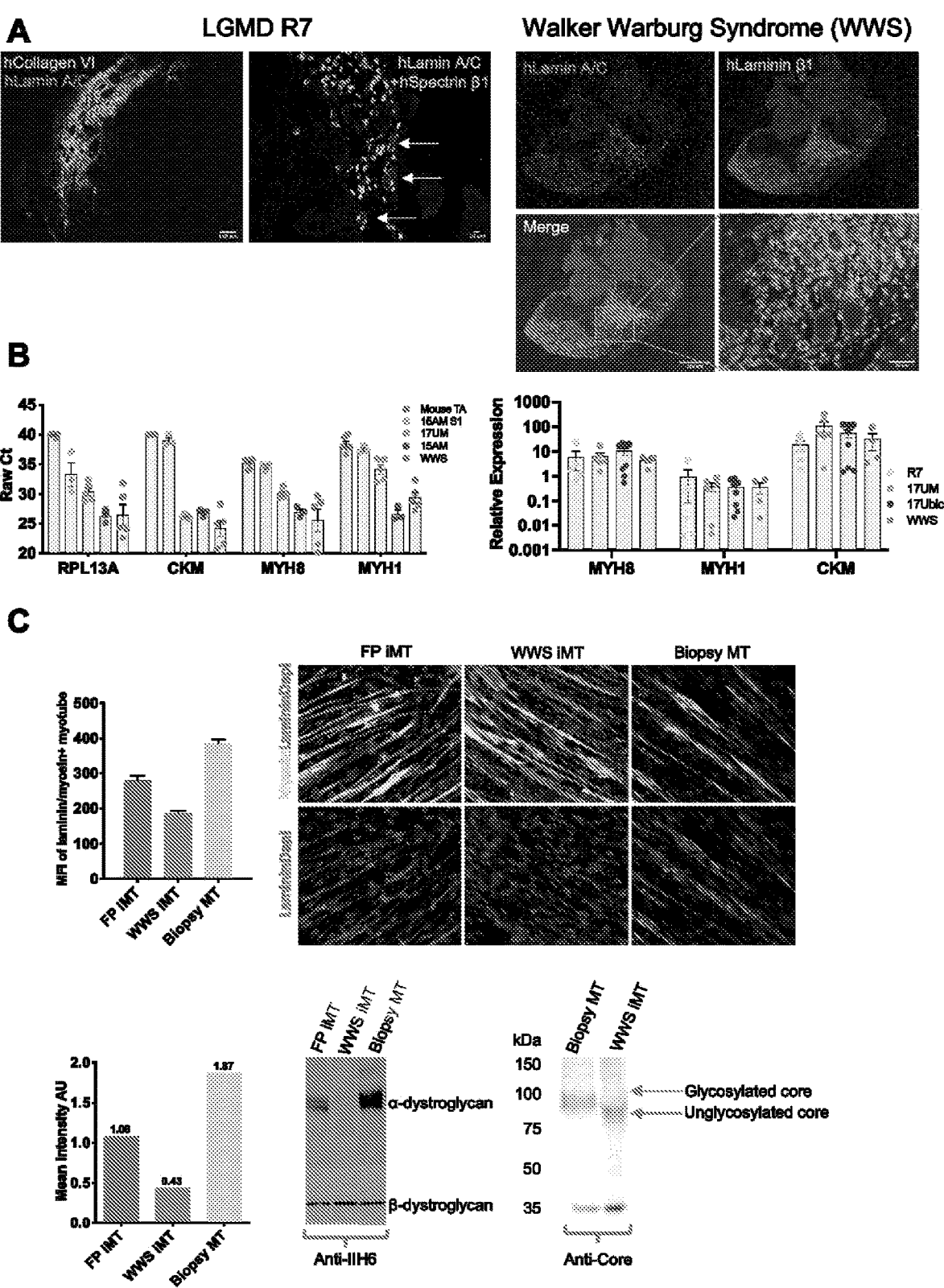

FIG. 13 presents exemplary data modeling LGMDR7 and WWS using iMyoblasts and healthy control iMyoblasts ex vivo and TA muscle xenografts.

FIG. 13A: (left) Representative images from LGMD R7 muscle xenograft cryosections immunostained with (left) human Lamin A/C (red) and human Collagen VI (green) or (C) human Lamin A/C and Spectrin β1 (green). Scale bars=150 μm and 10 μm respectively. Arrows identify spectrin+fibers. (right) Representative images of cryosections of WWS iMyoblast engrafted TA xenograft muscles immunostained with human Lamin A/C and human Laminin β1. Scale bar=250 μm.

FIG. 13B: (left) Raw Ct values comparing the engraftment and differentiation of cells to Ctrl, FSHD1 and WWS iMyoblasts and control unengrafted mouse TA using human specific housekeeping RNA RPL13A and muscle RNAs (CKM, MYH8 and MYH1). (right) Normalized qPCR assays of the expression of muscle differentiation genes 3 weeks after engraftment of bMyoblasts (17Ubic) or iMyoblasts (17UM, LGMDR7, WWS). Each dot corresponds to RNA from one xenografted mouse TA. Data are presented as mean±SEM for each xenoengraftment condition.

FIG. 13C: (top) Representative images from bMyotube or FKRP disease iMyotube cultures (FP iMT and WWS iMT) immunostained with Laminin (red) and myosin antibodies, and Dapi to stain nuclei (blue). The mean fluorescent intensity (MFI) averaged from multiple fields of view for each condition is shown on the left. Data are presented as mean±SD for each condition. (bottom) Western blot assays showing expression of α-dystroglycan and β-dystroglycan in biopsy MT, WWS and FP iMyotubes (iMT) using glycosylation-specific IIH6 antibody. Mean intensity of IIH6 α-dystroglycan for each condition is shown on the left. (right) Western blot assay of the core dystroglycan protein expressed by biopsy MT, WWS and FP iMyotubes (iMT) using Core protein antibody.

Figure 14:
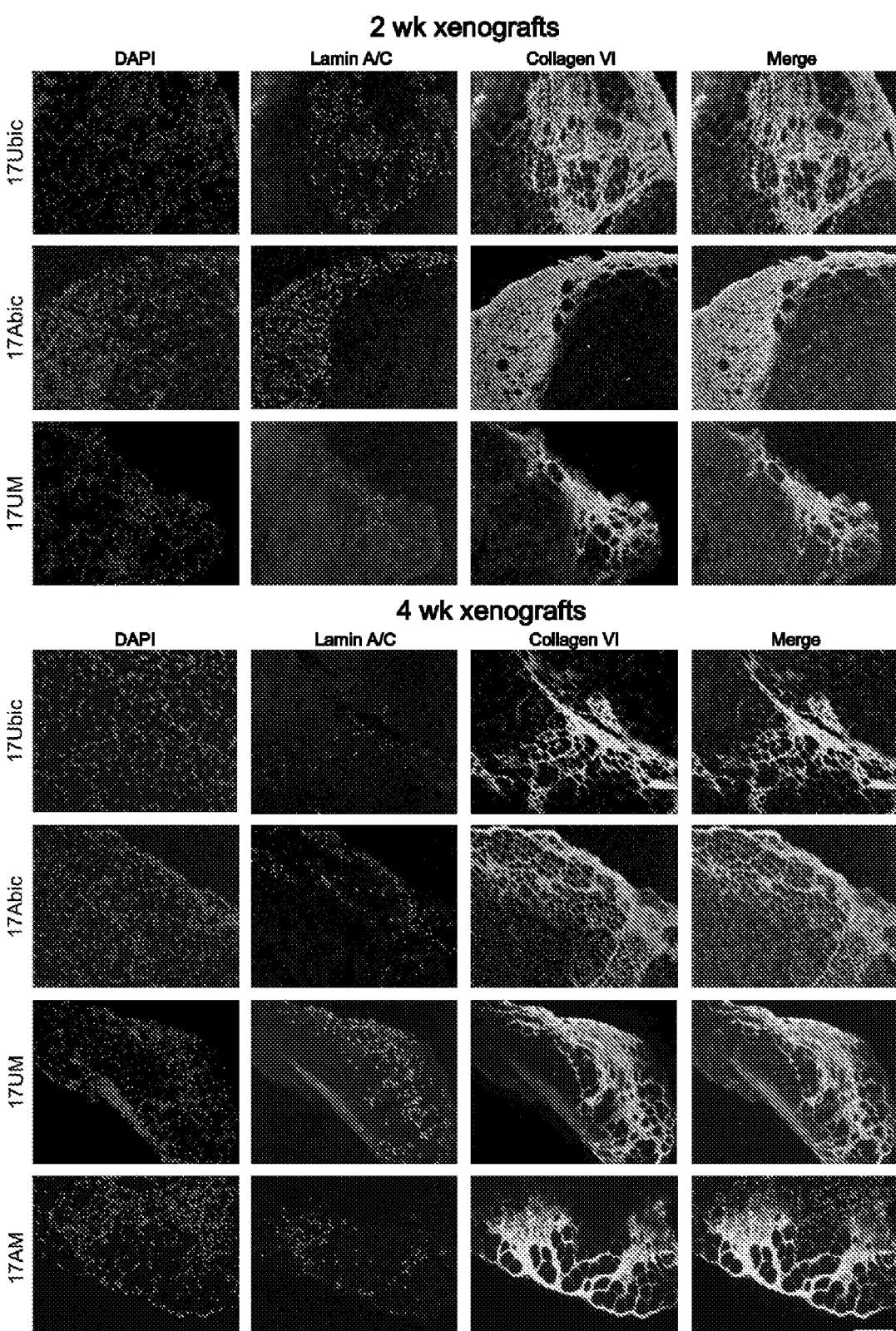

FIG. 14 presents exemplary data showing that biopsy myoblast and iMyoblasts efficiently engraft into irradiated and injured immune deficient mice. Cryosections of TA muscles xenoengrafted with of healthy control (17Ubic) and FSHD (17Abic) primary myoblasts and healthy control (17UM) and FSHD (17AM) iMyoblasts s were immunostained with human specific lamin A/C and collagen VI antibodies 2 wk (top panels) and 4 wk (bottom panels) after muscle xenoengraftment. Scale bar=150 μm.

Figure 15:
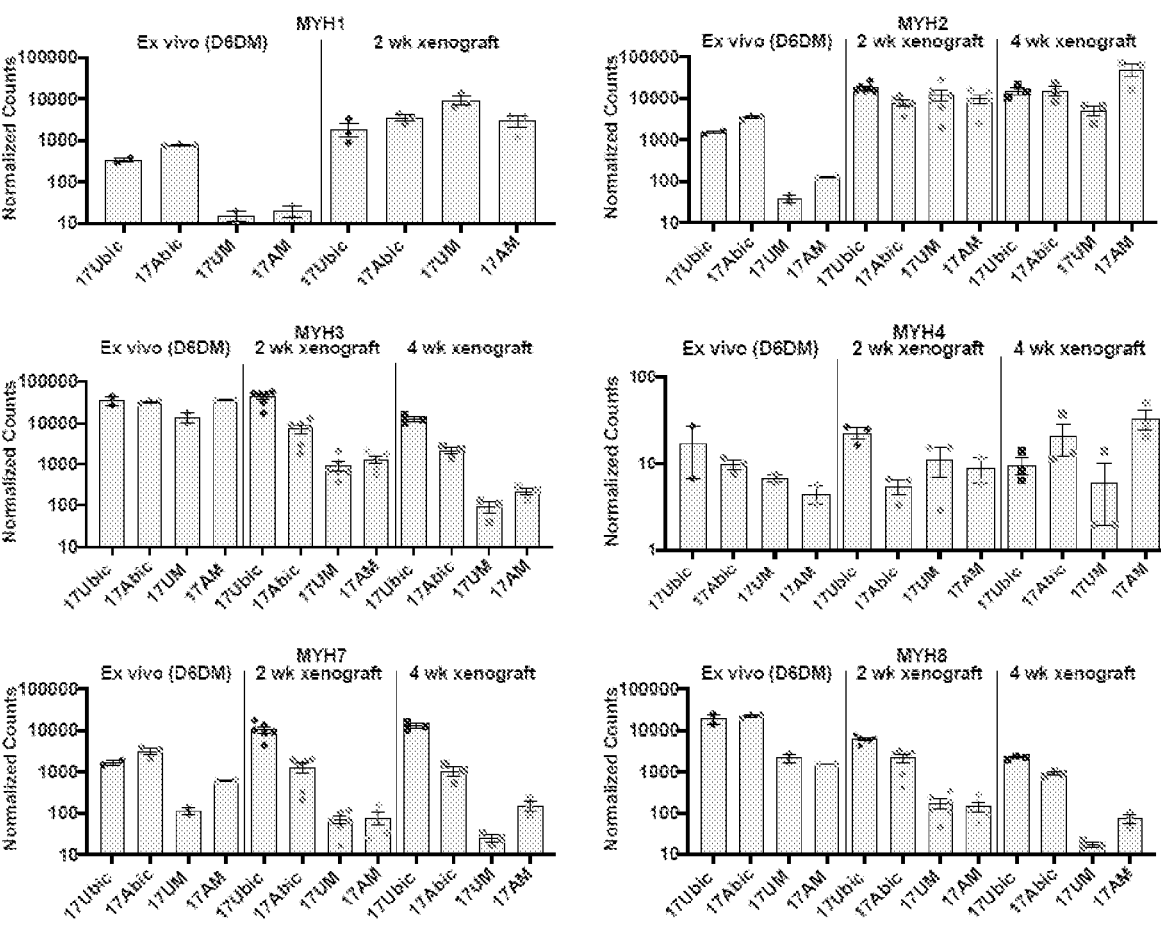

FIG. 15 presents exemplary data showing embryonic/adult myosin isoform switching during maturation of iMyoblast and biopsy myoblast muscle xenografts. RNA expression analyses of myotube cultures of FSHD (17Abic) and healthy control (17Ubic) primary myoblasts and FSHD (17AM) and healthy control (17UM) iMyoblasts after 6 days of differentiation in Opti-MEM (D6DM), and 2- and 4-week muscle xenografts generated by engraftment of these FSHD and healthy control primary myoblasts and FSHD and healthy control iMyoblasts. RNA expression was assayed using a custom NanoString panel of human-specific probes to muscle protein and regulatory gene RNAs, normalized to a panel of human housekeeping genes. Digital reads of RNAs normalized to human-specific housekeeping genes are plotted on a log scale, where each dot corresponds to RNA from one xenoengrafted mouse TA muscle (2 wk and 4 wk xenograft) or one ex vivo myotube culture; data are presented as mean±SEM for each cell or xenograft sample.

Figure 16:
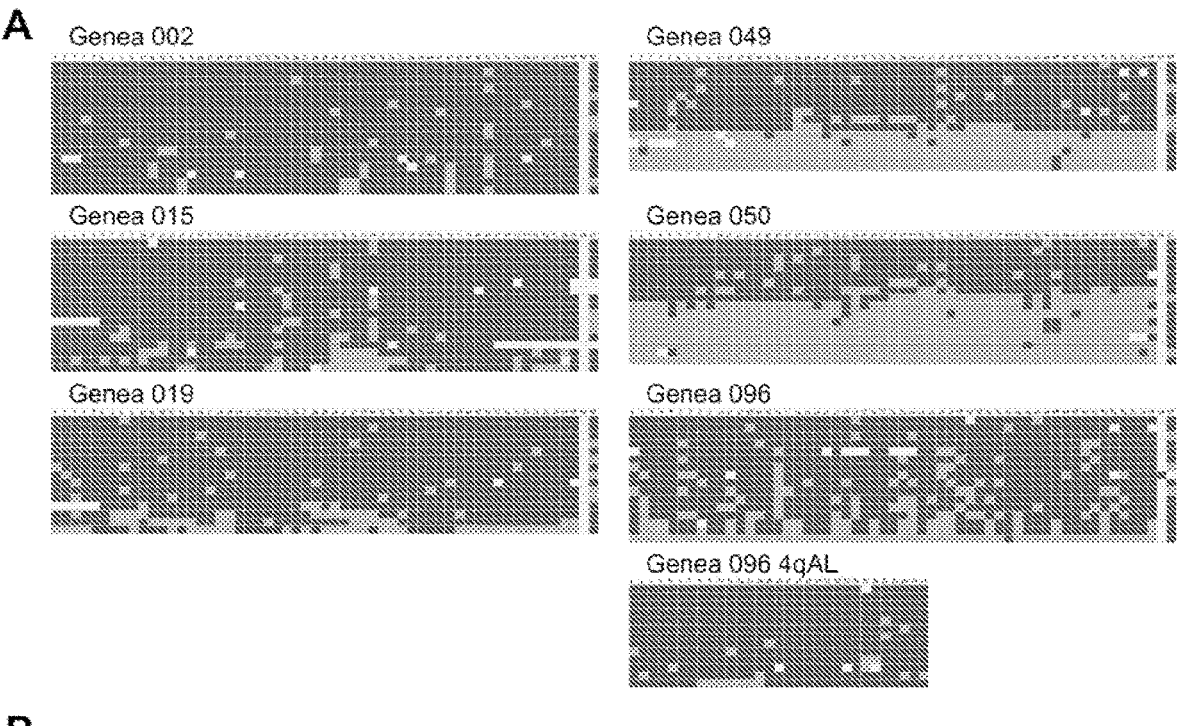
Figure 16:
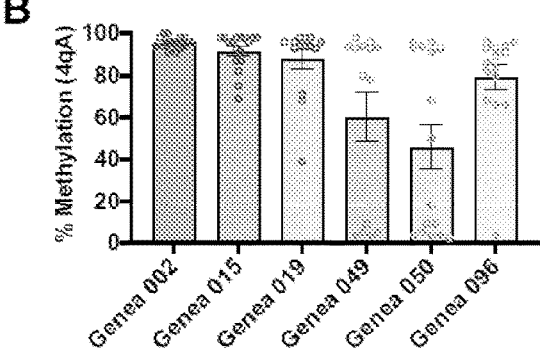

FIG. 16 presents exemplary data showing CpG methylation of the 4qA allele of FSHD or control ESCs. Bisulfite sequencing of the DUX4 4qA allele of Genea Biocells healthy control and FSHD ESCs.

FIG. 16A: Bisulfite sequencing showing CpG methylated (red) or unmethylated (blue) CpG sites in DNA molecules amplified from DUX4 4qA allele. Each row represents CpG sites along a DNA clone.4qAL methylation is also shown for Genea 096.

FIG. 16B: Graphical representation of the data in FIG. 16A where each dot represents the % CpG methylation for one individual DNA clone. Blue are healthy control ESC and orange are FSHD. Data are shown as mean±SEM for each cell line.

Figure 17:
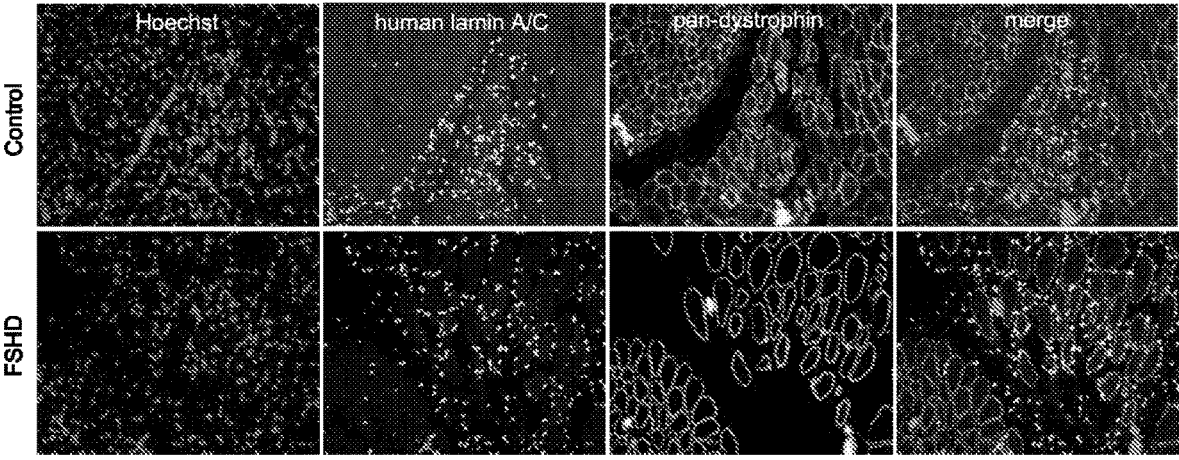

FIG. 17 presents exemplary data showing long-term maintenance of iMyoblast xenografts. Control or FSHD iMyoblasts were xenoengrafted into hindlimb irradiated and barium chloride injured TA muscles of immune deficient NSG mice. After 40 weeks of engraftment, TA muscles were cryosectioned and stained with human specific lamin A/C to show nuclei and dystrophin which shows human and mouse muscle fibers.

Figure 18:
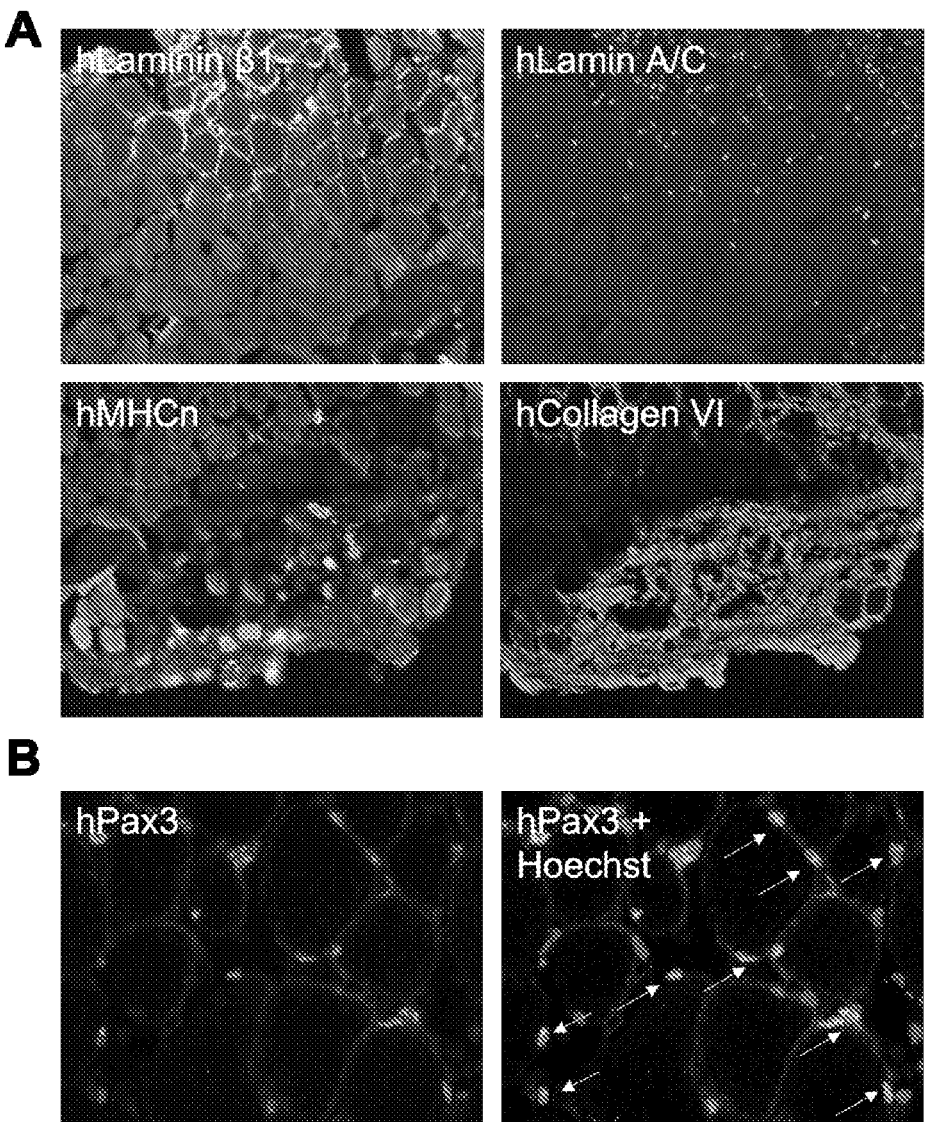

FIG. 18 presents exemplary data showing that iMyoblast cells can regenerate in response to injury in vivo.

FIG. 18A: WWS iMyoblast were xenoengrafted into hindlimb irradiated and barium chloride injured TA muscles of NSG mice. 5 weeks post engraftment, TA muscles were injured with barium chloride and allowed to recover for 3 weeks. TA muscles were isolated, cryosectioned and immunostained with human specific antibodies. (top) Serial sections immunostained for human laminin β1 (green) and human lamin A/C (red). (bottom) Serial sections were immunostained with human neonatal myosin heavy chain (green) and human collagen VI.

FIG. 18B: WWS iMyoblast were xenoengrafted into hindlimb irradiated and barium chloride injured TA muscles of NSG mice. 2 weeks post engraftment, TA muscles were injured with barium chloride and allowed to recover for 2 weeks. TA muscles were isolated, cryosectioned and immunostained with human specific Pax3 antibody.

Figure 19:
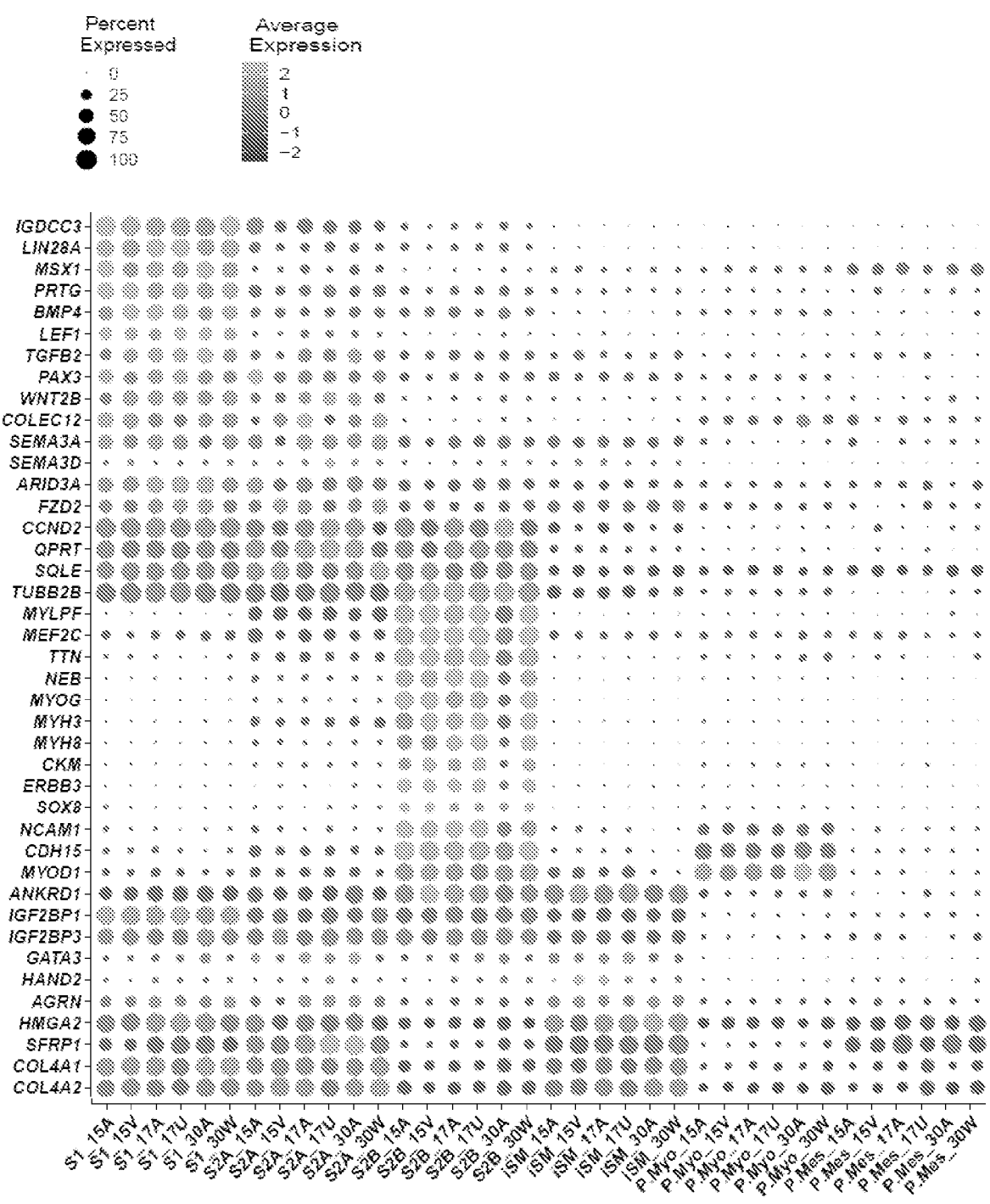
Figure 19:
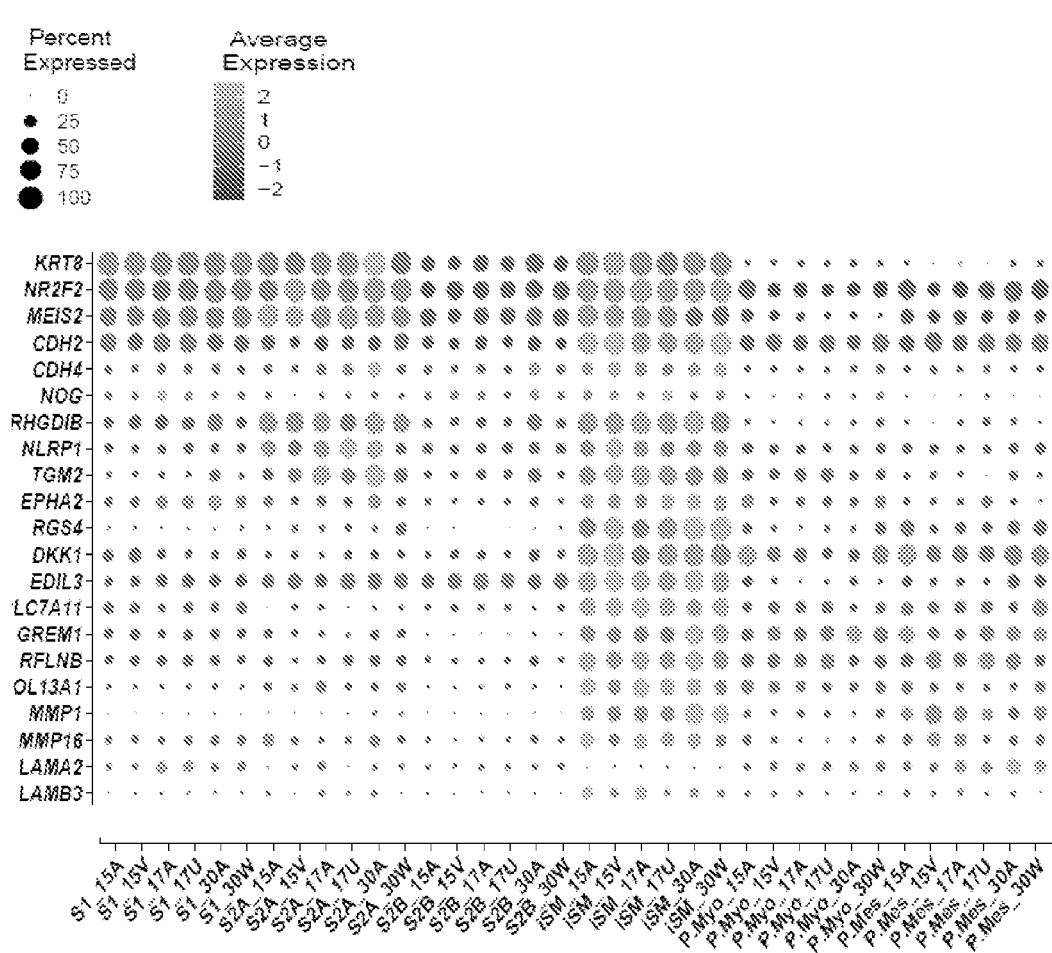
Figure 19:
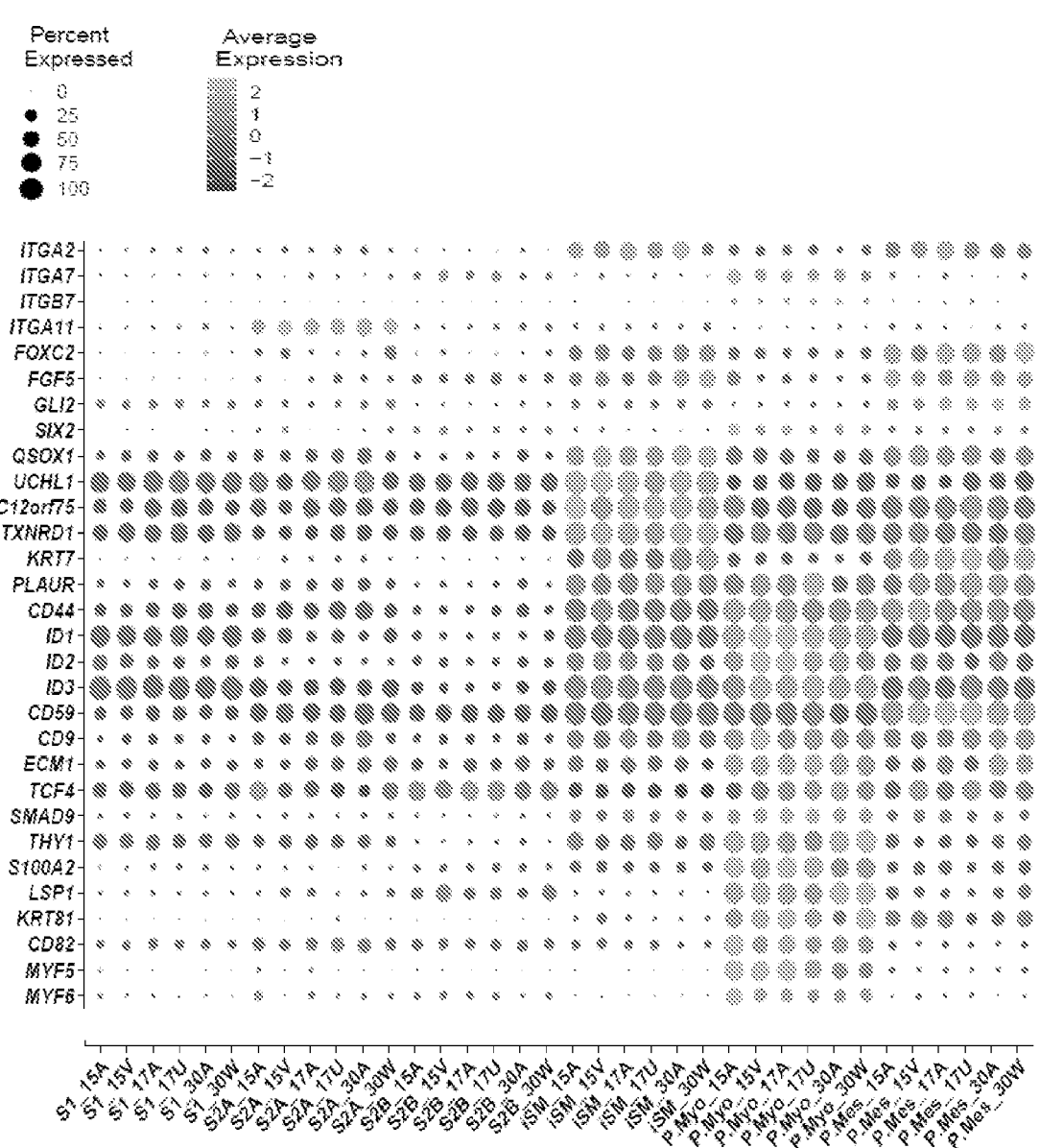
Figure 19:
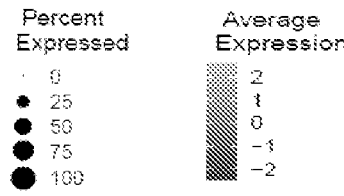
Figure 19:
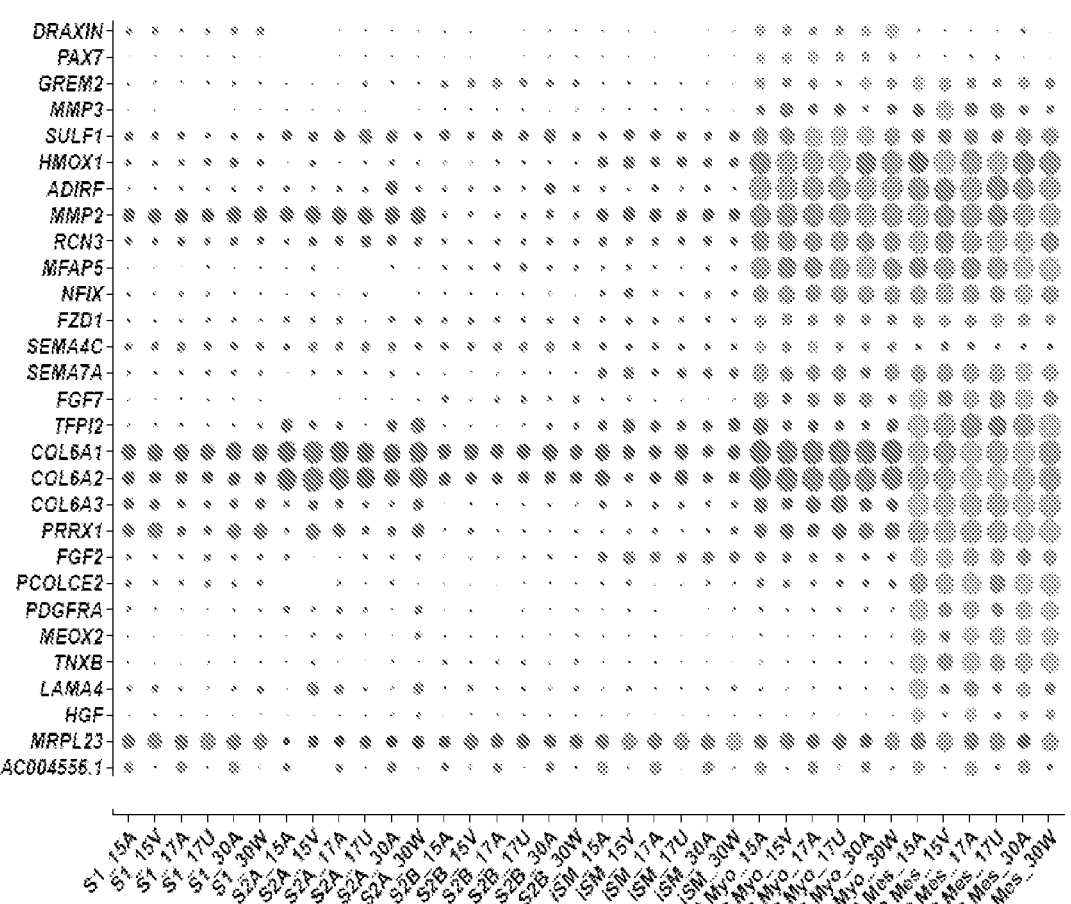

FIG. 19 presents exemplary data shows a representative scRNA-seq transcriptome signature of iMyoblast from FSHD1 and Ctrl subjects differs from gene expression in S1 and S2 iPM and P. Myo. The dot plot highlights selected genes that were differentially expressed between cell types. Colors indicate the average expression level of each gene (row) in each c cell group (column), with rows centered to have mean=0 and scaled to have SD=1; Positive values indicate up-regulation and negative values indicate down-regulation as compared to the average expression level across all cell groups. Sizes indicate the fraction of cells in which the gene was detected.

Figure 20:
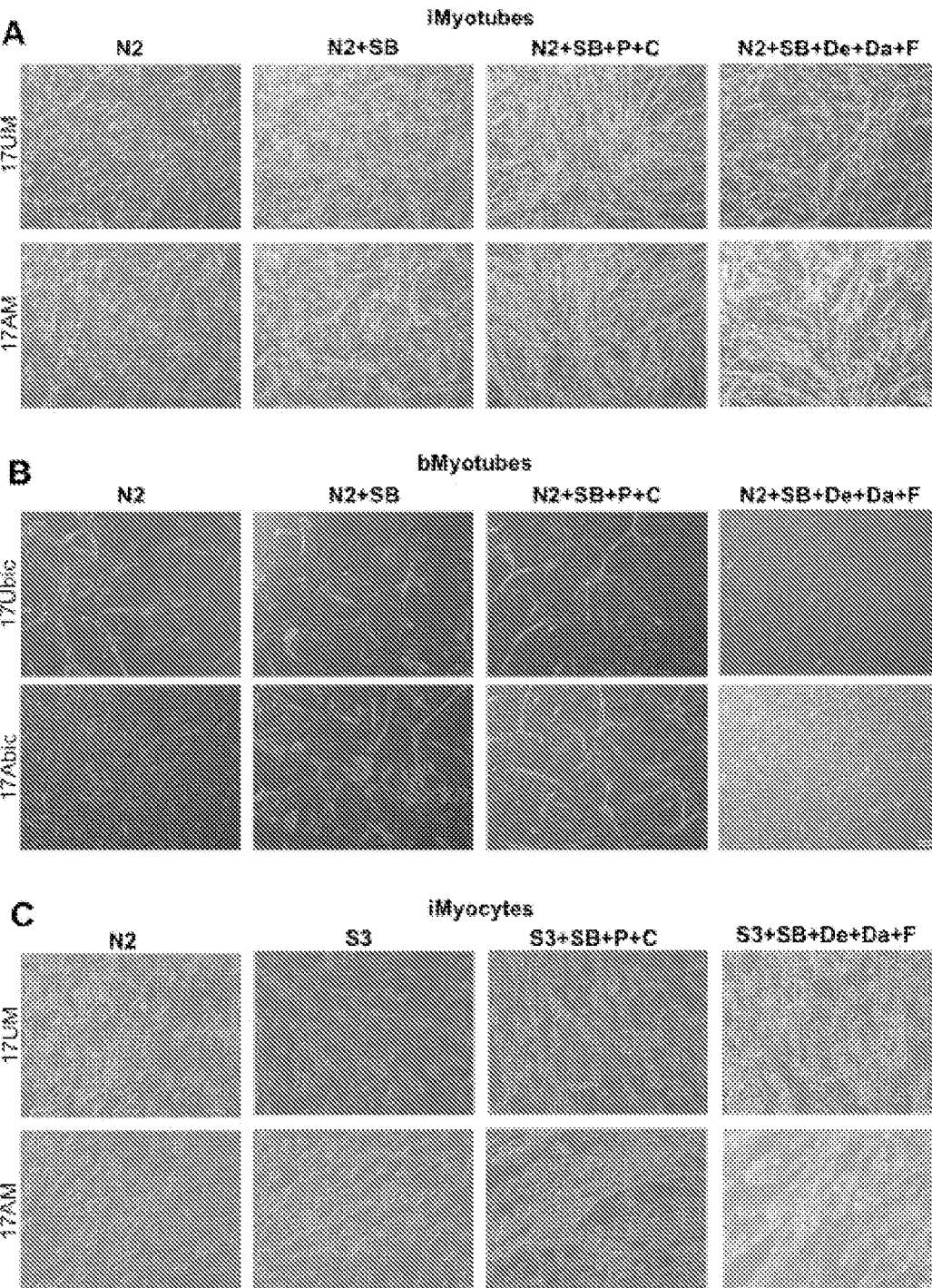

FIG. 20 presents exemplary data showing iMyotubes, bMyotubes and iMyocytes differentiation differences with designated differentiation media cocktails as disclosed herein; presented as phase images of Ctrl and FSHD1. Scale bar=250 μm (A and B), 100 m (C).

FIG. 20A: iMyotubes.

FIG. 20B: bMyotubes.

FIG. 20C: iMyocytes.

Figure 21:
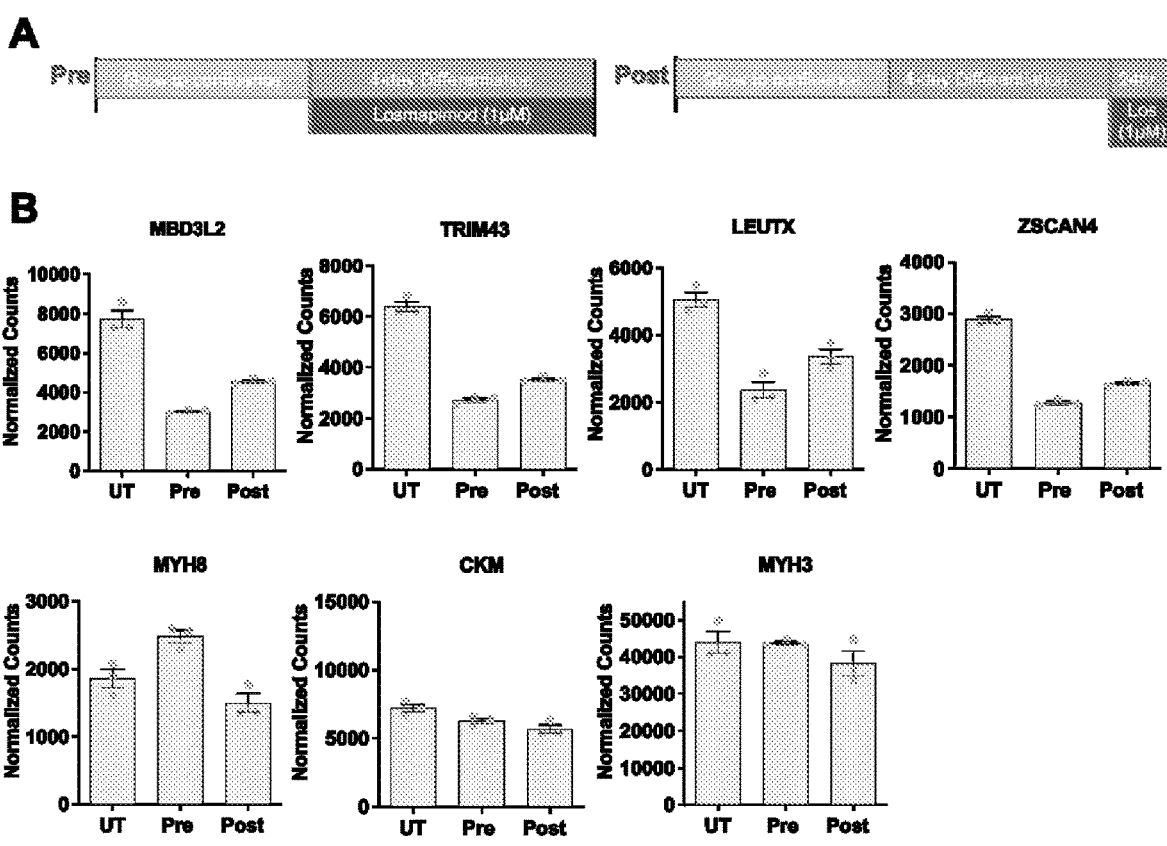

FIG. 21 presents exemplary data showing that Losmapimod treatment decreases DUX4 target gene expression in FSHD1 iMyotubes.

FIG. 21A: Schematic of Losmapimod treatment protocols for Pre-drug administration at the initiation of iMyotube differentiation and at Post iMyotube differentiation after 4 days in N2 differentiation medium.

FIG. 21B: NanoString digital RNA assays of DUX4 target gene and muscle gene expression in carrier treated (UT) FSHID1 iMyoblasts and in iMyotube cultures Pre- or Post-differentiation treatment with 1 M Losmapimod. Normalized counts of expression are presented on linear scale with each dot corresponding to an individual culture. Data are presented as mean±SEM for each condition.

DETAILED DESCRIPTION OF THE INVENTION

The present invention is related to the field of stem cell therapeutics. In particular, a method to generate large numbers of human muscle stem cell lines, iMyoblasts, from normal and patient derived iPSCs. Such a method provides human iMyoblasts as useful for ex vivo muscle differentiation and in vivo muscle engraftment therapeutics. Further, the methods provide for the efficient isolation and expansion of iPSCs into human skeletal muscle stem cells for muscle disease modeling, gene editing, and stem cell and autologous stem cell and allogenic stem cell transplantation therapies. The utility of iMyoblasts in gene editing has been demonstrated. Iyer et al., "Precise therapeutic gene correction by a simple nuclease-induced double-stranded break" Nature 568:561-565 (2019). This report shows that iMyoblast can be edited to correct a muscle disease gene, LGMD R7, caused by mutations in the TCAP gene encoding telethonin.

In one embodiment, the present invention contemplates a method comprising a cell culture protocol to efficiently create human muscle stem cells (referred to as iMyoblasts) by gene-free induction of human induced pluripotent stem cells (iPSCs). In one embodiment, the method further comprises "reserve cell" growth selection.

In one embodiment, the present invention contemplates a method for applying iMyoblasts technologies to a broad range of human muscular dystrophies regarding therapies including, but not limited to gene editing and epigenetics. In one embodiment, the iMyoblast technology comprises autologous muscle stem cell and allogenic muscle stem cell transplantation therapies for muscle disease and injury.

The present invention contemplates the development and application of a reliable and efficient protocol to produce expandable populations of human skeletal muscle stem cells from iPSC reprogrammed from adult cells of healthy control (Ctrl) and muscular dystrophy subjects. Previous studies have provided a foundation of reliable protocols to generate skeletal muscle from mouse and human Embryonic Stem cells (ESCs) and iPSCs, either by expression of muscle master regulatory transgenes including MYOD1 (Dekel et al., 1992; Maffioletti et al., 2015) or PAX7 (Darabi et al., 2012; Rao et al., 2018), or by transgene-free protocols that transition ESCs and iPSCs through a developmental progression using cocktails of growth factors and inhibitors, including Wnt, BMP, FGF and IGF, that regulate myogenesis in the vertebrate embryo (Borchin et al., 2013; Caron et al., 2016; Chal et al., 2015; Choi et al., 2016; Hosoyama et al., 2014; Shelton et al., 2014; Swartz et al., 2016; Xi et al., 2017; Xu et al., 2013). These protocols generate cultures of differentiated skeletal muscle that include minor subpopulations of muscle progenitors. However, these transgene-free skeletal myogenesis protocols do not efficiently generate human muscle stem cells that can be stably propagated and expanded while retaining their lineage commitment to muscle differentiation ex vivo and in vivo in muscle xenografts.

The data presented herein have focused on the molecular pathology of facioscapulohumeral muscular dystrophy (FSHD) using transgene-free iPSC myogenesis. For example, an efficient and reliable protocol has been discovered to isolate human skeletal muscle stem cells using a combination of transgene-free myogenic induction (Caron et al., 2016) and reserve cell selection. Muscle "reserve cells" previously were identified as a subpopulation of quiescent, undifferentiated cells resident in muscle cultures that can be reactivated to proliferate in response to growth factor rich media (Baroffio et al., 1996; Flamini et al., 2018; Laumonier et al., 2017; Yoshida et al., 1998). Reserve cell selection efficiently isolates human muscle stem cells from differentiated muscle cultures produced by transgene-free myogenic induction of FSHD and Ctrl iPSC. These myogenic stem cells, iMyoblasts, can be propagated and expanded for more than 30 population doublings while retaining their myogenic identity and self-renewal, as evidenced by their cell autonomous expression of PAX3 and MYOD1 muscle master regulatory genes and by their commitment to myotube differentiation, establishing their utility for molecular and gene editing myogenesis studies (Iyer et al., 2019).

Furthermore, iMyoblast efficiently xenoengraft into tibialis anterior (TA) muscles of adult NSG mice where they differentiate as muscle fibers and undergo embryonic to adult myosin isoform switching, demonstrating their regulatory plasticity for adult myogenesis and muscle maturation and utility for stem cell transplantation. Xenograft muscle generated by engraftment of iMyoblasts are composed of human muscle fibers as well as PAX3+ cells, showing that PAX3+ stem cells are resident in primary iMyoblast muscle xenografts and in xenograft muscle following secondary injury, providing evidence that iMyoblast xenografts have a stem cell population that can regenerate human muscle in response to injury. iMyoblast myogenesis technology has been applied to investigate epigenetic mechanisms regulating the FSHD disease gene, DUX4. DUX4 is a primate-specific member of the double homeobox (DUX) family of transcription factor genes of eutherian mammals located at the terminal repeat of the D4Z4 retrotransposon repeat array near the telomere of chromosome 4 (Gabriels et al., 1999). Healthy individuals have D4Z4 repeat arrays on chromosome 4 as well as chromosome 10, and these D4Z4 arrays are maintained in a highly condensed chromatin state, with hypermethylation of the DUX4 gene at its CpG sites and transcriptional repression in muscle. DUX4 normally functions during early development to coordinate zygotic genome activation and its expression is maintained in the male germline (De Iaco et al., 2017; Hendrickson et al., 2017; Snider et al., 2010). FSHD disease is associated with germline deletions and rearrangements that contract the D4Z4 locus on chromosome 4 to 10 or fewer repeats (FSHD1) or with mutations in chromatin-modifying genes such as SMCHD1 and DNMT3B (FSHD2). These 4 genetic disruptions lead to decondensation and hypomethylation of the D4Z4 repeat locus, low frequency transcription of DUX4 in skeletal muscle and activation of a battery of DUX4-regulated germline target genes (Geng et al., 2012; Lemmers et al., 2012; Lemmers et al., 2010; Snider et al., 2010; van den Boogaard et al., 2016; Yao et al., 2014). DUX4 misexpression leads to muscle toxicity, initially in the face, upper back and shoulder girdle, the clinical signature of FSHD, and often progresses, leading to severe disabilities (Bosnakovski et al., 2008; Rickard et al., 2015; Tawil and Van Der Maarel, 2006). DUX4 transcripts misexpressed in FSHD muscle are stabilized by RNA polyadenylation using a poly(A) signal present only in certain "disease permissive" 4qA haplotypes that are required for FSHD muscle disease (Lemmers et al., 2010). By contrast, germline cells utilize a DUX4 polyadenylation site located 3' to the 4qA poly(A) site, enabling its germline expression (Geng et al., 2012). DUX4 misexpression is muscle cell autonomous and upregulated during differentiation of primary myoblasts (P.Myo) isolated from biopsies of FSHD1 subjects (Geng et al., 2012; Yao et al., 2014).

In one embodiment, the present invention contemplates reprogrammed adult FSHD and Ctrl myoblasts and fibroblasts to iPSC, to generate iMyoblast for ex vivo and in vivo studies that establish their utility for developmental and epigenetic studies of the FSHD disease gene, DUX4, and the molecular pathology of FSHD and other human muscular dystrophies.

I. Conventional Muscle Stem Cell Culture Induction Methods

A three stage gene-free, growth factor protocol for inducing human embryonic stem cells (ESCs) into skeletal muscle has been reported by Caron et al., 2016 and commercially available from Myocea. The presently disclosed method improves this conventional ESC protocol to induce iPSCs reprogrammed from adult muscle progenitors and fibroblasts from normal individuals and patients with multiple muscular dystrophies into expandable human myoblast cell lines. Although it is not necessary to understand the mechanism of an invention, it is believed that the presently disclosed muscle iPSC induction method produces highly differentiated muscle and an expandable population of undifferentiated muscle stem cells.

In one embodiment, the present invention contemplates a method, comprising generating myogenic cells from iPSC reprogrammed from healthy, FSHD1, FKRP dystroglycanopathy and LGMD R7 patient cells. The data presented herein shows that the growth and differentiation phenotypes of control and disease iMyoblasts have been characterized and compared to primary adult myogenic cell lines. These data were based upon analysis of muscle biopsies using flow cytometry, immunohistology, single cell RNAseq and transcriptome analyses to define their lineage relationships and their differentiation gene expression programs. Both cell cultures and NSG immune deficient mouse muscle xenografts in were used in the analysis. iMyoblasts are also shown to predict the molecular pathology of FSHD1, FKRP dystroglycanopathies and LGMD R7 in cell culture and in muscle xenografts. Such data enables methods of gene correction and/or editing therapeutics to treat these diseases as well as to establish the utility of iMyoblasts for autologous and allogenic transplantation and muscle stem cell therapeutics.

In some embodiments, the present invention comprises an improved method to generate skeletal muscle from mouse and human ESCs and iPSCs, either by expression of muscle master regulatory transgenes including MYOD1 or PAX7 based upon previously reported strategies. Dekel et al., (1992); Maffioletti et al., (2015); Maffioletti et al., (2018);

(Darabi et al., 2012). In some embodiments, the present invention comprises an improved method that utilize transgene-free technology that transition ESCs and iPSCs through a developmental progression of skeletal myogenesis. For example, this developmental transition can be accomplished by using cocktails of growth factors and inhibitors known to regulate myogenesis in the vertebrate embryo, including, but not limited to, Wnt, BMPs, FGF and IGFs, Borchin et al., (2013); Caron et al., (2016); Chal et al., (2015); Choi et al., (2016); Hosoyama et al., (2014); Shelton et al., (2014); Swartz et al., (2016); Xi et al., (2017); and Xu et al., (2013). Previous protocols were reported to generate cultures of differentiated skeletal muscle that include minor subpopulations of muscle progenitor cells. Magli et al., (2017; and Pakula et al., (2019). Transgene-free skeletal myogenesis protocols, however, have not been reported to generate stably committed human muscle stem cell populations without sorting that can be propagated while retaining their lineage commitment to muscle differentiation that can be used for both ex vivo and in vivo muscle xenografts.

The presently disclosed improved methods have shown proof of principle using transgene-free iPSC myogenesis to investigate the molecular pathology of facioscapulohumeral muscular dystrophy (FSHD). A modification of an established transgene-free protocol resulted in an efficient and reliable protocol for isolation and propagation of skeletal muscle stem cells using a combination of transgene-free myogenic induction using the three stage protocols of Caron et al., (2016), commercially available from Myocea, followed by "reserve cell" selection from S3 stage iMyocytes differentiated in Myocea SKM03 medium. Muscle "reserve cells" are defined herein as a subpopulation of quiescent, undifferentiated cells resident in S3 stage cultures of differentiated muscle that can be reactivated to proliferate in response to growth factor rich media. Baroffio et al., (1996); Flamini et al., (2018); Laumonier et al., (2017); Scaramozza et al., (2019); and Yoshida et al., (1998). Although it is not necessary to understand the mechanism of an invention, it is believed that this presently disclosed "reserve cell" growth selection protocol can be used to isolate human muscle stem cells from differentiated muscle cultures produced by transgene-free myogenic induction of control and FSHD iPSC. The data presented wherein show that, once isolated, these iPSC myogenic cells (also referred to as iMyoblasts), can be propagated and expanded for greater than thirty (30) population doubles while retaining their myogenic identity. For example, these cells retain an autonomous expression of PAX3 and MYOD1 muscle master regulatory genes, commitment to myotube differentiation and upregulation of muscle genes. Furthermore, the present data show that iMyoblasts efficiently xenoengraft into tibialis anterior (TA) muscles of adult NSG mice where they differentiate as muscle fibers and undergo embryonic to adult myosin isoform switching, demonstrating their regulatory plasticity to obtain adult myogenesis and muscle maturation.

In some embodiments, the present invention comprises an improved method comprising iMyoblasts myogenesis in cells having an FSHD disease gene (e.g., DUX4). Although it is not necessary to understand the mechanism and its role in disease pathology. The DUX4 gene is believed to be a primate-specific member of the double homeobox (DUX) family of transcription factors of eutherian mammals and localizes to the terminal repeat of the D4Z4 retrotransposon repeat array near the telomere of chromosome 4. Gabriels et al., (1999). DUX4 activity has been reported to confound investigations of FSHD pathology and therapeutic development using traditional animal models. Dandapat et al., (2014); Mitsuhashi et al., (2013); and Wallace et al., (2011).

For example, somatic cells of healthy individuals have D4Z4 repeat arrays on chromosome 4 as well as chromosome 10. These D4Z4 arrays are normally maintained in a highly condensed chromatin state, with hypermethylation of the DUX4 gene at its CpG sites and transcriptionally repressed in muscle. DUX4 is expressed and functions briefly during very early development to coordinate zygotic genome activation and is maintained in the male germline. De Iaco et al., (2017; Hendrickson et al., (2017); and Snider et al., (2010). However, germline deletions and rearrangements that contract the locus to ten (10) or fewer D4Z4 repeats (FSHD1) or mutations in chromatin modifying genes such as SMCHD1 and DNMT3B (FSHD2) lead to decondensation and hypomethylation. It has been reported that this is necessary, but not sufficient, for low frequency transcriptional activation of DUX4 and activation and mis-expression in skeletal muscle of a large battery of germ line transcriptional target genes. de Greef et al., (2009); Geng et al., (2012); Lemmers et al., (2012); Lemmers et al., (2010); Snider et al., (2010); van den Boogaard et al., (2016); van Overveld et al., (2003); and Yao et al., (2014).

Mis-expression of DUX4 and its transcriptional targets has been reported to lead to muscle toxicity and degeneration, initially of the muscles in the face, upper back and shoulder girdle, which are symptoms of FSHD, but often progress to other muscle groups, leading to clinically severe disabilities. Bosnakovski et al., (2008); Rickard et al., (2015); and Tawil and Van Der Maarel, (2006). Notably, DUX4 transcripts mis-expressed in FSHD muscle can be stabilized by RNA polyadenylation at a disease-permissive polyadenylation site, identified genetically as the 4qA haplotype. Lemmers et al., (2010). This haplotype is prevalent in the genomes of the human population, and may occur in combination with the epigenetic derepression of the DUX4 locus in FSHD muscle disease. By contrast, germ line transcripts can utilize a polyadenylation site 3' to the 4qA poly A site, thus permitting germline specific functions. Geng et al., (2012). Further, DUX4 mis-expression is cell autonomous such that myoblasts cultured from biopsies of FSHD1 subjects with D4Z4 contractions mis-express DUX4 and DUX4 target genes during myotube differentiation. Geng et al., (2012; and Yao et al., (2014).

II. Improved Undifferentiated Muscle Stem Cell Production

In one embodiment, the present invention contemplates a method for reprogramming adult FSHD and healthy control myoblasts and fibroblasts into iPSCs. In one embodiment, the method comprises inducing the adult FSHD and healthy control myoblasts and fibroblasts along a myogenic trajectory to generate iMyoblasts as a myogenic stem cell population. Although it is not necessary to understand the mechanism of an invention, it is believed that these generated iMyoblasts are used for ex vivo and in vivo investigations of the developmental and epigenetic regulation of an FSHD disease gene (e.g., DUX4). It is further believed that iMyoblasts have a general utility for studies of the molecular pathology of muscle diseases and clinical therapeutics including, but not limited to, autologous stem cell and allogenic stem cell transplantation and/or gene editing.

It is believed that this expandable population of undifferentiated muscle stem cells can be efficiently and reproducibly recovered. In one embodiment, the undifferentiated muscle stem cells (iMyoblasts) are recovered by a growth factor stimulation. The data presented herein demonstrate that such recovered iMyoblast cells: i) express muscle stem cell markers and genes associated with embryonic and adult human muscle stem cells: ii) maintained as stable cell lines for greater than thirty (30) population doublings: iii) differentiate into muscle tissue; iv) activate a large set of muscle protein genes similar to those expressed during the differentiation of adult muscle stem cells; and v) regenerate reserve cells recovered from iMyotube cultures as tertiary Myoblasts (iTM).

Additionally, iMyoblast cells are capable of forming a xenoengraft in muscles of immune deficient mice and to differentiate to form human muscle fibers that are responsive to in vivo niche to undergo adult muscle maturation, as accessed by myosin isoform switching. iMyoblast xenografts include differentiated human muscle fibers and a population of PAX3+ iMyoblasts and can regenerate muscle in response to secondary injury. Furthermore, iMyoblasts produced from iPSC of patients with facioscapulohumeral muscular dystrophy (FSHD) and Limb-Girdle Muscular Dystrophies (LGMD) express the molecular pathologies associated with these diseases both in vitro in culture and in muscle xenografts in vivo.

iMyoblast human muscle stem cells can be successfully applied to model multiple human muscular dystrophies in addition to FSHD, including Duchenne Muscular Dystrophy, LGMD and Laminopathies. See, Table 1.

TABLE 1

Representative Muscular Dystrophies
Treatable With iMyoblast Cells

| Cell status | Genotype | iSM ID |
|---|---|---|
| Healthy control | >10 D4Z4 repeats | 15VM |
| | | 15VF |
| | | 17UM |
| | | 30WM |
| | | 30WF |
| Adult FSHD1 | 5-8 D4Z4 repeats | 15AM |
| | | 15AF |
| | | 17AM |
| | | 17AF |
| | | 30AM |
| | | 30AF |
| Non-manifesting FSHD | 5-8 D4Z4 repeats | 15BM |
| | | 30BM |
| | | 30BF |
| | | 47BM |

TABLE 1-continued

Representative Muscular Dystrophies
Treatable With iMyoblast Cells

| Cell status | Genotype | iSM ID |
|---|---|---|
| Infantile FSHD1 | 2-4 D4Z4 repeats | 54574/5F |
| | | 54578F |
| | | 54585F |
| | | 17FB019F |
| LGMD R7 | T-CAP mutation | RB25199 |
| FKRP | FKRP mutation | FP (R9) |
| Dystroglycanopathy | FKRP mutation | 8801 (R9) |
| | FKRP mutation | WWS4 |
| DMD | DMD mutation | TH001F |
| LAMA2-related CMD | LAMA2 Heterozygous mutation, clinically normal | GM23309 |
| | LAMA2 compound heterozygous mutation, clinically affected | GM23311 |

Such iMyoblasts are suitable for the development of gene editing therapeutics for muscle diseases, as evidenced by LGMD R7. Iyler et al., Nature 568:561-565 (2019). Genes which are differentially expressed in iMyoblasts were identified. These data are based on single cell (sc) RNA Seq analysis of adult muscle cell using transcriptomes of healthy control as compared to FSHD primary cells derived from muscle biopsies and myogenic cells at S1 and S2 stages of iPSC induction. These genes provide additional documentation that iMyoblast cells have a distinct myogenic stem cell transcriptome signature (FIG. 1, FIG. 10 and FIG. 19).

A. Transgene-Free Induction of Human iPSCs

Transgene-free iPSC myogenesis technology was used to compare skeletal myogenesis and expression of DUX4 in patient-derived FSHD iPSCs and healthy control iPSCs. iPSC lines were generated by reprogramming $CD56^+$ myoblasts and $CD56^-$ fibroblasts isolated from patient muscle or skin biopsies from: i) subjects with adult onset FSHD1 disease; ii) unaffected first-degree relatives who serve as healthy controls; iii) subjects with infantile FSHD1 onset disease; and subjects with Walker Warburg Syndrome (WWS) disease as controls. See Table II; Homma et al., (2012); and Jones et al., (2012).

TABLE II

Representative Cell Lines Used In The Present Studies

| ES/iPS | Status | ES/iPS ID | Sex | Age | Genotype | ISM ID | iPSC source |
|---|---|---|---|---|---|---|---|
| ESC[a] | Ctrl | Genea002 | M | | D4Z4 > | | |
| | | Genea015 | M | | 10U | | |
| | | Genes019 | F | | | | |
| | FSHD1 | Genes049 | F | | D4Z4 6U | | |
| | | Genea050 | M | | D4Z4 6U | | |
| | | Genea096 | F | | D4Z4: 7U | | |
| iPSC | Ctrl | 15Vbic (9) | F | 60 | D4Z4 > | 15VM9 | CD56 + Myoblast |
| | | 15Vbic (20) | | | 10U | 15VF20 | CD56 − Fibroblast |
| | | 17Ubic (10) | M | 21 | | 17UM10 | CD56 + Myoblast |
| | | 30Wbic (32) | M | 85 | | 30WM32 | CD56 + Myoblast |
| | Adult FSHD1 | 15Abic (8) | M | 66 | D4Z4 8U | 15AM8 | CD56 + Myoblast |
| | | 15Abic (8) | | | | 15AF8 | CD56 − Fibroblast |
| | | 17Abic (7) | M | 23 | D4Z4 5U | 17AM7 | CD56 + Myoblast |
| | | 17 Abic (15) | | | | 17AF15 | CD56 − Fibroblast |
| | | 30Abic (7) | M | 57 | D4Z4 9U | 30AM7 | CD56 + Myoblast |
| | Infantile FSHD1[b] | 54574/75* (15,27) | F | | D4Z4 2U | 54574F15 54575F27 | Skin Fibroblast |

TABLE II-continued

| | | | | | | | |
|---|---|---|---|---|---|---|---|
| | | Representative Cell Lines Used In The Present Studies | | | | | |
| ES/iPS | Status | ES/iPS ID | Sex | Age | Genotype | ISM ID | iPSC source |
| | | 54585 (42) | F | | D4Z4 4U | 54585F42 | Skin Fibroblast |
| | FKRP | WWS | M | | FKRP | WWS4 | |
| | Dystroglycanopathy[c] | | | | mutation | | Skin Fibroblast |

[1]ESC from Genea Biocells (Caron et al., 2016);
[2]Fibroblasts from Dr. Steven Moore at University of Iowa;
[3]iPSC from Dr. Anne Bang at Sanford Burnham Medical Research Institute Initial studies focused on transgene-free myogenic induction of SFSkD and control iPSCs using a previously reported protocol (e.g., Genea protocol). See, FIG. 2A; Caron et al., (2016). To validate this ESC myogenesis protocol for iPSC, cultures of FSHD and healthy control iPSCs and ESCs were assayed for the expression of muscle master regulatory genes, muscle protein genes, DUX4 and DUX4 transcriptional targets during S1, S2 and S3 stages of myogenesis using qPCR and immunohistology assays. See, FIG. 2B, FIG. 3; and FIG. 4.

The expression of a MYOD1 muscle master regulator gene and the MYH8 gene (an embryonic myosin differentiation marker) show that iPSCs and ESCs respond similarly to the transgene free myogenic induction protocol. See, FIG. 2B. S2 stage iPSC cultures were highly enriched for MYOD1[+]"induced Primary Myoblasts" (iPM), and S3 stage iPSC cultures were highly enriched for MF20[+] differentiated mononucleated myocytes, referred to as "induced primary myocytes (iPMCs)" which are typically found in embryonic muscles. See, FIG. 3A.

These findings established that the transgene-free induction protocol efficiently transitions iPSCs through myogenic development to differentiated myocytes. FSHD iPSCs and FSHD ESCs expressed low levels of the surrogate DUX4 biomarkers MBD3L2, TRIM43 and ZSCAN4 RNAs encoded by DUX4 transcriptional target genes as compared to healthy control ESCs and iPSCs. See, FIG. 4B and FIG. 11A. Unexpectedly, expression of DUX4 and DUX4 biomarkers increased only transiently during iPM induction and remained at very low levels following iMyocytes differentiation. See, FIG. 11A and FIG. 4C. Expression of DUX4 RNA is similarly maintained at low levels throughout iPSC-induced iPMC myogenesis. See, FIG. 4. iPMCs express DUX4 and DUX4 biomarkers at >1000 fold lower levels than differentiating cultures of FSHD primary myoblasts, even though iPMC and primary myotubes upregulate similar high levels of the MYH8 muscle differentiation marker. See, FIG. 5 and FIG. 6.

Notably, FSHD ESC lines do not upregulate expression of the DUX4 or DUX4 biomarker, MBD3L2, during S1, S2 and S3 stages of differentiation, validating that the low level, differentiation-independent regulation of DUX4 during induction and differentiation is not an artifact of iPSC reprogramming. iPSC and ESC cell lines from different FSHD subjects express different levels of DUX4 biomarkers. FIG. 4, FIG. 11A. These data may reflect the differences in DUX4 expression reported for differentiating cultures of FSHD primary myoblasts. Jones et al., (2012).

Together, these findings establish the utility of a transgene-free myogenesis protocol for FSHD and healthy control iPSCs, but unexpectedly show that DUX4 expression is repressed and differentiation independent in FSHD iPSC and ESC during myogenic induction.

B. "Reserve Cell" Selection of iPSC-Induced Muscle Stem Cells (iMyoblasts)

In one embodiment, the present invention contemplates a method comprising isolating iPSC-induced iMyoblasts using transgene-free skeletal muscle differentiation to produce stably propagated myogenic "reserve cells". For example, iMyoblasts may be maintained in growth factor rich medium as PAX3+ and MYOD1+ myogenic cells that can be propagated and expanded for more than twelve (12) passages that is equivalent to thirty (30) population doublings. In one embodiment, the iMyoblasts retain their commitment to differentiate including iMyoblast fusion to form differentiated myotubes, and upregulate expression of muscle protein RNAs in response to growth factor-deficient media (FIG. 2C), similar to primary myoblasts from adult muscle biopsies.

The iPSC "reserve cell" selection protocol has been successfully applied to the isolation of iMyoblasts from healthy control subjects as well as from subjects with FSHD and other muscular dystrophies including FKRP dystroglycanopathies, limb girdle muscular dystrophy type R7 and Duchenne muscular dystrophy (DMD). Furthermore, it was demonstrated that the iMyoblasts retain their capacity for differentiation ex vivo, xenoengraftment and differentiation in vivo. These findings establish that iMyoblast technology is useful for investigations of molecular, genetic and epigenetic mechanisms regulating human muscle differentiation and muscle pathology. Additionally, the iMyoblast technology supports gene editing therapeutics using patient cells, and provide an abundant source of muscle stem cells for autologous transplantation therapies. Iyer et al., (2019)

The finding that DUX4 expression is repressed to low levels in FSHD iPSCs and ESCs during S1, S2 and S3 primary myogenic induction See, FIG. 4, FIG. 11A and is upregulated during iMyoblast differentiation, as assayed by qPCR and NanoString RNA expression assays See, FIG. 5, FIG. 6 and FIG. 7; and Chen et al. (2016) and using a GFP DUX4 reporter See, FIG. 6C, suggested that FSHD iMyoblasts behave similarly to FSHD biopsy myoblasts (bMB).

To this end, a "reserve cell" growth factor selection protocol was used that was reported to isolate quiescent, undifferentiated myogenic stem cells from differentiated cultures of the mouse C2C12 cells. Yoshida et al., (1998). Cultures of differentiated FSHD and control iPMCs were dissociated, replated and passaged in a growth factor-rich medium also used to maintain primary myoblasts with the objective of stimulating the proliferation of quiescent undifferentiated stem cells populating differentiated S3 stage cultures. Remarkably, it was found that this "reserve cell" selection protocol efficiently and reliably recovers a highly enriched proliferative population of FSHD and control myogenic cells, referred to as iMyoblasts. Immunohistological assays shown herein demonstrate that such proliferating cultures of iMyoblasts, like iPSC induced S2 stage cells, are MYOD1[+] and can be induced to undergo myotube differentiation in response to growth factor-free differentiation medium and generate myotubes that express myosin heavy chain, as well as a subpopulation of DAPI[+]/MF20[−] cells that includes "reserve cells". See, FIG. 3A.

These iMyoblast "reserve cells" can be re-isolated by simulation with growth medium to regenerate cultures of S3 stage cultures differentiated in SKM03 medium available from Myocea. iMyoblasts behave as stem cells based on their capacity to regenerate reserve cells for recovery as tertiary Myoblasts (iTM). See, FIG. 8. These data validate the bipotentiality of iMyoblasts as "reserve cells" for growth and differentiation. Differentiated iMyotube cultures were enriched for multinucleated myotubes in contrast to S3 stage cultures, which differentiated as predominantly mononucleated iMyocytes. See, FIG. 3A. Flow cytometry assays revealed that FSHD and control iMyoblasts include cell markers such as CD82[+] (an established marker of fetal and adult human myoblasts), CD56[+], as well as other myogenic cell markers including, for example, CD318, ERBB3 and NGFR. Alexander et al., (2016); Pakula et al., (2019); Uezumi et al., (2016); and Hicks et al., (2018). See, FIG. 3E. Cultures of primary FSHD biopsy cells included a subpopulation of CD82[−]/CD56[−] non-myogenic cells that are likely mesenchymal cells (bMes) including fibroadipogenic precursors (FAP) based on their expression of PDGFRα. See, FIG. 3E and FIG. 9C. The CD82[+]/CD56[+] and CD82[+]/CD56[−] cells from FSHD and control iMyoblasts cultures both undergo myotube differentiation. See, FIG. 3D. These data affirm the commitment of iMyoblast cells to myogenic differentiation.

The data presented herein shows that iMyoblasts express PAX3 and MYOD1 myogenic master regulatory RNAs. In contrast, primary myoblasts express PAX7, MYF5 or MYF6 in addition to PAX3 and MYOD1. See, FIG. 3B, FIG. 9. Differentiating iMyotubes and S3 stage iMyocytes express embryonic/fetal MYH8 RNA, but not adult fast twitch muscle MYH1 RNA expressed by differentiating primary myoblasts. See, FIG. 5. These data further support the beliefs that iMyoblasts are lineage-related to PAX3[+] myogenic cells prevalent in embryonic and fetal muscles and/or to PAX3[+] muscle satellite cells. Buckingham and Relaix, (2007); Buckingham and Relaix, (2007; Scaramozza et al., (2019); and Yang et al., (2016). Although it is not necessary to understand the mechanism of an invention, it is believed that the presently disclosed iMyoblasts: i) proliferate in growth factor rich medium; ii) have a 12 hr cell doubling time; iii) maintained at low passage as frozen stocks that can be expanded for more than 12 passages (>30 population doublings); iv) maintain expression of PAX3 and MYOD1 muscle master regulatory genes; and v) maintain a commitment to differentiate and upregulate expression of MYH8 and CKM muscle protein RNAs in response to serum free differentiation medium; and retain their potential to replenish themselves as reserve cells and iTM. See, FIG. 3 and FIG. 8. The data establish the utility of the presently disclosed iMyoblasts as an accurate and reliable cell model based upon molecular and cellular parameters.

C. Single Cell RNASeq Analysis Of Myoblasts

The data presented herein demonstrate that qPCR and single cell RNA sequencing (scRNASeq) gene expression analyses establish that iMyoblasts derived from FSHD and healthy control subjects are myogenic progenitor lineages sharing gene expression signatures similar to embryonic myogenic cells. This gene expression signature includes, but is not limited to, expression of PAX3 and MYOD1, but not PAX7, MYF5, or MYF6, which, in addition to PAX3 and MYOD1, are co-expressed by adult primary myoblasts. See, FIG. 1, FIG. 3, FIG. 9, FIG. 10 and FIG. 19. iMyoblasts are shown to express CD82 and CD318 cell surface proteins associated with fetal myogenic lineages including cells that express CD56 and CD82, which also are co-expressed by adult myoblasts. See, FIG. 3E. Notably, CD56[−]/CD82[+] and CD56[+]/CD82[+] iMyoblasts are myogenic and undergo myotube differentiation ex vivo See, FIG. 3D. Healthy control iMyoblasts, FSHD iMyoblasts and WWS iMyoblasts were shown to efficiently xenograft and differentiate in the TA muscles of NSG mice. See, FIG. 12, FIG. 13, FIG. 14, and FIG. 17.

In one embodiment, the present invention contemplates that iMyoblasts muscle xenografts produce PAX3[+] satellite cells capable of regeneration of human muscle in response to injury or disease, as suggested by the capacity of iMyoblasts to generate "reserve cells" in response to differentiation See, FIG. 8 and for iMyoblast xenografts to regenerate in response to secondary injury See, FIG. 18. Ex vivo, newly iMyoblast-differentiated myotubes express: i) embryonic/fetal MYH3 RNA; ii) intermediate levels of embryonic/adult slow twitch MYH7; iii) intermediate levels of embryonic fetal/adult type 2A slow twitch skeletal muscle MYH8 RNAs; iv) low levels of late fetal/adult fast twitch 2x skeletal muscle MYH1; and v) low levels of fetal/adult fast twitch 2x skeletal muscle MYH2 RNAs. These data are consistent with an embryonic-like lineage phenotype. In contrast, at 2 and 4 weeks following xenoengraftment, iMyoblasts-differentiated myotube expression of embryonic and neonatal MYH3, MYH7 and MYH8 isoform RNAs is down regulated and the expression of adult MYH1 and MYH2 adult fast isoform RNAs is upregulated. See, FIG. 15. These data demonstrate that iMyoblasts retain the regulatory plasticity of their embryonic myogenic lineage and respond as a fast muscle like the host TA muscle adult fast muscle fiber type. Schiaffino and Reggiani, (2011). Although it is not necessary to understand the mechanism of an invention, it is believed that that healthy control myosin isoform switching in iMyoblast xenografts is likely a response to motor neurons that reinnervate injured and regenerating muscles and regulate myosin isoform expression.

These data suggest that an in vivo model has been found implicating DUX4 function in FSHD muscle pathology because FSHD iMyoblast xenograft muscle expressed DUX4 biomarkers similar to patient FSHD primary myoblasts.

Single-cell next generation RNA sequencing (scRNASeq) was used to compare the myogenic lineage phenotypes of proliferating cultures of FSHD and healthy control iMyoblast with S1 and S2 stage iPM and with biopsy muscle. iMyoblast cultures for scRNASeq assays were generated by "reserve cell" selection of iPSC lines reprogrammed from parental CD56+ primary myoblasts of six (6) subjects, including three (3) adult-onset FSHD subjects (cohorts 15A, 17A and 30A) and their unaffected control family members (cohorts 15V, 17U and 30W). Assays were also performed on proliferating cultures of unsorted muscle biopsy-derived primary cells, iPSC-derived S1 and S2 stage iPM from the same subjects.

For each cell type (e.g., S1, S2, iMyoblast, and primary cells), individual cultures from each of the six donors were dissociated, and equal cell numbers were pooled in a suspension immediately before loading on a 10x Genomics Chromium platform for scRNASeq. Pooling of the donor cells of each cell type served two purposes: i) to minimize possible batch effects during downstream processing steps, including mRNA capture, library generation, and sequencing; and ii) to more readily detect and eliminate barcodes linked to the capture of cell doublets or multiple cells.

For each cell suspension, two replicates were loaded in adjacent chambers on the 10× platform and processed simultaneously for mRNA capture, library preparation and sequencing. Natural polymorphisms in the transcripts from each donor were identified by limited bulk RNASeq of the individual cell pellets from unpooled S1 stage induced cells and iMyoblasts, and variants detected in 3' RNA of expressed genes were used to de-multiplex each cell barcode to the individual of origin and to eliminate barcodes linked to more than a single donor. Kang et al., (2018).

Raw scRNASeq reads were mapped to the reference genome GRCh38 and collapsed to obtain Unique Molecular Identifiers (UMI) using Cell Ranger 3.0.0. Further quality control filtering to remove cells with >5,500 detected genes or >12% mitochondrial reads were performed using tools in Seurat v3.1.4 to obtain 5,635 S1 cells, 5,802 S2 cells, 6,943 iMyoblast cells and 6,611 biopsy-derived primary cells for downstream analyses. Among these 24,991 cells, a median of 2,678 genes per cell and 7,909 UMI per cell was detected. See, FIG. 9A.

UMI counts were normalized, and principal component reduction was used to construct a shared nearest neighbor graph that was visualized using the Uniform Manifold Approximation and Projection (UMAP) method as implemented in Seurat v3.1.4. See, FIG. 9. The UMAP plot showed distinct clusters for S1, S2, iMyoblasts and primary cells cultured from muscle biopsies, indicating global differences in gene expression across these cell types that may reflect lineage-specific transcriptomes. See, FIG. 9A. Each of these main clusters included cells contributed by each subject in a heterogeneous distribution that could not be accounted for by cell cycle state as estimated by cell cycle gene expression signatures. See, FIG. 9B. This heterogeneity could reflect either batch effects related to independent cultures, the dissociation step or biological differences between the samples.

Primary cells cultured from muscle biopsies segregated into two distinct clusters, consistent with flow cytometry. A first cluster of bMyoblasts expressed muscle master regulatory RNAs, including PAX3, PAX7, MYOD1, MYF6 and MYF5 (about 80% of total cells) as well as myogenic regulators such as WNT7B and SIX1. See, FIG. 9C, FIG. 10 and FIG. 19; Lu et al., (2013); von Maltzahn et al., (2012); and Ridgeway and Skerjanc, (2001). A second cluster of bMes expressed PDGFRa mRNA that is a marker of FAP. See, FIG. 9C; Contreras et al., (2016; Joe et al., (2010); and Olson and Soriano, (2009).

iMyoblasts, and S1 stage and S2 stage primary induced myogenic cells segregated into three distinct myogenic clusters based on expression of PAX3 and MYOD1 RNAs, consistent with qPCR analyses. See, FIG. 2 and FIG. 3., These data affirm that the iPSC myogenic induction and iMyoblast "reserve cell" selection protocols generate populations of myogenic cells distinct from their parental bMyoblasts. Consistent with this, iMyoblasts, S1, S2 stage and bMyoblasts myoblasts differentially express RNAs that, in some cases, reflect their myogenic identity such as iMyoblasts expression of CDH2, an embryonic myogenic cell marker. See, FIG. 19; Charlton et al., (1997). The myogenic functions of iMyoblast cluster-enriched RNAs such as RGS4, SNGN, GOS2, and SLC2A1 remain unknown. See FIG. 1, FIG. 10 and FIG. 19.

Primary myoblasts expressed DES, an established myogenic marker. Li et al., (1994). In contrast, iMyoblasts did not express DES but did express VIM. Further, S1-stage iPSCs differentially expressed early developmental markers including, but not limited to, MEOX1, BMP4, and FOXC1 RNAs as previously reported for iPSCs. Chal et al., (2018). S2 iPM clusters were observed to be heterogeneous and include a subset of cells that express high levels of MYOD1 RNA more closely related to S1 cells and a subset of cells in G1 that express muscle differentiation regulators, including myogenin and MEF2C, and muscle protein RNAs, including muscle CKM and MYH8. These data indicate that S2 cells captured at a single time point may comprise cells in various states of transition from proliferation to differentiation and is consistent with a change in S2 cells toward an elongated cell morphology coincident with induction of high MYOD1 expression. See, FIG. 9 and FIG. 10. Overall, these scRNASeq results provide strong evidence that iMyoblast cells isolated by "reserve cell" selection are a distinct myogenic cell lineage.

D. Upregulated DUX4 in FSHD iMyoblast and FSHD Primary Myoblasts

The present data shows a comparison of the expression of muscle protein RNAs and DUX4 biomarker RNAs between FSHD and healthy control iMyoblast and parental primary myoblasts of cohorts 17 and 15 undergoing myotube differentiation. See, FIG. 5 and FIG. 6. FSHD iMyoblasts and their parental primary myoblasts comparably upregulated the expression of DUX4 biomarkers during differentiation induction in serum-free media, including Opti-MEM medium and N2 medium. See FIG. 7. Furthermore, FSHD iMyoblast and primary myoblasts engineered with a DUX4-GFP reporter express DUX4 at similar low frequencies in FSHD myotubes leading to death within 36 hr, establishing that iPSC reprogramming does not disrupt DUX4's characteristic low frequency activation and cell toxicity. See, FIG. 6C; and Rickard et al., (2015). FSHD iMyoblasts and primary myoblasts upregulate similar high-level expression of muscle RNAs during myotube differentiation, although differentiating iMyoblasts and primary myoblasts differentially express embryonic MYH8 and adult MYH1, respectively. The kinetics of upregulation of the muscle RNAs are similar in FSHD and control iMyoblasts and primary myoblasts. In contrast, upregulation of DUX4 biomarkers during myotube differentiation is delayed in cultures of parental bMyoblasts compared to iMyoblasts. See, FIGS. 6A, and 7A. These data suggest that healthy control iMyoblasts and parental bMyoblasts do not upregulate DUX4 biomarker RNAs during differentiation, although unlike iMyoblasts, bMyoblasts moderately upregulated DUX4 biomarkers at later differentiation (e.g., Day 6).

To investigate whether parental cell type of origin impacts iMyoblast muscle differentiation, the expression of muscle and DUX4 biomarker RNAs was compared in iMyoblasts isolated from FSHD and healthy control iPSCs derived by reprogramming of: i) parental primary myoblasts from FSHD and healthy control subjects (e.g., 17AM and 17UM); ii) iPSCs from biopsy fibroblasts of an FSHD subject (17AF); and iii) skin fibroblasts of FSHD patients (54574/5F C27, 54574/5F C15 and 54585F). See, FIG. 7. qPCR assays showed that after 7 days of differentiation, FSHD iMyoblast reprogrammed from myoblasts or fibroblasts express similar levels of muscle master regulators (Pax3 and MYOD1) muscle protein RNAs (CKM, MYOG and MYH8) and DUX4 biomarker RNAs (MBD3L2, TRIM43, LEUTX and ZSCAN4). These findings establish that iMyoblasts do not retain an epigenetic memory of their cell specific regulatory programs during reprogramming that impacts reserve cell selection, iMyoblast myogenic differentiation and DUX4 regulation.

E. DUX4 4qA CpG Hypomethylation and Epigenetic Repression

The role of DNA methylation in DUX4 repression was determined during iPSC reprogramming. Bisulfite DNA sequencing was utilized to quantitate the CpG methylation status of the DUX4 4qA locus in FSHD and healthy control bMyoblasts prior to and following their iPSC reprogramming and during iPSC induction and iMyotube differentiation.

As previously reported, the 4qA DUX4 loci of FSHD bMyoblasts from family cohorts 15 and 17 have approximately 20% methylated CpGs compared to 60% in healthy control bMyoblasts. See, FIG. 11B; and Jones et al., (2015). The data herein shows that DUX4 4qA remains hypomethylated in parental FSHD primary myoblasts whereas DUX4 4qA in healthy control primary myoblasts remained hypermethylated. These low and high levels of 4qA methylation of DUX4 4qA in FSHD and healthy control iPSC, respectively, were maintained throughout S1, S2 and S3 induction and iMyoblast growth and differentiation. See, FIG. 11C. Similar CpG DNA methylation results were obtained for human control and FSHD ESCs. See FIG. 16.

The low level DUX4 RNA expression in iPMs and iPMCs, therefore, is not mediated by 4qA DUX4 hypermethylation during iPSC reprogramming. iPSCs are believed to have functional DNA methylation/demethylation machinery. iPSC reprogramming led to hypermethylation of the MYOD1 core enhancer of FSHD and healthy control primary myoblasts, but this core enhancer becomes demethylated during myogenic induction and S3 differentiation. See, FIG. 11D. These data correlated with the upregulation of MYOD1. See, FIG. 2A. Furthermore, the data is consistent with previous observations made during somite myogenesis in the developing mouse embryo. (Brunk et al., (1996). These findings indicate that the 4qA DUX4 locus may be associated with a contracted D4Z4 repeat that is refractory to hypermethylation and demethylation machinery active in iPSCs.

F. 5-AzaC Derepression of DUX4 Expression

To investigate epigenetic mechanisms responsible for DUX4 repression during reprogramming and iPM induction, a blinded screen was conducted to identify epigenetic drugs that activate DUX4 in FSHD iPM undergoing myogenesis.

iPMs were treated for 24 hr with a pulse of epigenetic drugs, followed by culturing for 7 days in iPM growth medium and 7 days of iPMC differentiation medium. The cultured iPMs were then subjected to qPCR analysis to determine the expression of MBD3L2 RNA (a DUX4 biomarker) and MYH8 RNA (a muscle differentiation marker data now shown). Of the thirty-four (34) epigenetic drugs tested, a DNA demethylating drug (e.g., 5-azacytidine (5-AzaC)) effectively increased DUX4 expression in a concentration dependent manner to levels comparable to iMyoblasts and primary myoblasts, as assayed by MBD3L2 RNA biomarker expression. See, FIG. 11D. At high 5-AzaC concentrations, MYH8 RNA expression decreased. It is believed that this result reflects previously reported DUX4 toxicity due to increased levels of DUX4 expression. Rickard et al., (2015). Treatment of FSHD ESC iPMs with 5-AzaC similarly resulted in high levels of DUX4 expression (data not shown). The present data shows that 5-AzaC treatment of proliferating iMyoblasts induces only a small increase in DUX4 biomarker expression in myotubes at lower concentrations, indicating that the 5-AzaC sensitive repression in iPM is not operative in iMyoblasts. See, FIG. 11D. A genome-wide methylome analysis using Illumina chip assays revealed that 5-AzaC treatment causes selective demethylation of many sequences throughout the genome, consistent with a demethlyation mechanism of action, but candidate loci for DUX4 repression could not be identified (data not shown).

G. Differentiation of FSHD and Healthy Control iMyoblast Xenoengrafts

Xenografts of FSHD iMyoblasts, healthy control iMyoblasts, primary myoblasts and Walker Warburg Syndrome (WWS) iMyoblasts were grown on NSG immune-deficient mice. See, FIG. 12; and FIG. 13A. The xenoengraftment protocol produced highly humanized domains of human muscle in the tibialis anterior (TA) muscle that had been subjected to hindlimb irradiation to block mouse satellite cell regeneration and $BaCl_2$ injury to destroy mouse muscle fibers to establish a niche for engraftment of human cells. See, FIG. 12A. Xenoengraftment was assayed by immunohistology and qPCR using human-specific antibodies and qPCR primers. The data show that FSHD iMyoblast and control primary myoblast and control iMyoblast xenografts differentiated to form human fibers within 2 weeks following engraftment. See, FIG. 12, FIG. 13, FIG. 14 and FIG. 17.

Xenograft muscle was clustered in highly humanized domains of $BaCl_2$ injury that are largely devoid of mouse muscle, as assayed by immunostaining of human nuclei using lamin A/C[+] antibody and human fibers with spectrin-β1 antibody. See, FIG. 12B. Humanized domains within xenografted TA muscles are delineated by immunostaining with extracellular matrix protein collagen VI, which is expressed by iMyoblast and bMyoblasts. See, FIG. 14 and FIG. 10, respectively. The human muscle fibers produced by iMyoblasts and primary myoblasts are oriented in parallel with residual peripheral mouse fibers along the sarcolemma matrix remaining after $BaCl_2$ destruction of mouse fibers.

Dystrophin[+] mouse muscle fibers persist within peripheral uninjured regions of TA muscle (data not shown), but were rare within the humanized domains, and human muscle fibers are largely associated with human nuclei, identified by lamin A/C+ immunostaining. Peripheral mouse fibers do not have centralized nuclei, validating the effectiveness of leg irradiation for blocking mouse satellite cell regeneration.

DAPI[+]/lamin A/C[−] mouse nuclei also are present within human muscle xenografts, but are not directly associated with the sarcolemma of human fibers and include CD31[+] mouse endothelial cells that rebuild the vascular system in xenograft muscle (data not shown). iMyoblast xenografts are more variable in size than xenografts of primary myoblasts, likely in part reflecting differences in their growth and differentiation ex vivo and xenoengraftment requirements, which were optimized for primary myoblasts.

Xenograft muscles of FSHD primary myoblasts and iMyoblast express high levels of DUX4 and MBD3L2 RNA disease genes compared to xenografts of control primary myoblasts and iMyoblast. See, FIG. 12C. FSHD and control xenografts also express muscle RNAs, MYH8 and CKM, at comparable levels at 2 and 4 weeks post engraftment, although expression is lower in FSHD muscles, likely reflecting DUX4 toxicity. See, FIG. 12C.

Xenografts of FSHD and control iMyoblast and primary myoblasts have spectrin-β1[+] fibers in 2 and 4 weeks, but FSHD xenografts generated using FSHD iMyoblast and primary myoblasts are smaller and more variable, as assayed by immunohistology and qPCR using human-specific markers, likley reflecting variability in DUX4 cell death. See, FIG. 12B and FIG. 14.

Disease LGMD R7 and WWS iMyoblasts can be xeno-engrafted into mouse TA muscles at high frequency, further demonstrating the efficiency of iMyoblast xenoengraftment and the utility of the xenoengraftment assay for multiple muscle disease cell lines. See, FIG. 13.

The maturation of muscle fibers generated by iMyoblasts and primary myoblasts following xenoengraftment into the TA host muscle was demonstrated using a previously reported myosin heavy chain (MYH) isoform expression assay. Schiaffino et al., (2015). Expression of MYH isoforms was assayed in FSHD and control iMyoblast cells and primary myoblasts at Day 6 of ex vivo differentiation in cell culture and in xenograft muscles at 2 and 4 weeks following xenoengraftment into the mouse TA muscle. MYH isoform expression was quantitated using a custom NanoString panel and digital assays with human-specific muscle probes. See, FIG. 15. In ex vivo iMyotubes and primary myotubes both FSHD and controls express highest levels of embryonic/fetal MYH3 and intermediate levels of embryonic/adult slow twitch MYH7 and embryonic fetal/adult type 2A slow twitch skeletal muscle MYH8. By contrast, iMyotubes express lower levels of late fetal/adult fast twitch 2x skeletal muscle MYH1 and fetal/adult fast twitch 2x skeletal muscle MYH2 compared to primary myotubes. In 2 and 4 week iMyotube xenograft muscles, the expression of embryonic and neona-tal MYH3, MYH7 and MYH8 isoforms becomes down regulated and the expression of adult MYH1 and MYH2 adult fast isoforms becomes upregulated, showing that iMyoblast muscle undergo MYH switching from embryonic to adult fast twitch muscle isoforms. See FIG. 15. Similarly, but to lesser extent, primary myoblast xenografts also upregulate expression of adult fast twitch isoforms, MYH1 and MYH2, and expression of embryonic, neonatal and slow twitch isoforms MYH3, MYH7 and MYH8 is down regu-lated. The expression levels of MYH4 isoform are low and remained unchanged following xenoengraftment.

These findings, therefore, provide evidence that FSHD and control iMyoblast and primary myoblast muscle xeno-grafts have regulatory plasticity to undergo MYH isoform switching from embryonic to adult fast twitch MYH iso-forms in response to the fast twitch environment of the mouse TA muscle.

H. Ex Vivo iMyoblast Differentiation Enhancement Media

Proliferating iMyoblasts from Ctrl and FSHD1 subjects efficiently fuse and differentiate as iMyotubes in response to growth factor-free differentiation N2 and Opti-MEM media and upregulate CKM and MYH8 muscle protein RNAs to levels comparable to bMyoblasts. By contrast to iMyotubes and iMyocytes did not express high levels of adult MYH1 RNA, further reflecting their embryonic lineage phenotypes. See, FIG. 5.

iMyoblast cultures differentiated in growth factor-free media also include a subpopulation undifferentiated cells that can be recovered as tertiary iMyoblast lines by reserve cell selection and growth medium stimulation of cultures maintained for 7 days in serum free medium Opti-MEM. See, FIG. 8. These data provide evidence for the sustained self-renewal potential of iMyoblasts. Ctrl and FSHD1 iMyo-tubes upregulated expression of muscle RNAs regardless of whether iMyoblasts were derived from reprogrammed parental fibroblasts or bMyoblasts, indicating that the epi-genetic regulatory landscapes of adult parental cell type did not impact iPSC reprogramming for reserve cell iMyoblast selection or their commitment to undergo myotube differ-entiation. See, FIG. 7B.

To evaluate the effects of media on iMyoblast differen-tiation, a custom NanoString panel of human-specific RNA probes was developed to enable digital quantification to assay muscle and DUX4 target gene RNA expression in iMyotubes and muscle xenografts. See, FIG. 5, FIG. 6 and FIG. 15.

iMyotube and bMyotube differentiation in N2 serum-free culture medium were compared to N2 medium supple-mented with different combinations of myogenic signaling regulators previously shown to enhance myotube differen-tiation. Hicks et al. (2018); Tanoury et al., "Prednisolone rescues Duchenne Muscular Dystrophy phenotypes in human pluripotent stem cells-derived skeletal muscle in vitro. bioRxiv, 860 2020.2010.2029.360826 (2020); and Selvaraj et al., "Screening identifies small molecules that enhance the maturation of 862 human pluripotent stem cell-derived myotubes" Elife 8, (2019). These media include: i) N2+SB medium supplemented with TGFβ inhibi-tor SB431542 (SB); ii) N2+SB+P+C medium supplemented with (SB), corticosteroid Prednisolone (P), and a GSK3 260 inhibitor/Wnt signaling activator, CHIR99021 (C); and iii) N2+SB+De+Da+F medium supplemented with (SB), the corticosteroid Dexamethasone (De), α gamma-Secretase/ Notch signaling inhibitor DAPT (Da), and an adenyl cyclase activator Forskolin (F). See, FIG. 5B and FIG. 6B. All three N2-supplemented media significantly increased expression of muscle RNAs MYH7, MYH8 and CKM in Ctrl and FSHD1 iMyotubes, but not adult MYH1 which is expressed at low levels in iMyotubes and S3 iMyocytes. See FIG. 5B.

Increases in muscle RNA expression were correlated with significantly increased iMyotube networks of multinucle-ated myotubes, most prevalent in N2+SB+P+C medium. See, FIG. 20. The expression of MYOD1 or PAX3 myogenic regulatory RNAs was variable in different myogenic cell populations but for iMyoblasts, changes in PAX3 and MYOD1 expression were not consistently modulated by the media that increased muscle RNA expression, showing that these media affect differentiation but not myogenic commit-ment. By contrast to iMyoblasts, bMyotube differentiation was responsive to N2+SB but not to N2+SB+P+C or N2+SB+De+Da+F media, and N2+SB+De+Da+F media completely inhibited bMyoblast differentiation and fusion without decreasing PAX3 or MYOD1 myogenic specifica-tion genes, indicating that these blocked, undifferentiated cells retain their myogenic identity. See, FIGS. 5B and 20B.

S2 cultures differentiated in S3 medium supplemented with SB+P+C and SB+De+Da+F significantly increased expression of muscle RNAs MYH7, MYH8 and CKM, but not MHY1, and promoted iMyocytes with a more robust bipolar morphology, but not myotube fusion. See, FIG. 5 and FIG. 20.

These findings, therefore, establish that FSHD and Ctrl S3 Myocytes, iMyoblasts and bMyoblasts respond differently to each of these specialized differentiation media, consistent with the scRNA-Seq transcriptome findings that each is a distinct myogenic lineage.

It should be noted that, DUX4 target gene expression was also assayed in FSHD1 iMyotube cultures in response to media that enhance myotube differentiation and compared to FSHD bMyotubes and S3 iMyocytes. See, FIG. 5. iMyotube cultures expressed highest levels of DUX4 target genes in N2 serum free medium, and complex media dramatically reduced expression of DUX4 target genes to very low levels, fully uncoupling differentiation and DUX4 expression. See FIG. 6B.

By contrast, bMyotubes optimally expressed DUX4 target gene and muscle RNAs in N2+SB medium. N2+SB+P+C medium had no effect, and N2+SB+De+Da+F media blocked both DUX4 target gene and muscle expression as well as blocked fusion. See, FIGS. 5B, FIG. 6B and FIG. 20. The repression of DUX4 target gene expression in FSHD1 iMyotubes and bMyotubes may be partially attributable to corticosteroids. Pandey et al., "Culture Conditions Affect Expression of DUX4 in 894 FSHD Myoblasts" Molecules 20:8304-8315 (2015). But corticosteroids alone, in N2 media, only partially repressed DUX4 target gene expression (data not shown). DUX4 target gene expression in FSHD1 iMyotubes also was inhibited by Losmapimod, a p38 inhibitor of DUX4 in bMyotubes. See, FIG. 21; and Rojas et al., "P38α Regulates Expression of DUX4 in Facioscapulohumeral Muscular Dystrophy" bioRxiv, 700195 (2019). These data show that FSHD1 iMyoblasts and bMyoblasts share signaling pathways for DUX4 regulation and are suitable models for FSHD drug studies targeted to inhibiting DUX4 expression.

III. Clinical Relevance of iPSC Reprogramming

In one embodiment, the present invention contemplates iMyoblasts generated from iPSCs that were reprogrammed from primary myoblasts and fibroblasts. In one embodiment, the iMyoblasts have identical myogenic growth and differentiation phenotypes as the primary myoblasts and fibroblasts. Although it is not necessary to understand the mechanism of an invention, it is believed that the present data show that iMyoblasts are generated in response to iPSC during myogenic induction, independent of an epigenetic myogenic program retained during iPSC reprogramming of parental primary myoblasts.

For example, during S2 stage induction, iPM cells express high levels of MYOD1 which likely activates MYOD1 autoregulation, as previously shown for somatic cells in response to high level MYOD1 transgene expression. Weintraub et al., (1989). MYOD1 is maintained by autoregulation in iMyoblasts, providing a mechanism to maintain its expression independent of inductive signaling and enable its muscle master regulatory function to stably commit iMyoblast to a myogenic regulatory program of muscle differentiation. The molecular basis for iMyoblast bipotentiality for growth and differentiation are less evident, although it is notable that iMyoblast differentially express the G0/G1 switch gene 2 (G0S2). See, FIG. 10 and FIG. 19; Heckmann et al., (2013). It is believed that the G0/G1 switch gene 2 regulates re-entry of quiescent "reserve cells" into the cell cycle in response to growth factor stimulation. iMyoblasts also differentially express regulatory proteins including RGS4 (G protein signaling), SRGN (intracellular proteoglycan mediator of granule mediated apoptosis), EDIL3 (EGF-repeats-integrin binding) and PTX3 (pentraxin family-pattern recognition molecules for innate immunity) as well as Wnt, BMP, TGFβ, Notch signaling pathway genes with known functions in embryonic myogenesis, adult satellite cell renewal and muscle regeneration. See, FIG. 10; Chang and Kioussi, (2018). These genes likely contribute to the unique growth and differentiation phenotypes of iMyoblasts, both ex vivo and in muscle xenografts.

In one embodiment, the present invention contemplates that iPSC reprogramming and iMyoblasts are useful to provide clinical therapeutics for FSHD by revealing the molecular and epigenetic regulation of the FSHD disease gene, DUX4. For example, scRNASeq analyses show that FSHD and healthy control iMyoblasts and primary myoblasts have distinct transcriptomes as embryonic and adult myogenic lineages. The presently disclosed scRNASeq and flow cytometry analyses identify populations of non-myogenic cells that are more abundant in FSHD muscle primary cultures which have a distinct transcriptome signature that includes a FAP biomarker (PDGFRα), as well as COL6A, TFP12 and PENK1 RNAs that may be useful molecular markers of FSHD muscle pathology. See, FIG. 10 and FIG. 19.

The data presented herein demonstrate that FSHD iMyoblasts isolated from iPSCs that were reprogrammed from fibroblasts and myoblasts of FSHD subjects similarly upregulate DUX4 as well as muscle protein genes during differentiation. These data suggest that DUX4 is not controlled by epigenetic mechanisms inherited from parental primary myoblasts during reprogramming. See, FIG. 7. Further, iMyoblasts upregulate DUX4 in iMyotubes nuclei at similar low frequencies to primary myoblasts, suggesting that DUX4 expression is controlled by cell autonomous modifiers. Such modifiers might include, but are not limited to, D4Z4 contraction size and DNA methylation that determine the frequency and levels DUX4 expression.

The data presented herein also provides evidence that DUX4 may be developmentally regulated by epigenetic mechanisms. Additionally, DUX4 4qA alleles associated with D4Z4 contracted chromosomes remain hypomethylated in FSHD iPSC and FSHD ESC. See, FIG. 11 and FIG. 16. These findings contradict a previous report that DUX4 is hypermethylated in FSHD iPSC and these same FSHD ESC lines, using bisulfite sequencing primers that were not 4qA allele-specific to enable detection of DUX4 4qA hypomethylation over the predominance of methylation from D4Z4 repeat sequences. Dion et al., (2019). Although DUX4 4qA remains hypomethylated during iPMC differentiation, its expression is highly repressed during iPSC myogenesis by DNA methylation mechanism that can be reversed by brief pre-treatment of iPM cells with the DNA methylation inhibitor 5-AzaC. See, FIG. 11D.

IV. Muscle Disease and Injury

Xenograft muscles were produced by engraftment of healthy control cells and FSHD iMyoblasts that persist for at least forty (40 weeks). See, FIG. 17. These data suggest that iMyoblast cells are useful for long-term muscle repair.

Xenograft muscles were produced by engraftment of iMyoblast cell to generate both differentiated muscle fibers and PAX3+ cells that may function as regenerative muscle stem cells that regenerate xenograft muscle in response to secondary injury. See, FIG. 18. These data suggest that iMyoblast cells are useful for stem cell therapeutics as well as stem cell replacement therapies for treatment of genetic muscle diseases through autologous and heterologous transplantation.

V. Differential Gene Expression and Pathway Analyses

Differences in gene expression between the six cell classes, S1, S2A, S2B, iMyoblast, P. Myo and P. Mes, were quantitated using edgeR (Robinson et al., 2010), based on pseudo-bulk expression profiles (Tung et al., 2017) comprising summed counts of all cells from the same class and donor to avoid spurious pseudoreplication effects (Hurlbert, 1984). Cells in these clusters had highly distinct transcriptomes: the 15 pairwise comparisons had a minimum of 4600 differentially expressed coding and non-coding genes at false discovery rate (FDR)<0.05, and a median of 7656— over half of the 14103 genes tested after removing those with low expression. It is possible that some differences may be attributable to technical batch effects, as cells of the same type (i.e., S1, S2, iMyoblast, or primary) from all donors were multiplexed during the single-cell encapsulation and library construction. This does not apply to comparisons of S2A vs. S2B and P.Myo vs. P.Mes, although these may be biased toward small P-values since these clusters are defined based on the same transcriptomic data that is being compared between clusters (Zhang et al., 2019).

Tests of differential expression between FSHD and Ctrl samples from the same cell cluster are not subject to the biases above, but their power is limited by the small number of subjects and by low expression of DUX4 and its targets, as expected for proliferating FSHD cells. For this reason, the present data does not focus of these comparisons, though the single gene, AC004556.1, having an FDR<0.05 in these comparisons appears to be an artifact. A common variant in the gene MRPL23 happens to occur in these FSHD subjects but not the Ctrl subjects may cause reads from MRPL23 to be assigned to the gene AC004556.1 on an unlocalized scaffold instead.

To further characterize transcriptional differences between cell clusters, Gene Ontology (GO) and KEGG pathway enrichment analyses were performed using the edgeR functions goana and kegga (Young et al., 2010), applying more stringent cutoffs on differential expression, P-value <1E-06 and |log 2(FC)|>1, and with enrichment analyses performed separately for up- and down-regulated genes. The top ranked GO and KEGG categories for each of the 15 pairwise comparisons, sorted by p-value for enrichment (data not shown) are summarized below.

The top ranked categories for the iMyoblast vs. P.Myo comparison included categories with myogenic genes, including ECM, focal adhesion, and migration/chemotaxis genes (Csapo et al., 2020; Gillies and Lieber, 2011; Rayagiri et al., 2018; Thorsteinsdottir et al., 2011), signaling (Chal and Pourquie, 2017), and transcription (Berkes and Tapscott, 2005; Buckingham and Relaix, 2015). Both the up- and down-regulated genes were significantly enriched for ECM genes, including distinct collagen gene isoform usage, with COL4A1, COL4A2, COL4A5, COL4A6, COL8A1, COL11A1 and COL13A1 up in iMyoblast compared to P.Myo, and COL6A1, COL6A2, COL6A3, COL1A2, COL5A2, COL7A1, COL8A2 and COL22A1 up in P.Myo compared to iMyoblast. Other genes up in iMyoblast included AGRN, QSOX1, DSP, ECM1, SLIT2, EXT1, EXTL1 and EXTL3, and up in P.Myo included DRAXIN, NFASC, EVL and ELN. iMyoblast and P.Myo also differentially expressed matrix processing enzymes gene family members for MMP, ADAMTS, and ADAM, and matrix regulatory protein gene family members, ITG, KRT, CDH, SEMA and LAM, all of which have regulatory functions during embryonic and adult myogenesis.

Signaling was among the top ranked G0 and KEGG categories included receptor regulatory activity, receptor ligand activity, and signaling receptor activator activity (enriched among genes up in P.Myo compared to iMyoblast), and PI3K-Akt, MAPK, Rap1, and Ras pathways (enriched among genes up in iMyoblast vs P.Myo). These pathways include differentially expressed FGF, WNT, FZD gene family members. Additionally, TGFB, PDGFA, EPHA2 and EPHB2, NOG, IGF2BP1 and IGF2BP3 and HMGA2 were up in iMyoblast, while GDNF, VEGFA, BMP4, BMP7, WISP1, SULF1 and GREM2 were up in P.Myo.

Transcription categories included DNA-binding transcription activator activity, for which specific genes up in P. Myo included KLF4, SOX8, SIX2, PITX3, SCX, SNAI1, SNAI2 and SMAD1, and genes up in iMyoblast included GATA3, GATA6, HAND2, MEIS2, GLI2, NOTCH1, ETS1 and ETS2. The top ranked KEGG categories for genes up in P.Myo compared to iMyoblast included mineral absorption, complement and coagulation cascades, arachidonic acid metabolism, and retinoic acid metabolism, whose functions in adult myogenesis are currently unknown.

The results above focus on differences between the myogenic lineages iMyoblast and P.Myo, but similarities between them can be seen by contrasting each with clusters S1 and S2A, cells in earlier stages of myogenic induction. In all four pairwise comparisons between earlier (S1 or S2A) and committed (iMyoblast or P.Myo) cells, genes up in the myogenic lineages are enriched for positive regulation of cell migration and TGFβ signaling, while genes up in the earlier stage are enriched in steroid and cholesterol biosynthesis categories, likely to inhibit replicative stress and replication check point activation leading to cell cycle arrest (Replogle et al., 2020).

Seurat dot plots graphically illustrate the differences in gene expression and detection frequency across cell populations for a manually curated set of selected genes. See, FIG. 18. This dot plot data is based on edgeR and GO/KEGG analyses (data not shown). Some curated genes showed cell-cluster-specific expression but many were expressed by multiple cell clusters, likely reflecting their shared developmental histories and myogenic functions. These dot plots validate that each cell cluster population has a distinct gene expression profile shared by cells from all six donors, and together with edgeR and GO and KEGG analyses, validate the identity of iMyoblast as a myogenic cell lineage distinct from cells during early stage iPSC induction and from adult biopsy cells.

iMyoblasts generated by iPSC reprogrammed from P.Myo or fibroblasts from adult muscle biopsies have similar myogenic growth and differentiation phenotypes, indicating that iMyoblast are generated in response to iPSC myogenic induction, independent of epigenetic inheritance during iPSC reprogramming. In contrast to current transgene-free iPSC myogenic induction protocols (Chal et al., 2016; Xi et al., 2017; Xi et al., 2020), the presently disclosed iMyoblast protocol efficiently and reproducibly generates an expandable population of myogenic progenitors. The utility of the iMyoblast reserve cell protocol is based on two features. First, a gene free myogenic growth factor induction protocol (Caron et al., 2016) rapidly initiates high level PAX3 and MYOD1 expression to activate a positive autoregulatory loop (Weintraub et al., 1989) that autonomously maintains MYOD1 expression in proliferating iMyoblast, without first transitioning iPSC through earlier mesodermal and somite developmental stages. Second, MYOD1-expressing iMyoblast proliferate while retaining their bi-potentiality to both differentiate and regenerate self-renewing reserve cells. The mechanisms that regulate of iMyoblast growth, differentiation and self-renewal are not fully understood.

Myogenic reserve cells have been previously identified in mouse and human myogenic cell populations and may be a general property of cultured myogenic cells (Laumonier et al., 2017; Yoshida et al., 1998). However, iMyoblast differentially express genes that known to regulate MYOD1 function, myoblast differentiation and self-renewal that may contribute to iMyoblast self-renewal, including ID genes (Benezra et al., 1990), Wnt and BMP antagonists, DKK1 (Jones et al., 2015a) and GREM1 (Fabre, 2020), RGS4 (Yilmaz et al., 2016), TXNRD1 (Mercatelli et al., 2017), UCHL1 (Gao et al., 2017), NR2F2 (Lee et al., 2017), FOXC2 (Lagha et al., 2009), and HMGA2 and IGF2BPs (Li et al., 2012). See, FIG. 19. CRISPR gene editing approaches established for iMyoblast (Iyer et al., 2019) will enable investigations of the functions of coding and non-coding genes in iMyoblast reserve cell differentiation and renewal.

EXPERIMENTAL

Example I iPSC Reprogramming

Human induced pluripotent stem cells (iPSC) were generated from CD56$^+$ myoblasts enriched from bicep muscle biopsies, CD56$^-$ fibroblasts or skin fibroblasts at the UMASS Medical School Transgenic Animal Modeling Core using CytoTune-iPS Sendai Reprogramming Kit (ThermoFisher). Isolated iPSC clones were confirmed to be OCT4 positive and Sendai virus negative. iPSCs were routinely maintained on Matrigel® (Corning) with StemMACS iPS-Brew XF® (Miltenyi Biotec). The cells were passaged every 4 days using StemMACS Passaging Solution XF® (Miltenyi Biotec) and the Rock inhibitor Y27632 (10 μM, STEM-CELL Technologies) for 24 hr to improve the survival rates.

Example II iMyoblast Isolation And Differentiation iPSC typically plated on 6-well plates, were induced for myogenic differentiation using media prepared by Genea Biocells and now commercially available as a skeletal muscle differentiation kit with SKM03 S3 Stage differentiation medium (Myocea) following the manufacturer's specifications. Myocea; Caron et al., (2016). After 6-7 days in S3 differentiation medium, culture plates were rinsed with 2 ml 1× phosphate buffered saline (PBS) and cells were detached from plates in 0.5 ml TrypLE Express® at 37° C. and diluted with 4.5 ml HMP growth medium (Ham's F-10 supplemented with: 20% FBS, 1% chick embryo extract, 1.2 mM CaCl$_2$, 1% antibiotic/antimycotic (Gibco) (optional). The cell suspension was pipetted 5-10 times to disperse cells and clear plates of residual cells, and then 0.5-1 ml of this cell suspension was plated onto 10 cm gelatin-coated dishes in 10 ml HMP medium, cells were cultured at 5% CO2 at 37° C. and fed daily with fresh HMP medium to support the growth of iMyoblast. After 2-3 culture passages, iMyoblast cells were recovered and maintained as frozen stocks for investigations.

Example III

Cell Culture

Fluorescence-activated cell sorting (FACS) of CD56$^+$ primary myoblasts recovered from muscle biopsies and iMyoblasts isolated from iPSC muscle cultures were routinely maintained on gelatin-coated 10 or 15 cm dishes in HMP growth medium and passaged at 70-90% confluence. Homma et al., (2012); Jones et al., (2012). To induce differentiation, cultures were grown to 95% confluence, then washed with PBS and cultured in serum free Opti-MEM or N2 medium (DMEM/F12 supplemented with 1% N2 supplement, 1% ITS and 1% L-glutamine) for 2-7 days at 37° C. under 5% CO$_2$. Barberi et al., (2007); Chal et al., (2016).

Example IV

Immunofluorescence

Cells were fixed on plates with 2% paraformaldehyde for 20 min at 37° C. After rinsing the plates three (3) times with PBS, the fixed cells were treated with a blocking/permeabilizing solution (e.g., PBS containing 2% bovine albumin, 2% goat serum, 2% horse serum and 0.2% Triton X-100).

Following incubation for thirty (30) min at room temperature the cells were incubated with primary antibodies in PBS at 4° C. overnight. Subsequently, the cells were washed three (3) times in PBS, and incubated with the corresponding secondary antibodies for 1 h at room temperature. See, Table III.

TABLE III

| Antibodies for immunofluorescence (IF) and immunohistochemistry (IHC) | | |
| --- | --- | --- |
| Primary antibody | Vendor | Cat# |
| MyoD1(Clone: 5.8A) | Dako | M3512 |
| MF20 | DSHB | MF 20 |
| MEF2C | Sigma | HPA005533 |
| Collagen Type VI | Millipore Sigma | MAB1944 |
| Lamin A/C | ThermoFisher Scientific | MA3-1000 |

Plates were washed twice in PBS and cells stained for 5 min with DAPI (Sigma) and fluorescence images were taken using a Nikon Eclipse TS 100 inverted microscope.

Example V

Flow Cytometry

Single cell suspensions of iMyoblast and primary myoblast cultures dissociated with TrypLE Express Enzyme (ThermoFisher) were washed with PBS, filtered with a 40 μm strainer, and incubated with antibodies suspended in PBS for 30-60 min on ice in the dark. See, Table IV.

TABLE IV

| Flow Cytometry Antibodies | | |
| --- | --- | --- |
| Primary antibody | Vendor | Cat# |
| APC Mouse Anti-Human CD56 | BD | 555518 |
| PE anti-human CD82 Antibody | BioLegend | 342103 |
| FITC anti-human CD318 (CDCP1) Antibody | BioLegend | 324004 |
| APC anti-human erbB3/HER-3 Antibody | BioLegend | 324708 |
| FITC anti-human CD271 (NGFR) Antibody | BioLegend | 345104 |
| PE anti-human CD18 Antibody | BioLegend | 373407 |

Cells were then washed in PBS and resuspended in PBS and 0.2% fetal calf serum, and flow cytometry was performed at UMASS Medical School Flow Cytometry Core. A BD FACS Aria IIu was used for quantification and a BD FACS C-Aria II Cell Sorter was used for cell sorting. FlowJo software was used for data analysis.

Example VI

Generation of DUX4-GFP iMyoblasts

DUX4 expression was assayed in primary myoblasts and iMyoblast expressing DUX4-GFP reporter using lentiviral vector and G418 selection. Rickard et al., (2015). Cells were infected using a modified spin-down method. Springer and Blau, (1997). In brief, 10$^5$ cells per well were plated on gelatin coated 6-well plates in HMP medium. The next day, cells were incubated with DUX4-GFP lentivirus in HMP medium for 15 min and then centrifuged at 1100×g for 30 min at 32° C. Medium containing virus was replaced with fresh medium and cells were cultured for 48 hours, then treated with 300 μg/ml G418 for 7 days for selection, with daily feedings and passaging at 90% confluence.

Example VII

Bisulfite Methylation Sequencing

Genomic DNA was isolated from cell pellets of FSHD and control ESCs (Genea Biocells) and iPSCs, iPMs and iMyoblasts using QIAamp DNA Blood Mini Kit® (QIA-GEN) and bisulfite converted using the EpiTect Kit® (QIA-GEN) following the manufacturer's specifications. DUX4 4qA and 4qA-L were PCR amplified from bisulfite treated DNA using nested primers and the MYOD1 Core Enhancer with primers that include CpG sites 1, 2 and 3. Jones et al., (2014); (Brunk et al., 1996); as shown in Table V.

TABLE V

| Primer Sequences DUX4 4qA and MYOD1 (Jones et al., 2014) | |
| --- | --- |
| Gene | Sequence (5'-3') |
| MYOD1 | For: AGTTGGGGGTATTTATGGGTTTTTTTATAAATTTTTG |
| | Rev: CCCCAAACCTCAAAACTCAATTAAAAAAACC |
| 4qA | 1438F: GTTTTGTTGGAGGAGTTT TAGGA |
| | 3742R: AACATTCAACCAAAATTT CACRAAA |
| | 3656R: AACAAAAATATACTTTTAACCRCCAAAAA |

Amplified DNAs were cloned into the pCR2.1 TOPO vector, which was transformed into TOP10 Chemically Competent *E. coli* and selected for kanamycin resistance. Cloned DNA of plasmids from kanamycin resistant colonies were sequenced using Sanger sequencing (Sequegen), and CpG methylation analysis analyzed by Bisulfite Sequencing DNA Methylation Analysis (BISMA) online software. Rohde et al., (2008); Rohde et al., (2010); Rohde et al., (2009).

Example VIII

Single Cell RNASeq

For each of the four cell types—cultures at stages S1, S2, iMyoblast and unsorted primary biopsy cells—the cells from three FSHD and three control subjects were detached from plates, dissociated and pooled immediately before loading two parallel runs of 8,000 and 10,000 cells on a Chromium platform (10× Genomics) for scRNA-seq. 3' Gene Expression v2 libraries (10× Genomics) from four Chromium runs were sequenced on an HS4K instrument at the UMMS Deep Sequencing Core. Cell Ranger version 3.1.0 (10× Genomics) and STAR 2.5.1b were used to align reads from FASTQ files to the human reference genome.

Gene annotations from GRCh38.93 were prepared with cellranger mkgtf as in Cell Ranger Reference 3.0.0, but with filtering modified to also retain gene biotypes "processed_transcript" and "bidirectional_promoter_lncRNA". Initial filtering, barcode counting, and UMI counting yielded an estimate of 29,049 potential cell barcodes. 92.4% of the 562.5 million total reads were in cells. SNPs for each subject were genotyped from bulk RNA-seq, performed by Novogene, of S1 and iMyoblast cells for each subject in Python 2.7.9 using Opossum 0.2 (Oikkonen and Lise, 2017) and Platypus 0.8.1 (Rimmer et al., 2014). These genotypes were used to assign cells from pooled scRNA-seq runs to their subject of origin using Demuxlet (downloaded on Aug. 3, 2018) (Kang et al., 2018), and 5.7% of the cells were filtered out that did not unambiguously match a single genotype.

Further filtering using the Seurat 3.1.4 package (Butler et al., 2018; Stuart et al., 2019) in R 3.6.2 removed 7.0% of the remaining cells that contained >12% UMIs mapped to mitochondrial genes, <1,000 or >5,500 detected genes, or >40,000 detected UMIs. This resulted in 24,991 cells, with a median of 2,678 genes detected per cell and 7,909 UMI per cell (FIG. 3A).

Cell clustering, cell cycle state estimation, and downstream analyses were performed for these cells in Seurat. Normalization and scaling were performed using SCTransform (Hafemeister and Satija, 2019) with regression against the percentage of mitochondrial gene expression. The 3,000 genes with highest variability across cells were used for principal component reduction, and components 1-30 were used to construct a shared nearest neighbor graph for unsupervised cell clustering using the Louvain algorithm. This resulted in 16 cell clusters (3 for S1 cells, 4 for S2 cells, 5 for iMyoblast cells, and 4 for muscle biopsy primary cells), which were visualized using the Uniform Manifold Approximation and Projection (UMAP) method with resolution 0.7 (McInnes et al., 2018).

Most of the within-cell-type subclusters were merged to reduce to 6 clusters, keeping separate the P.Mes cluster that was clearly distinct from the other 3 primary cell subclusters comprising P.Myo (FIG. 8B), and the S2A cluster that expressed low MYOD1 and CDH15 and distinguished it from the other 3 S2 subclusters comprising more differentiated S2B cells, as described in the Results.

The top 200 differentially expressed genes from each pairwise cell-type comparison using edgeR (below) were reviewed to provide a curated set of genes relevant to myogenesis or cell type expression shown herein as Seurat dot plots. See, FIG. 1 and FIG. 19.

Example IX

Muscle Xenografts

Immune deficient NOD-PrkdcscidIL2rγtmiWj1 mice (NSG, Jackson Lab) which lack the ability to produce mature B cells, T cells and natural killer (NK) cells and are highly sensitive to irradiation were used in accordance with the Institutional Animal Care and Use Committee (IACUC) at the University of Massachusetts Medical School.

NSG mice were anesthetized with ketamine/xylazine and their hindlimbs were subjected to 18 Gy of irradiation using a Faxitron® RV-650 or Faxitron® CellRad X-ray cabinet to ablate the host mouse satellite cell population. One day after irradiation, mice were anesthetized with isoflurane and Tibialis Anterior (TA) muscles were injected with 50 μl of 1.2% Barium Chloride (Sigma) bilaterally to degenerate mouse muscle. Three days after muscle injury, $1\times10^6$ pmary adult biopsy myoblasts or iMyoblasts were resuspended in 50 μl 1 mg/ml laminin (Sigma, L2020) in PBS and injected bilaterally into the body of TA muscles.

Xenoengrafted mice were euthanized 2-4 weeks post engraftment by $CO_2$ asphyxiation followed by cervical dislocation. For immunohistology experiments, TA muscles were isolated and embedded in optimal cutting temperature compound (OCT, Tissue Tek), frozen in liquid nitrogen cooled isopentane and kept at −80° C. until cryosectioning. For RNA isolation, xenoengrafted TA muscles were snap frozen in liquid nitrogen and kept at −80° C. until RNA extraction.

Example X

TA Sectioning and Immunohistology

Frozen TA muscles embedded in OCT in accordance with Example IX were cryosectioned using a Leica® CM3050 S Cryostat. Tissue sections 10 μm thick were mounted onto Superfrost® Plus glass microscope slides (Fisher Scientific) and kept at −20° C. until immunostained.

When thawed, the sections were fixed with ice cold acetone for 10 minutes at −20° C. A "mouse-on-mouse" (MOM) kit (Vector Laboratories) was used to reduce non-specific antibody staining per the manufacturer's specifications. Antibodies were used sequentially then slides were incubated with Hoechst Block® for 10 minutes. Following 2×5 min PBS washes, the slides were dried and coverslips mounted with Fluorogel®. Fluorescent images were taken using a Leica® DMR fluorescence microscope.

Example XI

RNA Isolation, qPCR & NanoString

Ribonucleic acid (RNA) was isolated either from cells in culture or from xenoengrafted TA muscles using the RNeasy® Plus Mini Kit (Qiagen) or Aurum® Total RNA Fatty and Fibrous Tissue kit (Bio-Rad) respectively per the manufacturer's specifications. For qPCR analysis, 2-5 μg of total RNA was converted into cDNA using the SuperScript III® First-Strand Synthesis System (Invitrogen) using previously reported primers. See, Table VI.

TABLE VI

| Housekeeping Gene RT-qPCR Primer Sequences | | | |
|---|---|---|---|
| Gene | NCBI Gene ID | Sequence (5'-3') | Reference |
| RPL13A | 23521 | For: AACCTCCTCCTTTTCCAAGC<br>Rev: GCAGTACCTGTTTAGCCACGA | Geng et al.,<br>(2012) |
| CKM | 1158 | For: ATGCCATTCGGTAACACCCAC<br>Rev: GCTTCTTGTAGAGTTCAAGGGTC | |
| MYH8 | 4626 | For: AATGCAAGTGCTATTCCAGAGG<br>Rev: ACAGACAGCTTGTGTTCTTGTT | |
| MYOG | 4656 | For: GGGGAAAACTACCTGCCTGTC<br>Rev: AGGCGCTCGATGTACTGGAT | |
| MYOD1 | 4654 | For: GCGGAACTGCTACGAAGG<br>Rev: AGGGCTCTCGGTGGAGAT | Lapan et al.,<br>(2012) |
| PAX3 | 5077 | For: CACCTTCACAGCAGAACAGC<br>Rev: CAGCTTGCTTCCTCCATCTT | Lapan et al.,<br>(2012) |
| PAX7 | 5081 | For: GGGAAGAAAGAGGAGGAGGA<br>Rev: TTCAGTGGGAGGTCAGGTTC | Lapan et al.,<br>(2012) |
| MYF5 | 4617 | For: CCACCTCCAACTGCTCTGAT<br>Rev: TGATCCGGTCCACTATGTTG | Lapan et al.,<br>(2012) |
| MBD3L2 | 125997 | For: GCGTTCACCTCTTTTCCAAG<br>Rev: GCCATGTGGATTTCTCGTTT | Geng et al.,<br>(2012) |
| TRIM43 | 129868 | For: ACCCATCACTGGACTGGTGT<br>Rev: CACATCCTCAAAGAGCCTGA | Geng et al.,<br>(2012) |
| ZSCAN4 | 201516 | For: TGGAAATCAAGTGGCAAAAA<br>Rev: CTGCATGTGGACGTGGAC | Geng et al.,<br>(2012) |
| LEUTX | 342900 | For: 5'-TGGCTACAATGGGGAAACTG-3'<br>Rev: 5'-CTGCTGCCTCTTCCATTTG-3' | Lim et al.,<br>(2015) |
| DUX4 | 100288687 | For: GGCCCGGTGAGAGACTCCACA<br>Rev: CCAGGAGATGTAACTCTAATCCAGGTTTGC | Rickard et<br>al., (2015) |

For quantification of housekeeping genes, DUX4 bio-marker or muscle differentiation marker expression, 20 ng of cDNA was used for each reaction. For quantification of DUX4 expression, 90-150 ng of cDNA was used in each reaction.

For NanoString RNA quantification, 50 ng or 150 ng of total RNA was used for cell culture and xenografted TA muscle, respectively. A muscle NanoString panel was constructed with human specific probes for muscle protein genes, muscle master regulatory genes, developmental transcription factors, signaling genes and multiple housekeeping genes and used for all analysis on an nCounter SprintR profiler (NanoString Technologies, Seattle, WA). Raw mRNA counts were normalized to a series of housekeeping genes (e.g., RPL13A, GAPDH, GUUSB, and VCP) using nSolverR software (NanoString Technologies, Seattle, WA).

Example XII

Differential Gene Expression and G0/KEGG Analyses

Values from the single-cell raw count matrix (prior to normalization) were summed for each combination of the 6 cell types of interest (S1, S2A, S2B, iMyoblast, P.Myo, P.Mes) and the 6 donors (15A, 15V, 17A, 17U, 30A, 30W) to obtain a table of pseudobulk counts for these 36 samples (Tung et al., 2017) (data not shown).

Tests of differential expression were performed on these pseudobulk counts using the R 4.0.1 package edgeR 3.30.3 (Lun et al., 2016; Robinson et al., 2010). Lowly expressed genes were filtered out with the function filterByExpr, and counts were normalized using calcNormFactors to yield values for 14,103 filtered genes across the 36 samples.

A quasi-likelihood negative binomial generalized log-linear model was specified with cell-type and donor as additive factors in the model. estimateDisp was used to estimate the dispersion for all genes, glmQLFit (robust=T) to fit a joint model to the data from all cell-types, and glmQLFTest to perform statistical tests of differential expression for each of the 15 contrasts between pairs of cell-types.

The false discovery rate (FDR) was computed with the function topTags. Genes that satisfied (unadjusted) P value <1.0E-06 and |log 2(FC)|>1 were considered differentially expressed and ranked by P value for each comparison. Comparisons between the three FSHD and three control donors used the same edgeR procedure as above, but with models fit separately for each cell type, including the filterByExpr step.

For GO/KEGG analyses, the differentially expressed (DE) genes, separated into up and down sets based on the sign of log 2(FC), were used as DE input, and the full set of genes from the edgeR analysis after the filterByExpr step was used as the gene universe.

Overrepresentation of GO terms in BP, CC, and MF ontologies (annotations from org.Hs.eg.db 3.11.4) were computed using the goana function and in KEGG pathways using the kegga function in edgeR, in both cases using log 2(CPM) [CPM=counts per million] as a covariate to adjust for potential biases due to gene expression level (Young et al., 2010). The top GO and KEGG based on overrepresentation P Value, for each comparison between cell types were summarized (data not shwon).

It should be noted that the gene AC004556.1 (ENSG00000276345) is on the unlocalized chr11 scaffold KI270721.1 in GRCh38, and it differs from the chr11 gene MRPL23 at only a single position, a common G>A variant in MRPL23 (rs12812; allele frequency ~18%; ncbi.nlm.nih-.gov/snp/rs12812). Thus, whether a RNA-seq read maps to MRPL23 or to AC004556.1 depends on its base-call at this variant position, and it appears that none of the Ctrl subjects has the variant but all three FSHD subjects are heterozygous for it. See, FIG. 19—bottom two rows). In a larger collection of FSHD and Ctrl subjects this variant had allele frequency ~20% in both cases (not shown), so this is not likely to reflect an FSHD-associated genotype, but rather a chance occurrence, and one for which the reported P-value for differential expression is artificially small because the sample variance for the number of reads assigned to AC004556.1 has severely underestimated the population variance. Note that this G>A variant has allele frequency 17% in gnomAD 2.1.1 (gnomad.broadinstitute.org/variant/ 11-1977552-G-A?dataset=gnomad_r2_1), which uses the GRCh37 genome assembly, but is not reported at all in gnomAD 3 (gnomad. broadinstitute.org/variant/11-1956322-G-A?dataset=gnomad_r3), which uses the GRCh38 genome assembly. This could be due to the presence of KI270721.1 in GRCh38 but not GRCh37, and indeed the whole ~100 kb region of chr11 with high homology to KI270721.1 has low coverage in gnomAD 3 (gnomad.broadinstitute.org/region/11-1900000-2100000?dataset=gnomad_r3).

Example XIII

Statistical Analysis qPCR data were shown as the mean±SEM. Statistical differences were evaluated using student's t test. Differences were considered significant when the P value was less than 0.05, *=P<0.05, =P<0.01, **=P<0.0001.

REFERENCE CITATIONS

Alexander, M. S., Rozkalne, A., Colletta, A., Spinazzola, J. M., Johnson, S., Rahimov, F., Meng, H., Lawlor, M. W., Estrella, E., Kunkel, L. M., et al. (2016). CD82 Is a Marker for Prospective Isolation of Human Muscle Satellite Cells and Is Linked to Muscular Dystrophies. Cell Stem Cell 19, 800-807.

Ardhanareeswaran, K., Mariani, J., Coppola, G., Abyzov, A., and Vaccarino, F. M. (2017). Human induced pluripotent stem cells for modelling neurodevelopmental disorders. Nat Rev Neurol 13, 265-278.

Barberi, T., Bradbury, M., Dincer, Z., Panagiotakos, G., Socci, N. D., and Studer, L. (2007). Derivation of engraftable skeletal myoblasts from human embryonic stem cells. Nature medicine 13, 642-648.

Baroffio, A., Hamann, M., Bernheim, L., Bochaton-Piallat, M. L., Gabbiani, G., and Bader, C. R. (1996). Identification of self-renewing myoblasts in the progeny of single human muscle satellite cells. Differentiation 60, 47-57.

Benezra, R., Davis, R. L., Lockshon, D., Turner, D. L., and Weintraub, H. (1990). The protein Id: a negative regulator of helix-loop-helix DNA binding proteins. Cell 61, 49-59.

Berkes, C. A., and Tapscott, S. J. (2005). MyoD and the transcriptional control of myogenesis. Semin Cell Dev Biol 16, 585-595.

Borchin, B., Chen, J., and Barberi, T. (2013). Derivation and FACS-mediated purification of PAX3+/PAX7+ skeletal muscle precursors from human pluripotent stem cells. Stem Cell Reports 1, 620-631.

Bosnakovski, D., Xu, Z., Gang, E. J., Galindo, C. L., Liu, M., Simsek, T., Garner, H. R., Agha-Mohammadi, S., Tassin, A., Coppee, F., et al. (2008). An isogenetic myoblast expression screen identifies DUX4-mediated FSHD-associated molecular pathologies. EMBO J 27, 2766-2779.

Brunk, B. P., Goldhamer, D. J., and Emerson, C. P., Jr. (1996). Regulated demethylation of the myoD distal enhancer during skeletal myogenesis. Dev Biol 177, 490-503.

Buckingham, M., and Relaix, F. (2007). The role of Pax genes in the development of tissues and organs: Pax3 and Pax7 regulate muscle progenitor cell functions. Annu Rev Cell Dev Biol 23, 645-673.

Burridge, P. W., Matsa, E., Shukla, P., Lin, Z. C., Churko, J. M., Ebert, A. D., Lan, F., Diecke, S., Huber, B., Mordwinkin, N. M., et al. (2014). Chemically defined generation of human cardiomyocytes. Nat Methods 11, 855-860.

Butler, A., Hoffman, P., Smibert, P., Papalexi, E., and Satija, R. (2018). Integrating single-cell transcriptomic data across different conditions, technologies, and species. Nature biotechnology 36, 411-420.

Caron, L., Kher, D., Lee, K. L., McKernan, R., Dumevska, B., Hidalgo, A., Li, J., Yang, H., Main, H., Ferri, G., et al. (2016). A Human Pluripotent Stem Cell Model of Facioscapulohumeral Muscular Dystrophy-Affected Skeletal Muscles. Stem Cells Transl Med 5, 1145-1161.

Chal, J., Al Tanoury, Z., Hestin, M., Gobert, B., Aivio, S., Hick, A., Cherrier, T., Nesmith, A. P., Parker, K. K., and Pourquie, O. (2016). Generation of human muscle fibers and satellite-like cells from human pluripotent stem cells in vitro. Nat Protoc 11, 1833-1850.

Chal, J., Al Tanoury, Z., Oginuma, M., Moncuquet, P., Gobert, B., Miyanari, A., Tassy, O., Guevara, G., Hubaud, A., Bera, A., et al. (2018). Recapitulating early development of mouse musculoskeletal precursors of the paraxial mesoderm in vitro. Development 145.

Chal, J., Oginuma, M., Al Tanoury, Z., Gobert, B., Sumara, O., Hick, A., Bousson, F., Zidouni, Y., Mursch, C., Moncuquet, P., et al. (2015). Differentiation of pluripotent stem cells to muscle fiber to model Duchenne muscular dystrophy. Nat Biotechnol 33, 962-969.

Chang, C. N., and Kioussi, C. (2018). Location, Location, Location: Signals in Muscle Specification. J Dev Biol 6.

Charlton, C. A., Mohler, W. A., Radice, G. L., Hynes, R. O., and Blau, H. M. (1997). Fusion competence of myoblasts rendered genetically null for N-cadherin in culture. J Cell Biol 138, 331-336.

Chen, J. C., King, O. D., Zhang, Y., Clayton, N. P., Spencer, C., Wentworth, B. M., Emerson, C. P., Jr., and Wagner, K. R. (2016). Morpholino-mediated Knockdown of DUX4 Toward Facioscapulohumeral Muscular Dystrophy Therapeutics. Mol Ther 24, 1405-1411.

Choi, I. Y., Lim, H., Estrellas, K., Mula, J., Cohen, T. V., Zhang, Y., Donnelly, C. J., Richard, J. P., Kim, Y. J., Kim, H., et al. (2016). Concordant but Varied Phenotypes among Duchenne Muscular Dystrophy Patient-Specific Myoblasts Derived using a Human iPSC-Based Model. Cell Rep 15, 2301-2312.

Csapo, R., Gumpenberger, M., and Wessner, B. (2020). Skeletal Muscle Extracellular Matrix—What Do We Know About Its Composition, Regulation, and Physiological Roles? A Narrative Review. Front Physiol 11, 253.

Contreras, O., Rebolledo, D. L., Oyarzun, J. E., Olguin, H. C., and Brandan, E. (2016). Connective tissue cells expressing fibro/adipogenic progenitor markers increase under chronic damage: relevance in fibroblast-myofibroblast differentiation and skeletal muscle fibrosis. Cell Tissue Res 364, 647-660.

Dandapat, A., Bosnakovski, D., Hartweck, L. M., Arpke, R. W., Baltgalvis, K. A., Vang, D., Baik, J., Darabi, R., Perlingeiro, R. C., Hamra, F. K., et al. (2014). Dominant lethal pathologies in male mice engineered to contain an X-linked DUX4 transgene. Cell Rep 8, 1484-1496.

Darabi, R., Arpke, R. W., Irion, S., Dimos, J. T., Grskovic, M., Kyba, M., and Perlingeiro, R. C. (2012). Human ES- and iPS-derived myogenic progenitors restore DYSTROPHIN and improve contractility upon transplantation in dystrophic mice. Cell Stem Cell 10, 610-619.

de Greef, J. C., Lemmers, R. J., van Engelen, B. G., Sacconi, S., Venance, S. L., Frants, R. R., Tawil, R., and van der Maarel, S. M. (2009). Common epigenetic changes of D4Z4 in contraction-dependent and contraction-independent FSHD. Hum Mutat 30, 1449-1459.

De Iaco, A., Planet, E., Coluccio, A., Verp, S., Duc, J., and Trono, D. (2017). DUX-family transcription factors regulate zygotic genome activation in placental mammals. Nat Genet 49, 941-945.

Dekel, I., Magal, Y., Pearson-White, S., Emerson, C. P., and Shani, M. (1992). Conditional conversion of ES cells to skeletal muscle by an exogenous MyoD1 gene. New Biol 4, 217-224.

Dion, C., Roche, S., Laberthonniere, C., Broucqsault, N., Mariot, V., Xue, S., Gurzau, A. D., Nowak, A., Gordon, C. T., Gaillard, M. C., et al. (2019). SMCHD1 is involved in de novo methylation of the DUX4-encoding D4Z4 macrosatellite. Nucleic Acids Res 47, 2822-2839.

Fabre, O. G., L; Parisi, A; Pattamaprapanont, P; Ahwazi, D; Brun, C; Chakroun, I; Taleb, A; Blais, A; Andersen, E; Ingerslev, LR; Maire, P; Rudnicki, M; Laurens, C; Citirikkaya, K; Garde, C; Lundell, L; Deshmukh, AS; Moro, C; Bourlier, V; Mounier, R; Le Grand, F; Barres, R (2020). GREM1 is epigenetically reprogrammed in muscle cells after exercise training and controls myogenesis and metabolism. bioRxiv.

Flamini, V., Ghadiali, R. S., Antczak, P., Rothwell, A., Turnbull, J. E., and Pisconti, A. (2018). The Satellite Cell Niche Regulates the Balance between Myoblast Differentiation and Self-Renewal via p53. Stem Cell Reports 10, 970-983.

Gabriels, J., Beckers, M. C., Ding, H., De Vriese, A., Plaisance, S., van der Maarel, S. M., Padberg, G. W., Frants, R. R., Hewitt, J. E., Collen, D., et al. (1999). Nucleotide sequence of the partially deleted D4Z4 locus in a patient with FSHD identifies a putative gene within each 3.3 kb element. Gene 236, 25-32.

Gao, H., Hartnett, S., and Li, Y. (2017). Ubiquitin C-Terminal Hydrolase L1 regulates myoblast proliferation and differentiation. Biochem Biophys Res Commun 492, 96-102

Geng, L. N., Yao, Z., Snider, L., Fong, A. P., Cech, J. N., Young, J. M., van der Maarel, S. M., Ruzzo, W. L., Gentleman, R. C., Tawil, R., et al. (2012). DUX4 activates germline genes, retroelements, and immune mediators: implications for facioscapulohumeral dystrophy. Dev Cell 22, 38-51.

Georgomanoli, M., and Papapetrou, E. P. (2019). Modeling blood diseases with human induced pluripotent stem cells. Dis Model Mech 12.

Gillies, A. R., and Lieber, R. L. (2011). Structure and function of the skeletal muscle extracellular matrix. Muscle Nerve 44, 318-331.

Gunhanlar, N., Shpak, G., van der Kroeg, M., Gouty-Colomer, L. A., Munshi, S. T., Lendemeijer, B., Ghazvini, M., Dupont, C., Hoogendijk, W. J. G., Gribnau, J., et al. (2018). A simplified protocol for differentiation of electrophysiologically mature neuronal networks from human induced pluripotent stem cells. Mol Psychiatry 23, 1336-1344.

Hafemeister, C., and Satija, R. (2019). Normalization and variance stabilization of single-cell RNA-seq data using regularized negative binomial regression. bioRxiv, 576827.

Hashimoto, A., Naito, A. T., Lee, J. K., Kitazume-Taneike, R., Ito, M., Yamaguchi, T., Nakata, R., Sumida, T., Okada, K., Nakagawa, A., et al. (2016). Generation of Induced Pluripotent Stem Cells From Patients With Duchenne Muscular Dystrophy and Their Induction to Cardiomyocytes. Int Heart J 57, 112-117.

Heckmann, B. L., Zhang, X., Xie, X., and Liu, J. (2013). The G0/G1 switch gene 2 (GOS2): regulating metabolism and beyond. Biochim Biophys Acta 1831, 276-281.

Hendrickson, P. G., Dorais, J. A., Grow, E. J., Whiddon, J. L., Lim, J. W., Wike, C. L., Weaver, B. D., Pflueger, C., Emery, BR., Wilcox, A. L., et al. (2017). Conserved roles of mouse DUX and human DUX4 in activating cleavage-stage genes and MERVL/HERVL retrotransposons. Nat Genet 49, 925-934.

Heslop, J. A., and Duncan, S. A. (2019). The Use of Human Pluripotent Stem Cells for Modeling Liver Development and Disease. Hepatology 69, 1306-1316.

Hicks, M. R., Hiserodt, J., Paras, K., Fujiwara, W., Eskin, A., Jan, M., Xi, H., Young, C. S., Evseenko, D., Nelson, S. F., et al. (2018). ERBB3 and NGFR mark a distinct skeletal muscle progenitor cell in human development and hPSCs. Nat Cell Biol 20, 46-57.

Homma, S., Chen, J. C., Rahimov, F., Beermann, M. L., Hanger, K., Bibat, G. M., Wagner, K. R., Kunkel, L. M., Emerson, C. P., Jr., and Miller, J. B. (2012). A unique library of myogenic cells from facioscapulohumeral muscular dystrophy subjects and unaffected relatives: family, disease and cell function. Eur J Hum Genet 20, 404-410.

Hosoyama, T., McGivern, J. V., Van Dyke, J. M., Ebert, A. D., and Suzuki, M. (2014). Derivation of myogenic progenitors directly from human pluripotent stem cells using a sphere-based culture. Stem Cells Transl Med 3, 564-574.

Hurlbert, S. H. (1984). Pseudoreplication and the design of ecological field experiments. Ecological monographs 54, 187-211.

Iyer, S., Suresh, S., Guo, D., Daman, K., Chen, J. C. J., Liu, P., Zieger, M., Luk, K., Roscoe, B. P., Mueller, C., et al. (2019). Precise therapeutic gene correction by a simple nuclease-induced double-stranded break. Nature 568, 561-565.

Jiwlawat, N., Lynch, E., Jeffrey, J., Van Dyke, J. M., and Suzuki, M. (2018). Current Progress and Challenges for Skeletal Muscle Differentiation from Human Pluripotent Stem Cells Using Transgene-Free Approaches. Stem Cells Int 2018, 6241681.

Joe, A. W., Yi, L., Natarajan, A., Le Grand, F., So, L., Wang, J., Rudnicki, M. A., and Rossi, F. M. (2010). Muscle injury activates resident fibro/adipogenic progenitors that facilitate myogenesis. Nat Cell Biol 12, 153-163.

Jones, T. I., Chen, J. C., Rahimov, F., Homma, S., Arashiro, P., Beermann, M. L., King, O. D., Miller, J. B., Kunkel, L. M., Emerson, C. P., Jr., et al. (2012). Facioscapulohumeral muscular dystrophy family studies of DUX4 expression: evidence for disease modifiers and a quantitative model of pathogenesis. Hum Mol Genet 21, 4419-4430.

Jones, T. I., King, O. D., Himeda, C. L., Homma, S., Chen, J. C., Beermann, M. L., Yan, C., Emerson, C. P., Jr., Miller, J. B., Wagner, K. R., et al. (2015). Individual epigenetic status of the pathogenic D4Z4 macrosatellite correlates with disease in facioscapulohumeral muscular dystrophy. Clin Epigenetics 7, 37.

Jones, T. I., Yan, C., Sapp, P. C., McKenna-Yasek, D., Kang, P. B., Quinn, C., Salameh, J. S., King, O. D., and Jones, P. L. (2014). Identifying diagnostic DNA methylation profiles for facioscapulohumeral muscular dystrophy in blood and saliva using bisulfite sequencing. Clin Epigenetics 6, 23.

Kammoun, M., Cassar-Malek, I., Meunier, B., and Picard, B. (2014). A simplified immunohistochemical classification of skeletal muscle fibres in mouse. Eur J Histochem 58, 2254.

Kang, H. M., Subramaniam, M., Targ, S., Nguyen, M., Maliskova, L., McCarthy, E., Wan, E., Wong, S., Byrnes, L., Lanata, C. M., et al. (2018). Multiplexed droplet single-cell RNA-sequencing using natural genetic variation. Nat Biotechnol 36, 89-94.

Kava, M., Chitayat, D., Blaser, S., Ray, P. N., and Vajsar, J. (2013). Eye and brain abnormalities in congenital muscular dystrophies caused by fukutin-related protein gene (FKRP) mutations. Pediatr Neurol 49, 374-378.

Lagha, M., Brunelli, S., Messina, G., Cumano, A., Kume, T., Relaix, F., and Buckingham, M. E. (2009). Pax3:Foxc2 reciprocal repression in the somite modulates muscular versus vascular cell fate choice in multipotent progenitors. Dev Cell 17, 892-899.

Lapan, A. D., Rozkalne, A., and Gussoni, E. (2012). Human fetal skeletal muscle contains a myogenic side population that expresses the melanoma cell-adhesion molecule. Hum Mol Genet 21, 3668-3680.

Laumonier, T., Bermont, F., Hoffmeyer, P., Kindler, V., and Menetrey, J. (2017). Human myogenic reserve cells are quiescent stem cells that contribute to muscle regeneration after intramuscular transplantation in immunodeficient mice. Sci Rep 7, 3462.

Lee, A. S., Harris, J., Bate, M., Vijayraghavan, K., Fisher, L., Tajbakhsh, S., and Duxson, M. (2013). Initiation of primary myogenesis in amniote limb muscles. Dev Dyn 242, 1043-1055.

Lee, H. J., Kao, C. Y., Lin, S. C., Xu, M., Xie, X., Tsai, S. Y., and Tsai, M. J. (2017). Dysregulation of nuclear receptor COUP-TFII impairs skeletal muscle development. Sci Rep 7, 3136.

Lemmers, R. J., Tawil, R., Petek, L. M., Balog, J., Block, G. J., Santen, G. W., Amell, A. M., van der Vliet, P. J., Almomani, R., Straasheijm, K. R., et al. (2012). Digenic inheritance of an SMCHD1 mutation and an FSHD-permissive D4Z4 allele causes facioscapulohumeral muscular dystrophy type 2. Nat Genet 44, 1370-1374.

Lemmers, R. J., van der Vliet, P. J., Klooster, R., Sacconi, S., Camano, P., Dauwerse, J. G., Snider, L., Straasheijm, K. R., van Ommen, G. J., Padberg, G. W., et al. (2010). A unifying genetic model for facioscapulohumeral muscular dystrophy. Science 329, 1650-1653.

Li, H., Choudhary, S. K., Milner, D. J., Munir, M. I., Kuisk, I. R., and Capetanaki, Y. (1994). Inhibition of desmin expression blocks myoblast fusion and interferes with the myogenic regulators MyoD and myogenin. J Cell Biol 124, 827-841.

Lim, J. W., Snider, L., Yao, Z., Tawil, R., Van Der Maarel, S. M., Rigo, F., Bennett, C. F., Filippova, G. N., and Tapscott, S. J. (2015). DICER/AGO-dependent epigenetic silencing of D4Z4 repeats enhanced by exogenous siRNA suggests mechanisms and therapies for FSHD. Hum Mol Genet 24, 4817-4828.

Lu, L., Sun, K., Chen, X., Zhao, Y., Wang, L., Zhou, L., Sun, H., and Wang, H. (2013). Genome-wide survey by ChIP-seq reveals YY1 regulation of lincRNAs in skeletal myogenesis. EMBO J 32, 2575-2588.

Lun, A. T., Chen, Y., and Smyth, G. K. (2016). It's DE-licious: A Recipe for Differential Expression Analyses of RNA-seq Experiments Using Quasi-Likelihood Methods in edgeR. Methods Mol Biol 1418, 391-416.

Maffioletti, S. M., Gerli, M. F., Ragazzi, M., Dastidar, S., Benedetti, S., Loperfido, M., VandenDriessche, T., Chuah, M. K., and Tedesco, F. S. (2015). Efficient derivation and inducible differentiation of expandable skeletal myogenic cells from human ES and patient-specific iPS cells. Nat Protoc 10, 941-958.

Maffioletti, S. M., Sarcar, S., Henderson, A. B. H., Mannhardt, I., Pinton, L., Moyle, L. A., Steele-Stallard, H., Cappellari, O., Wells, K. E., Ferrari, G., et al. (2018). Three-Dimensional Human iPSC-Derived Artificial Skeletal Muscles Model Muscular Dystrophies and Enable Multilineage Tissue Engineering. Cell Rep 23, 899-908.

Magli, A., Incitti, T., Kiley, J., Swanson, S. A., Darabi, R., Rinaldi, F., Selvaraj, S., Yamamoto, A., Tolar, J., Yuan, C., et al. (2017). PAX7 Targets, CD54, Integrin alpha9beta1, and SDC2, Allow Isolation of Human ESC/iPSC-Derived Myogenic Progenitors. Cell Rep 19, 2867-2877.

McInnes, L., Healy, J., and Melville, J. (2018). Umap: Uniform manifold approximation and projection for dimension reduction. arXiv preprint arXiv:180203426.

Mercatelli, N., Fittipaldi, S., De Paola, E., Dimauro, I., Paronetto, M. P., Jackson, M. J., and Caporossi, D. (2017). MiR-23-TrxR1 as a novel molecular axis in skeletal muscle differentiation. Sci Rep 7, 7219.

Mitsuhashi, H., Mitsuhashi, S., Lynn-Jones, T., Kawahara, G., and Kunkel, L. M. (2013). Expression of DUX4 in zebrafish development recapitulates facioscapulohumeral muscular dystrophy. Hum Mol Genet 22, 568-577.

Oikkonen, L., and Lise, S. (2017). Making the most of RNA-seq: Pre-processing sequencing data with Opossum for reliable SNP variant detection. Wellcome Open Res 2, 6.

Olson, L. E., and Soriano, P. (2009). Increased PDGFRalpha activation disrupts connective tissue development and drives systemic fibrosis. Dev Cell 16, 303-313.

Pagliuca, F. W., Millman, J. R., Gurtler, M., Segel, M., Van Dervort, A., Ryu, J. H., Peterson, Q. P., Greiner, D., and Melton, D. A. (2014). Generation of functional human pancreatic beta cells in vitro. Cell 159, 428-439.

Pakula, A., Spinazzola, J. M., and Gussoni, E. (2019). Purification of Myogenic Progenitors from Human Muscle Using Fluorescence-Activated Cell Sorting (FACS). Methods Mol Biol 1889, 1-15.

Rao, L., Qian, Y., Khodabukus, A., Ribar, T., and Bursac, N. (2018). Engineering human pluripotent stem cells into a functional skeletal muscle tissue. Nat Commun 9, 126.

Rayagiri, S. S., Ranaldi, D., Raven, A., Mohamad Azhar, N. I. F., Lefebvre, O., Zammit, P. S., and Borycki, A. G. (2018). Basal lamina remodeling at the skeletal muscle stem cell niche mediates stem cell self-renewal. Nat Commun 9, 1075.

Replogle, J. M., Norman, T. M., Xu, A., Hussmann, J. A., Chen, J., Cogan, J. Z., Meer, E. J., Terry, J. M., Riordan,
D. P., Srinivas, N., et al. (2020). Combinatorial single-cell CRISPR screens by direct guide RNA capture and targeted sequencing. Nat Biotechnol 38, 954-961.

Rickard, A. M., Petek, L. M., and Miller, D. G. (2015). Endogenous DUX4 expression in FSHD myotubes is sufficient to cause cell death and disrupts RNA splicing and cell migration pathways. Hum Mol Genet 24, 5901-5914.

Ridgeway, A. G., and Skerjanc, I. S. (2001). Pax3 is essential for skeletal myogenesis and the expression of Six1 and Eya2. J Biol Chem 276, 19033-19039.

Rimmer, A., Phan, H., Mathieson, I., Iqbal, Z., Twigg, S. R. F., Wilkie, A. O. M., McVean, G., and Lunter, G. (2014). Integrating mapping-, assembly- and haplotype-based approaches for calling variants in clinical sequencing applications. Nature genetics 46, 912-918.

Robinson, M. D., McCarthy, D. J., and Smyth, G. K. (2010). edgeR: a Bioconductor package for differential expression analysis of digital gene expression data. Bioinformatics 26, 139-140.

Rohde, C., Zhang, Y., Reinhardt, R., and Jeltsch, A. (2010). BISMA—fast and accurate bisulfite sequencing data analysis of individual clones from unique and repetitive sequences. BMC Bioinformatics 11, 230.

Rohde, C., Zhang, Y., Jurkowski, T. P., Stamerjohanns, H., Reinhardt, R., and Jeltsch, A. (2008). Bisulfite sequencing Data Presentation and Compilation (BDPC) web server—a useful tool for DNA methylation analysis. Nucleic Acids Res 36, e34.

Rohde, C., Zhang, Y., Reinhardt, R., and Jeltsch, A. (2010). BISMA—fast and accurate bisulfite sequencing data analysis of individual clones from unique and repetitive sequences. BMC Bioinformatics 11, 230.

Rohde, C., Zhang, Y., Stamerjohanns, H., Hecher, K., Reinhardt, R., and Jeltsch, A. (2009). New clustering module in BDPC bisulfite sequencing data presentation and compilation web application for DNA methylation analyses. Biotechniques 47, 781-783.

Rouger et al., Musculoskeletal PathologySystemic Delivery of Allogenic Muscle Stem CellsInduces Long-Term Muscle Repair and ClinicalEfficacy in Duchenne Muscular Dystrophy Dogs. The American Journal of Pathology 179(5): 2501-2518 (2011)

Scaramozza, A., Park, D., Kollu, S., Beerman, I., Sun, X., Rossi, D. J., Lin, C. P., Scadden, D. T., Crist, C., and Brack, A. S. (2019). Lineage Tracing Reveals a Subset of Reserve Muscle Stem Cells Capable of Clonal Expansion under Stress. Cell Stem Cell 24, 944-957e945.

Schiaffino, S., and Reggiani, C. (2011). Fiber types in mammalian skeletal muscles. Physiol Rev 91, 1447-1531.

Schiaffino, S., Rossi, A. C., Smerdu, V., Leinwand, L. A., and Reggiani, C. (2015). Developmental myosins: expression patterns and functional significance. Skelet Muscle 5, 22.

Shelton, M., Metz, J., Liu, J., Carpenedo, R. L., Demers, S. P., Stanford, W. L., and Skerjanc, I. S. (2014). Derivation and expansion of PAX7-positive muscle progenitors from human and mouse embryonic stem cells. Stem Cell Reports 3, 516-529.

Snider, L., Geng, L. N., Lemmers, R. J., Kyba, M., Ware, C. B., Nelson, A. M., Tawil, R., Filippova, G. N., van der Maarel, S. M., Tapscott, S. J., et al. (2010). Facioscapulohumeral dystrophy: incomplete suppression of a retrotransposed gene. PLoS Genet 6, e1001181.

Song, Z., Cai, J., Liu, Y., Zhao, D., Yong, J., Duo, S., Song, X., Guo, Y., Zhao, Y., Qin, H., et al. (2009). Efficient generation of hepatocyte-like cells from human induced pluripotent stem cells. Cell Res 19, 1233-1242.

Springer, M. L., and Blau, H. M. (1997). High-efficiency retroviral infection of primary myoblasts. Somat Cell Mol Genet 23, 203-209.

Stuart, T., Butler, A., Hoffman, P., Hafemeister, C., Papalexi, E., Mauck, W. M., 3rd, Hao, Y., Stoeckius, M., Smibert, P., and Satija, R. (2019). Comprehensive Integration of Single-Cell Data. Cell 177, 1888-1902.e1821.

Swartz, E. W., Baek, J., Pribadi, M., Wojta, K. J., Almeida, S., Karydas, A., Gao, F. B., Miller, B. L., and Coppola, G. (2016). A Novel Protocol for Directed Differentiation of C9orf72-Associated Human Induced Pluripotent Stem Cells Into Contractile Skeletal Myotubes. Stem Cells Transl Med 5, 1461-1472.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Tawil, R., and Van Der Maarel, S. M. (2006). Facioscapulohumeral muscular dystrophy. Muscle Nerve 34, 1-15.

Thorsteinsdottir, S., Deries, M., Cachaco, A. S., and Bajanca, F. (2011). The extracellular matrix dimension of skeletal muscle development. Dev Biol 354, 191-207.

Tung, P. Y., Blischak, J. D., Hsiao, C. J., Knowles, D. A., Burnett, J. E., Pritchard, J. K., and Gilad, Y. (2017). Batch effects and the effective design of single-cell gene expression studies. Sci Rep 7, 39921.

Uezumi, A., Nakatani, M., Ikemoto-Uezumi, M., Yamamoto, N., Morita, M., Yamaguchi, A., Yamada, H., Kasai, T., Masuda, S., Narita, A., et al. (2016). Cell-Surface Protein Profiling Identifies Distinctive Markers of Progenitor Cells in Human Skeletal Muscle. Stem Cell Reports 7, 263-278.

van den Boogaard, M. L., Lemmers, R., Balog, J., Wohlgemuth, M., Auranen, M., Mitsuhashi, S., van der Vliet, P. J., Straasheijm, K. R., van den Akker, R. F. P., Kriek, M., et al. (2016). Mutations in DNMT3B Modify Epigenetic Repression of the D4Z4 Repeat and the Penetrance of Facioscapulohumeral Dystrophy. Am J Hum Genet 98, 1020-1029.

van Mil, A., Balk, G. M., Neef, K., Buikema, J. W., Asselbergs, F. W., Wu, S. M., Doevendans, P. A., and Sluijter, J. P. G. (2018). Modelling inherited cardiac disease using human induced pluripotent stem cell-derived cardiomyocytes: progress, pitfalls, and potential. Cardiovasc Res 114, 1828-1842.

van Overveld, P. G., Lemmers, R. J., Sandkuijl, L. A., Enthoven, L., Winokur, S. T., Bakels, F., Padberg, G. W., van Ommen, G. J., Frants, R. R., and van der Maarel, S. M. (2003). Hypomethylation of D4Z4 in 4q-linked and non-4q-linked facioscapulohumeral muscular dystrophy. Nat Genet 35, 315-317.

Velling, T., Kusche-Gullberg, M., Sejersen, T., and Gullberg, D. (1999). cDNA cloning and chromosomal localization of human alpha(11) integrin. A collagen-binding, I domain-containing, beta(1)-associated integrin alpha-chain present in muscle tissues. J Biol Chem 274, 25735-25742.

von Maltzahn, J., Chang, N. C., Bentzinger, C. F., and Rudnicki, M. A. (2012). Wnt signaling in myogenesis. Trends Cell Biol 22, 602-609.

Wallace, L. M., Garwick, S. E., Mei, W., Belayew, A., Coppee, F., Ladner, K. J., Guttridge, D., Yang, J., and Harper, S. Q. (2011). DUX4, a candidate gene for facioscapulohumeral muscular dystrophy, causes p53-dependent myopathy in vivo. Ann Neurol 69, 540-552.

Wang, L. C., and Kernell, D. (2001). Fibre type regionalisation in lower hindlimb muscles of rabbit, rat and mouse: a comparative study. J Anat 199, 631-643.

Weintraub, H., Tapscott, S. J., Davis, R. L., Thayer, M. J., Adam, M. A., Lassar, A. B., and Miller, A. D. (1989). Activation of muscle-specific genes in pigment, nerve, fat, liver, and fibroblast cell lines by forced expression of MyoD. Proc Natl Acad Sci USA 86, 5434-5438.

Xi, H., Fujiwara, W., Gonzalez, K., Jan, M., Liebscher, S., Van Handel, B., Schenke-Layland, K., and Pyle, A. D. (2017). In Vivo Human Somitogenesis Guides Somite Development from hPSCs. Cell Rep 18, 1573-1585.

Xi, H., Langerman, J., Sabri, S., Chien, P., Young, C. S., Younesi, S., Hicks, M., Gonzalez, K., Fujiwara, W., Marzi, J., et al. (2020). A Human Skeletal Muscle Atlas Identifies the Trajectories of Stem and Progenitor Cells across Development and from Human Pluripotent Stem Cells. Cell Stem Cell.

Xu, C., Tabebordbar, M., Iovino, S., Ciarlo, C., Liu, J., Castiglioni, A., Price, E., Liu, M., Barton, E. R., Kahn, C. R., et al. (2013). A zebrafish embryo culture system defines factors that promote vertebrate myogenesis across species. Cell 155, 909-921.

Yang, Q., Yu, J., Yu, B., Huang, Z., Zhang, K., Wu, He, J., Mao, X., Zheng, P., and Chen, D. (2016). PAX3(+) skeletal muscle satellite cells retain long-term self-renewal and proliferation. Muscle Nerve 54, 943-951.

Yao, Z., Snider, L., Balog, J., Lemmers, R. J., Van Der Maarel, S. M., Tawil, R., and Tapscott, S. J. (2014). DUX4-induced gene expression is the major molecular signature in FSHD skeletal muscle. Hum Mol Genet 23, 5342-5352.

Yao, Z., Snider, L., Balog, J., Lemmers, R. J., Van Der Maarel, S. M., Tawil, R., and Tapscott, S. J. (2014). DUX4-induced gene expression is the major molecular signature in FSHD skeletal muscle. Hum Mol Genet 23, 5342-5352.

Yoshida, N., Yoshida, S., Koishi, K., Masuda, K., and Nabeshima, Y. (1998). Cell heterogeneity upon myogenic differentiation: down-regulation of MyoD and Myf-5 generates 'reserve cells'. J Cell Sci 111 (Pt 6), 769-779.

Young, M. D., Wakefield, M. J., Smyth, G. K., and Oshlack, A. (2010). Gene ontology analysis for RNA-seq: accounting for selection bias. Genome Biol 11, R14.

Zhang, J. M., Kamath, G. M., and Tse, D. N. (2019). Valid Post-clustering Differential Analysis for Single-Cell RNA-Seq. Cell Syst 9, 383-392 e386.

We claim:

1. A method, comprising:
  a) providing induced pluripotent stem cells (iPSCs) derived from reprogrammed primary myoblasts or primary fibroblasts;
  b) stimulating said induced pluripotent stem cells in an S3 differentiation media to create induced primary myocytes and a first plurality of undifferentiated myogenic stem cells;
  c) propagating said first plurality of undifferentiated myogenic stem cells in a transgene-free growth factor media to create induced secondary myocytes, wherein said induced secondary myocytes retain a genetic identity identical to that of said induced pluripotent stem cells; and
  d) expanding said induced secondary myocytes to create a second plurality of undifferentiated stem cells, wherein said second plurality of undifferentiated stem cells retain a genetic identity to that of said induced pluripotent stem cells.

2. The method of claim 1, wherein said expanding said induced secondary myocytes further creates a myotube tissue.

3. The method of claim 2, wherein said myotube tissue further differentiates into a striated muscle tissue.

4. The method of claim 1, wherein said iPSCs are derived from a healthy subject.

5. The method of claim 1, wherein said iPSCs are derived from a subject diagnosed with facioscapulohumeral muscular dystrophy 1.

6. The method of claim 1, wherein said iPSCs are derived from a subject diagnosed with fukutin-related protein dystroglycanopathy.

7. The method of claim 1, wherein said iPSCs are derived from a subject diagnosed with limb-girdle muscular dystrophy R7.

8. The method of claim 1, wherein said method further comprises propagating said second plurality of undifferentiated stem cells in the presence of said myotube tissue.

9. The method of claim 1, wherein said second plurality of undifferentiated stem cells retain an autonomous expression of PAX3 and MYOD1 muscle master regulatory genes.

10. The method of claim 9, wherein said muscle master regulatory genes are upregulated.

11. The method of claim 1, wherein second plurality of undifferentiated stem cells retain a commitment to myotube differentiation.

12. The method of claim 1, wherein said genetic identity of said expanded second plurality of undifferentiated stem cells is stable.

13. The method of claim 1, wherein said method further comprises inducing said expanded second plurality of undifferentiated stem cells into induced tertiary myoblasts with a growth medium.

* * * * *